United States Patent
Brown et al.

(10) Patent No.: US 11,110,114 B2
(45) Date of Patent: *Sep. 7, 2021

(54) DINUCLEOTIDES

(71) Applicant: OXFORD UNIVERSITY INNOVATION LIMITED, Botley (GB)

(72) Inventors: Tom Brown, Oxford (GB); Afaf Helmy El-Sagheer, Oxford (GB); Pawan Kumar, Oxford (GB)

(73) Assignee: Oxford University Innovation Limited, Botley (GB)

( * ) Notice: Subject to any disclaimer, the term of this patent is extended or adjusted under 35 U.S.C. 154(b) by 10 days.

This patent is subject to a terminal disclaimer.

(21) Appl. No.: 16/037,157

(22) Filed: Jul. 17, 2018

(65) Prior Publication Data
US 2019/0015439 A1  Jan. 17, 2019

Related U.S. Application Data

(60) Provisional application No. 62/533,542, filed on Jul. 17, 2017.

(51) Int. Cl.
| | | |
|---|---|---|
| *A61K 31/7084* | (2006.01) | |
| *A61P 31/00* | (2006.01) | |
| *A61P 35/00* | (2006.01) | |
| *C07D 201/00* | (2006.01) | |
| *C07H 19/16* | (2006.01) | |
| *C07H 19/00* | (2006.01) | |
| *C07H 19/06* | (2006.01) | |

(52) U.S. Cl.
CPC .......... *A61K 31/7084* (2013.01); *A61P 31/00* (2018.01); *A61P 35/00* (2018.01); *C07D 201/00* (2013.01); *C07H 19/00* (2013.01); *C07H 19/06* (2013.01); *C07H 19/16* (2013.01)

(58) Field of Classification Search
CPC ...... A61K 31/7084; A61P 31/00; A61P 35/00; C07H 19/16; C07H 19/06; C07H 19/00; C07D 201/00
See application file for complete search history.

(56) References Cited

U.S. PATENT DOCUMENTS

| | | |
|---|---|---|
| 8,846,883 B2 | 9/2014 | Brown |
| 10,604,755 B2 | 3/2020 | Collard et al. |
| 10,633,656 B2 | 4/2020 | Tuschl et al. |
| 10,669,577 B2 | 6/2020 | Ju et al. |
| 10,683,321 B2 | 6/2020 | Dukhan et al. |
| 10,844,430 B2 | 11/2020 | Andruzzi et al. |
| 2006/0183788 A1 | 8/2006 | Muller et al. |
| 2019/0023732 A1* | 1/2019 | Brown .................. C07H 21/04 |

OTHER PUBLICATIONS

"Products for DNA research," Glen Research, 2020.
Wuts and Greene, "Greene's protective groups in organic synthesis," 2007, Wiley-Interscience.
Makarova et al., "An updated evolutionary classification of CRISPR-Cas systems," Nat Rev Microbiology, Sep. 28, 2015, 13:722-736.
Makarova et al., "Unification of Cas protein families and a simple scenario for the origin and evolution of CRISPR-Cas systems," Biol Direct., 2011 6:38.
Makarova et al., Methods in Molecular Biology, 2015, 1311:47-75.
Barrangou, "Diversity of CRISPR-Cas immune systems and molecular machines," Genome Biology, 2015, 16:247.
Rueda et al., "Mapping the sugar dependency for rational generation of a DNA-RNA hybrid-guided Cas9 endonuclease," Nature Communications, 2017, 8:1610.
Gagnon and Corey, "Stepping toward therapeutic CRISPR," Proc. Natl. Acad. Sci., Dec. 22, 2015, 12:15536-15537, USA.
Rahdar et al., "Synthetic CRISPR RNA-Cas9-guided genome editing in human cells," Proc. Natl. Acad. Sci., Nov. 16, 2015,112:E7110-71 17, USA.
Zuris et al., "Cationic lipid-mediated delivery of proteins enables efficient protein-based genome editing in viro and in vivo," Nat. Biotechnol., Jan. 2015, 33:73-80.
Liang et al., "Rapid and highly efficient mammalian cell engineering via Cas9 protein transfection," J. Biotechnol., 2015, 208:44-53.
Yu et al., "Improved delivery of Cas9 protein/gRNA complexes using lipofectamine CRISPRMAX," Biotechnol. Lett., Feb. 18, 2016, 38:919-929.
Koshkin et al., "A simplified and efficient route to 2'-O, 4'-C-Methylene-linked bicyclic ribonucleosides (locked nucleic acid)," J. Org. Chem. 2001, 66:8504-8512.
Obika et al., "2'-O,4'-C-methylene bridged nucleic acid (2',4'-BNA): Synthesis and triplex forming properties," Bioorg. Med. Chem., 2001, 9:1001-1011.
El-Sagheer and Brown, "New strategy for the synthesis of chemically modified RNA constructs exemplified by hairpin and hammerhead ribozymes," Proc. Natl. Acad. Sci., Aug. 31, 2010, 107(35):15329-15334, USA.
Said et al., "Two-step synthesis of a 5'-azidothymidine building block for the assembly of oligonucleotides for triazole-forming ligations," Synlett, 2012, 23:2923-2926.
Beaucage and Iyer, "Advances in the synthesis of oligonucleotides by the phosphoramidite approach," Tetrahedron, 1992, 48(12):2223-2311.
El-Sagheer and Brown, Chem Soc Rev, Feb. 2010, 39:1388-1405.
Fujino et al., "Chimeric RNA oligonucleotides incorporating triazole-linked trinucleotides: synthesis and function as mRNA in cell-free translation reactions," J Org Chem, 2016, 81:8967-8976.

(Continued)

*Primary Examiner* — Lawrence E Crane
(74) *Attorney, Agent, or Firm* — Barnes & Thornburg LLP

(57) ABSTRACT

The present disclosure relates to novel dinucleotides comprising at least two locked nucleosides, one of which is directly attached to the 3' end of the triazole linker moiety and the other of which is directly linked to the 5' end of the triazole linker moiety and that are useful for the preparation of oligonucleotides. The disclosed dinucleotides may be used in gene therapy.

36 Claims, 31 Drawing Sheets

Specification includes a Sequence Listing.

(56) References Cited

OTHER PUBLICATIONS

Fujino et al., "Chimeric RNA oligonucleotides with triazole and phosphate linkages: synthesis and RNA interference," Chem Asian J, 2015, 10:2683-2688.
Isobe and Fujino, "Triazole-linked analogues of DNA and RNA synthesis and function," Chem Rec, 2014, 14:41-51.
Varizhuk et al., "Synthesis of triazole-linked oligonucleotides with high affinity to DNA complements and an analysis of their compatibility with biosystems," J Org Chem, Jun. 3, 2013, 78:5964-5969.
Varizhuk et al., "Synthesis, characterization and in vitro activity of thrombin-binding DNA aptamers with triazole internucleotide linkages," Eur J Med Chem, Jun. 25, 2013, 67:90-97.
El-Sagheer and Brown, "Click nucleic acid ligation: applications in biology and nanotechnology," Acc Chem Res, 2012, 45:1258-1267.
El-Sagheer et al., "Biocompatible artificial DNA linker that is read through by DNA polymerases and is functional in *Escherichia coli*," Proc Natl Acad Sci, Jul. 12, 2011, 108(28):11338-11343.
El-Sagheer and Brown, "Efficient RNA synthesis by in vitro transcription of a triazole-modified DNA template," Chemical Commun, Nov. 28, 2011, 47(44):12057-12058.
Birts et al., "Transcription of click linked DNA in human cells," Angew Chem Int Ed, 2014, 53:2362-2365.
Dallmann et al., "Structure and dynamics of triazole-linked DNA: biocompatibility explained," Chem Eur J, 2011, 17:14714-14717.
Madhuri and Kumar, "Design and synthesis of dephosphono DNA analogues containing 1, 2, 3-triazole linker and their UV-melting studies with DNA/RNA," Nucleosides, Nucleotides and Nucleic Acids, Feb. 3, 2012, 31(2):97-111.
El-Sagheer and Brown, "Combined nucleobase and backbone modifications enhance DNA duplex stability and preserve biocompatibility," Chem Sci, 2014, 5:253-259.
Shivalingam et al., "Molecular requirements of high-fidelity replication-competent DNA backbones for orthogonal chemical ligation," J Am Chem Soc, Jan. 18, 2017, 139, 1575-1583.
Palframan et al., "Synthesis of triazole-linked morpholino oligonucleotides via Cu catalysed cycloaddition," Org Biomol Chem, 2016, 14:3112-3119.
Singh and Wengel, "Universality of LNA-mediated high-affinity nucleic acid recognition," Chem Commun, 1998, 1247-1248.
Obika et al., "Stability and structural features of the duplexes containing nucleoside analogues with a fixed N-type conformation, 2'-O,4'-C-methyleneribonucleosides," Tetrahedron Lett, 1998, 39:5401-5404.
Kaur, Babu, and Maiti, "Perspectives on chemistry and therapeutic applications of locked nucleic acid (LNA)," Chem Rev, 2007, 107:4672-4697.
Watts, "Locked nucleic acid: Tighter is different," Chem Commun, May 2013, 49:5618-5620.
Miller and Kool, "A simple method for electrophilic functionalization of DNA," Org Lett, Sep. 19, 2002, 4(21):3599-3601.
Miller and Kool, "Versatile 5'-Functionalization of oligonucleotides on solid support: Amines, azides, thiols, and thioethers via phosphorus chemistry," J Org Chem, Mar. 5, 2004, 69:2404-2410.
Chan et al., "Polytriazoles as copper(I)-stabilizing ligands in catalysis," Org Lett, Jul. 30, 2004, 6(17):2853-2855.
Bood, M., et al. "Fluorescent nucleobase analogues for base-base FRET in nucleic acids: synthesis, photophysics and applications," BEILSTEIN Journal of Organic Chemistry, 2018, 14, 114-29.
Minuth, M. and Richert, C., "A Nucleobase Analogue that Pairs Strongly with Adenine," Angewandte Chemie International Edition, 2013, 52, 10874-7.

\* cited by examiner

PACE phosphoramidite    LNA dimer included in Phosphonoacetate internucleotide Linkage R=H, OH, OMe, F

SEQUENCE LISTING

```
<160> NUMBER OF SEQ ID NOS: 52

<210> SEQ ID NO 1
<211> LENGTH: 81
<212> TYPE: DNA
<213> ORGANISM: Artificial Sequence
<220> FEATURE:
<223> OTHER INFORMATION: modified template (ON15)
<220> FEATURE:
<221> NAME/KEY: modified_base
<222> LOCATION: (23)..(23)
<223> OTHER INFORMATION: m5c
<220> FEATURE:
<221> NAME/KEY: misc_feature
<222> LOCATION: (23)..(24)
<223> OTHER INFORMATION: triazole linkage
<220> FEATURE:
<221> NAME/KEY: misc_feature
<222> LOCATION: (24)..(24)
<223> OTHER INFORMATION: LNA thymidine

<400> SEQUENCE: 1
gcattcgagc aacgtaagat cgnnagcaca caatctcaca ctctggaatt cacactgaca      60
atactgccga cacacataac c                                                81

<210> SEQ ID NO 2
<211> LENGTH: 80
<212> TYPE: DNA
<213> ORGANISM: Artificial Sequence
<220> FEATURE:
<223> OTHER INFORMATION: unmodified template

<400> SEQUENCE: 2
acgttagcac gaagaggcat cttagcacac aatctcacac tctggaattc acactgacaa      60
tactcgcgaa cacacccaat                                                  80

<210> SEQ ID NO 3
<211> LENGTH: 19
<212> TYPE: DNA
<213> ORGANISM: Artificial Sequence
<220> FEATURE:
<223> OTHER INFORMATION: primer used for modified template
<220> FEATURE:
<221> NAME/KEY: misc_feature
<222> LOCATION: (1)..(1)
<223> OTHER INFORMATION: t derivatised with amidohexylfuorescein

<400> SEQUENCE: 3
tggttatgtg tgtcggcag                                                   19

<210> SEQ ID NO 4
<211> LENGTH: 19
<212> TYPE: DNA
<213> ORGANISM: Artificial Sequence
<220> FEATURE:
```

```
<223> OTHER INFORMATION: primer used for unmodified template
<220> FEATURE:
<221> NAME/KEY: misc_feature
<222> LOCATION: (1)..(1)
<223> OTHER INFORMATION: t derivatised with amidohexylfuorescein

<400> SEQUENCE: 4
tattgggtgt gttcgcgag                                               19

<210> SEQ ID NO 5
<211> LENGTH: 13
<212> TYPE: DNA
<213> ORGANISM: Artificial Sequence
<220> FEATURE:
<223> OTHER INFORMATION: modified oligonucleotide ON2
<220> FEATURE:
<221> NAME/KEY: modified_base
<222> LOCATION: (6)..(6)
<223> OTHER INFORMATION: n is m5c
<220> FEATURE:
<221> NAME/KEY: misc_feature
<222> LOCATION: (6)..(7)
<223> OTHER INFORMATION: triazole linkage
<220> FEATURE:
<221> NAME/KEY: misc_feature
<222> LOCATION: (7)..(7)
<223> OTHER INFORMATION: n is LNA thymidine

<400> SEQUENCE: 5
cgacgnntgc agc                                                     13

<210> SEQ ID NO 6
<211> LENGTH: 13
<212> TYPE: DNA
<213> ORGANISM: Artificial Sequence
<220> FEATURE:
<223> OTHER INFORMATION: modified oligonucleotide ON3
<220> FEATURE:
<221> NAME/KEY: modified_base
<222> LOCATION: (6)..(6)
<223> OTHER INFORMATION: n is m5c
<220> FEATURE:
<221> NAME/KEY: misc_feature
<222> LOCATION: (6)..(7)
<223> OTHER INFORMATION: triazole linkage

<400> SEQUENCE: 6
cgacgnttgc agc                                                     13

<210> SEQ ID NO 7
<211> LENGTH: 13
<212> TYPE: DNA
<213> ORGANISM: Artificial Sequence
<220> FEATURE:
<223> OTHER INFORMATION: modified oligonucleotide ON5
<220> FEATURE:
<221> NAME/KEY: misc_feature
<222> LOCATION: (6)..(6)
<223> OTHER INFORMATION: n is 5-methylcytosine LNA
<220> FEATURE:
<221> NAME/KEY: misc_feature
<222> LOCATION: (6)..(7)
<223> OTHER INFORMATION: triazole linkage

<400> SEQUENCE: 7
cgacgnttgc agc                                                     13

<210> SEQ ID NO 8
<211> LENGTH: 13
<212> TYPE: DNA
<213> ORGANISM: Artificial Sequence
```

```
<220> FEATURE:
<223> OTHER INFORMATION: modified oligonucleotide ON6
<220> FEATURE:
<221> NAME/KEY: misc_feature
<222> LOCATION: (6)..(6)
<223> OTHER INFORMATION: n is 5-methylcytosine LNA
<220> FEATURE:
<221> NAME/KEY: misc_feature
<222> LOCATION: (6)..(7)
<223> OTHER INFORMATION: triazole linkage
<220> FEATURE:
<221> NAME/KEY: misc_feature
<222> LOCATION: (7)..(7)
<223> OTHER INFORMATION: n is LNA thymidine

<400> SEQUENCE: 8
cgacgnntgc agc                                                              13

<210> SEQ ID NO 9
<211> LENGTH: 13
<212> TYPE: DNA
<213> ORGANISM: Artificial Sequence
<220> FEATURE:
<223> OTHER INFORMATION: modified oligonucleotide ON8
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: triazole linkage
<220> FEATURE:
<221> NAME/KEY: misc_feature
<222> LOCATION: (5)..(5)
<223> OTHER INFORMATION: n is LNA thymidine
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (9)..(10)
<223> OTHER INFORMATION: triazole linkage
<220> FEATURE:
<221> NAME/KEY: misc_feature
<222> LOCATION: (10)..(10)
<223> OTHER INFORMATION: n is LNA thymidine

<400> SEQUENCE: 9
cganntctnn agc                                                              13

<210> SEQ ID NO 10
<211> LENGTH: 13
<212> TYPE: DNA
<213> ORGANISM: Artificial Sequence
<220> FEATURE:
<223> OTHER INFORMATION: modified oligonucleotide ON9
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: triazole linkage
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (9)..(10)
<223> OTHER INFORMATION: triazole linkage
```

<400> SEQUENCE: 10
cganttctnt agc                                                                 13

<210> SEQ ID NO 11
<211> LENGTH: 13
<212> TYPE: DNA
<213> ORGANISM: Artificial Sequence
<220> FEATURE:
<223> OTHER INFORMATION: modified oligonucleotide ON11
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: triazole linkage
<220> FEATURE:
<221> NAME/KEY: misc_feature
<222> LOCATION: (7)..(7)
<223> OTHER INFORMATION: 5-methylcytosine LNA

<400> SEQUENCE: 11
cgacgnntgc agc                                                                 13

<210> SEQ ID NO 12
<211> LENGTH: 13
<212> TYPE: DNA
<213> ORGANISM: Artificial Sequence
<220> FEATURE:
<223> OTHER INFORMATION: modified oligonucleotide ON12
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: triazole linkage
<220> FEATURE:
<221> NAME/KEY: modified_base
<222> LOCATION: (7)..(7)
<223> OTHER INFORMATION: m5c

<400> SEQUENCE: 12
cgacgnntgc agc                                                                 13

<210> SEQ ID NO 13
<211> LENGTH: 13
<212> TYPE: DNA
<213> ORGANISM: Artificial Sequence
<220> FEATURE:
<223> OTHER INFORMATION: modified oligonucleotide ON13
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: triazole linkage
<220> FEATURE:
<221> NAME/KEY: misc_feature
<222> LOCATION: (5)..(5)
<223> OTHER INFORMATION: n is 5-methylcytosine LNA
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (9)..(10)
<223> OTHER INFORMATION: triazole linkage -continued

```
<220> FEATURE:
<221> NAME/KEY: misc_feature
<222> LOCATION: (10)..(10)
<223> OTHER INFORMATION: n is 5-methylcytosine LNA

<400> SEQUENCE: 13
cganntctnn agc                                                        13

<210> SEQ ID NO 14
<211> LENGTH: 13
<212> TYPE: DNA
<213> ORGANISM: Artificial Sequence
<220> FEATURE:
<223> OTHER INFORMATION: modified oligonucleotide ON14
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: triazole linkage
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (9)..(10)
<223> OTHER INFORMATION: triazole linkage
<220> FEATURE:
<221> NAME/KEY: modified_base
<222> LOCATION: (10)..(10)
<223> OTHER INFORMATION: m5c

<400> SEQUENCE: 14
cganntctnn agc                                                        13

<210> SEQ ID NO 15
<211> LENGTH: 81
<212> TYPE: DNA
<213> ORGANISM: Artificial Sequence
<220> FEATURE:
<223> OTHER INFORMATION: modified oligonucleotide ON15
<220> FEATURE:
<221> NAME/KEY: modified_base
<222> LOCATION: (23)..(23)
<223> OTHER INFORMATION: m5c
<220> FEATURE:
<221> NAME/KEY: misc_feature
<222> LOCATION: (23)..(24)
<223> OTHER INFORMATION: triazole linkage
<220> FEATURE:
<221> NAME/KEY: misc_feature
<222> LOCATION: (24)..(24)
<223> OTHER INFORMATION: n is LNA thymidine

<400> SEQUENCE: 15
gcattcgagc aacgtaagat cgnnagcaca caatctcaca ctctggaatt cacactgaca     60
atactgccga cacacataac c                                               81

<210> SEQ ID NO 16
<211> LENGTH: 13
<212> TYPE: DNA
<213> ORGANISM: Artificial Sequence
<220> FEATURE:
<223> OTHER INFORMATION: unmodified ON/duplex (ON100)
<220> FEATURE:
```

```
<221> NAME/KEY: modified_base
<222> LOCATION: (12)..(12)
<223> OTHER INFORMATION: m5c

<400> SEQUENCE: 16
ctcactatct gct                                                        13

<210> SEQ ID NO 17
<211> LENGTH: 18
<212> TYPE: DNA
<213> ORGANISM: Artificial Sequence
<220> FEATURE:
<223> OTHER INFORMATION: splint used

<400> SEQUENCE: 17
tgtgtgctag cgatctta                                                   18

<210> SEQ ID NO 18
<211> LENGTH: 13
<212> TYPE: RNA
<213> ORGANISM: Artificial Sequence
<220> FEATURE:
<223> OTHER INFORMATION: RNA target

<400> SEQUENCE: 18
gcuagagaag ucg                                                        13

<210> SEQ ID NO 19
<211> LENGTH: 12
<212> TYPE: DNA
<213> ORGANISM: Artificial Sequence
<220> FEATURE:
<223> OTHER INFORMATION: ON Sequence (ON code 100)
<220> FEATURE:
<221> NAME/KEY: misc_feature
<222> LOCATION: (12)..(12)
<223> OTHER INFORMATION: n is any suitable nucleobase (e.g. cytosine
      (C), guanine (G), adenine (A), thymine (T) or uracil (U)) or any
      suitable modified analogue thereof

<400> SEQUENCE: 19
ctcactatct gn                                                         12

<210> SEQ ID NO 20
<211> LENGTH: 12
<212> TYPE: DNA
<213> ORGANISM: Artificial Sequence
<220> FEATURE:
<223> OTHER INFORMATION: ON Sequence (ON code 200)
<220> FEATURE:
<221> NAME/KEY: misc_feature
<222> LOCATION: (1)..(1)
<223> OTHER INFORMATION: n is any suitable nucleobase (e.g. cytosine
      (C), guanine (G), adenine (A), thymine (T) or uracil (U)) or any
      suitable modified analogue thereof

<400> SEQUENCE: 20
ncactatctg ct                                                         12

<210> SEQ ID NO 21
<211> LENGTH: 12
<212> TYPE: DNA
<213> ORGANISM: Artificial Sequence
<220> FEATURE:
<223> OTHER INFORMATION: ON Sequence (ON Code 300)
<220> FEATURE:
<221> NAME/KEY: misc_feature
<222> LOCATION: (5)..(5)
<223> OTHER INFORMATION: n is any suitable nucleobase (e.g. cytosine
```

(C), guanine (G), adenine (A), thymine (T) or uracil (U)) or any
      suitable modified analogue thereof

<400> SEQUENCE: 21
ctcanatctg ct                                                          12

<210> SEQ ID NO 22
<211> LENGTH: 12
<212> TYPE: DNA
<213> ORGANISM: Artificial Sequence
<220> FEATURE:
<223> OTHER INFORMATION: ON Sequence (ON code 400)
<220> FEATURE:
<221> NAME/KEY: misc_feature
<222> LOCATION: (9)..(9)
<223> OTHER INFORMATION: n is any suitable nucleobase (e.g. cytosine
      (C), guanine (G), adenine (A), thymine (T) or uracil (U)) or any
      suitable modified analogue thereof

<400> SEQUENCE: 22
ctcactatng ct                                                          12

<210> SEQ ID NO 23
<211> LENGTH: 11
<212> TYPE: DNA
<213> ORGANISM: Artificial Sequence
<220> FEATURE:
<223> OTHER INFORMATION: ON Sequence (ON code 500)
<220> FEATURE:
<221> NAME/KEY: misc_feature
<222> LOCATION: (5)..(5)
<223> OTHER INFORMATION: n is any suitable nucleobase (e.g. cytosine
      (C), guanine (G), adenine (A), thymine (T) or uracil (U)) or any
      suitable modified analogue thereof
<220> FEATURE:
<221> NAME/KEY: misc_feature
<222> LOCATION: (8)..(8)
<223> OTHER INFORMATION: n is any suitable nucleobase (e.g. cytosine
      (C), guanine (G), adenine (A), thymine (T) or uracil (U)) or any
      suitable modified analogue thereof

<400> SEQUENCE: 23
ctcanatngc t                                                           11

<210> SEQ ID NO 24
<211> LENGTH: 13
<212> TYPE: RNA
<213> ORGANISM: Artificial Sequence
<220> FEATURE:
<223> OTHER INFORMATION: RNA target

<400> SEQUENCE: 24
agcagauagu gag                                                         13

<210> SEQ ID NO 25
<211> LENGTH: 13
<212> TYPE: DNA
<213> ORGANISM: Artificial Sequence
<220> FEATURE:
<223> OTHER INFORMATION: DNA target

<400> SEQUENCE: 25
agcagatagt gag                                                         13

<210> SEQ ID NO 26
<211> LENGTH: 25
<212> TYPE: DNA
<213> ORGANISM: Artificial Sequence
<220> FEATURE:

<223> OTHER INFORMATION: Splint used for ON8 and ON9

<400> SEQUENCE: 26 tttttgcta gagaagtcgt ttttt                                          25

<210> SEQ ID NO 27
<211> LENGTH: 25
<212> TYPE: DNA
<213> ORGANISM: Artificial Sequence
<220> FEATURE:
<223> OTHER INFORMATION: Splint used for ON13 and ON14

<400> SEQUENCE: 27 tttttgctg gagaggtcgt ttttt                                          25

<210> SEQ ID NO 28
<211> LENGTH: 81
<212> TYPE: DNA
<213> ORGANISM: Artificial Sequence
<220> FEATURE:
<223> OTHER INFORMATION: Modified oligonucleotide (ON15)
<220> FEATURE:
<221> NAME/KEY: modified_base
<222> LOCATION: (23)..(23)
<223> OTHER INFORMATION: m5c
<220> FEATURE:
<221> NAME/KEY: misc_feature
<222> LOCATION: (23)..(24)
<223> OTHER INFORMATION: triazole linkage
<220> FEATURE:
<221> NAME/KEY: misc_feature
<222> LOCATION: (24)..(24)
<223> OTHER INFORMATION: n is LNA thymidine

<400> SEQUENCE: 28
gcattcgagc aacgtaagat cgnnagcaca caatctcaca ctctggaatt cacactgaca    60
atactgccga cacacataac c                                             81

<210> SEQ ID NO 29
<211> LENGTH: 23
<212> TYPE: DNA
<213> ORGANISM: Artificial Sequence
<220> FEATURE:
<223> OTHER INFORMATION: ON18
<220> FEATURE:
<221> NAME/KEY: misc_feature
<222> LOCATION: (23)..(23)
<223> OTHER INFORMATION: n is 3'-alkyne 5-methylcytosine

<400> SEQUENCE: 29
gcattcgagc aacgtaagat cgn                                           23

<210> SEQ ID NO 30
<211> LENGTH: 58
<212> TYPE: DNA
<213> ORGANISM: Artificial Sequence
<220> FEATURE:
<223> OTHER INFORMATION: ON32
<220> FEATURE:
<221> NAME/KEY: misc_feature
<222> LOCATION: (1)..(1)
<223> OTHER INFORMATION: n is 5'-azide LNA thymidine

<400> SEQUENCE: 30
nagcacacaa tctcacactc tggaattcac actgacaata ctgccgacac acataacc     58

<210> SEQ ID NO 31
<211> LENGTH: 13

```
<212> TYPE: DNA
<213> ORGANISM: Artificial Sequence
<220> FEATURE:
<223> OTHER INFORMATION: ON33
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: normal phosphodiester linkage
<220> FEATURE:
<221> NAME/KEY: modified_base
<222> LOCATION: (7)..(7)
<223> OTHER INFORMATION: m5c

<400> SEQUENCE: 31
cgacgnntgc agc                                                          13

<210> SEQ ID NO 32
<211> LENGTH: 13
<212> TYPE: DNA
<213> ORGANISM: Artificial Sequence
<220> FEATURE:
<223> OTHER INFORMATION: ON34
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: normal phosphodiester linkage
<220> FEATURE:
<221> NAME/KEY: misc_feature
<222> LOCATION: (7)..(7)
<223> OTHER INFORMATION: n is 5-methylcytosine LNA

<400> SEQUENCE: 32
cgacgnntgc agc                                                          13

<210> SEQ ID NO 33
<211> LENGTH: 13
<212> TYPE: DNA
<213> ORGANISM: Artificial Sequence
<220> FEATURE:
<223> OTHER INFORMATION: oligonucleotide ON 1
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: normal phosphodiester linkage

<400> SEQUENCE: 33
cgacgnttgc agc                                                          13

<210> SEQ ID NO 34
<211> LENGTH: 13
<212> TYPE: DNA
<213> ORGANISM: Artificial Sequence
<220> FEATURE:
<223> OTHER INFORMATION: Oligonucleotide ON 4
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
```

```
<223> OTHER INFORMATION: normal phosphodiester linkage
<220> FEATURE:
<221> NAME/KEY: misc_feature
<222> LOCATION: (7)..(7)
<223> OTHER INFORMATION: n is LNA thymidine

<400> SEQUENCE: 34
cgacgnntgc agc                                                              13

<210> SEQ ID NO 35
<211> LENGTH: 13
<212> TYPE: DNA
<213> ORGANISM: Artificial Sequence
<220> FEATURE:
<223> OTHER INFORMATION: DNA target

<400> SEQUENCE: 35
gctgcaggcg tcg                                                              13

<210> SEQ ID NO 36
<211> LENGTH: 13
<212> TYPE: RNA
<213> ORGANISM: Artificial Sequence
<220> FEATURE:
<223> OTHER INFORMATION: RNA target

<400> SEQUENCE: 36
gcugcaggcg ucg                                                              13

<210> SEQ ID NO 37
<211> LENGTH: 13
<212> TYPE: DNA
<213> ORGANISM: Artificial Sequence
<220> FEATURE:
<223> OTHER INFORMATION: ON 35
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: normal phosphodiester linkage
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (9)..(10)
<223> OTHER INFORMATION: normal phosphodiester linkage
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (10)..(10)
<223> OTHER INFORMATION: m5c

<400> SEQUENCE: 37
cganntctnn agc                                                              13

<210> SEQ ID NO 38
<211> LENGTH: 13
<212> TYPE: DNA
<213> ORGANISM: Artificial Sequence
<220> FEATURE:
<223> OTHER INFORMATION: ON 36
<220> FEATURE:
<221> NAME/KEY: modified_base
```

```
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: normal phosphodiester linkage
<220> FEATURE:
<221> NAME/KEY: misc_feature
<222> LOCATION: (5)..(5)
<223> OTHER INFORMATION: n is 5-methylcytosine LNA
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (9)..(10)
<223> OTHER INFORMATION: normal phosphodiester linkage
<220> FEATURE:
<221> NAME/KEY: misc_feature
<222> LOCATION: (10)..(10)
<223> OTHER INFORMATION: n is 5-methylcytosine LNA

<400> SEQUENCE: 38
cganntctnn agc                                                          13

<210> SEQ ID NO 39
<211> LENGTH: 13
<212> TYPE: DNA
<213> ORGANISM: Artificial Sequence
<220> FEATURE:
<223> OTHER INFORMATION: DNA target

<400> SEQUENCE: 39
gctggagagg tcg                                                          13

<210> SEQ ID NO 40
<211> LENGTH: 13
<212> TYPE: RNA
<213> ORGANISM: Artificial Sequence
<220> FEATURE:
<223> OTHER INFORMATION: RNA target

<400> SEQUENCE: 40
gcuagagaag ucg                                                          13

<210> SEQ ID NO 41
<211> LENGTH: 18
<212> TYPE: DNA
<213> ORGANISM: Artificial Sequence
<220> FEATURE:
<223> OTHER INFORMATION: primer used for modified template

<400> SEQUENCE: 41
gcattcgagc aacgtaag                                                     18

<210> SEQ ID NO 42
<211> LENGTH: 18
<212> TYPE: DNA
<213> ORGANISM: Artificial Sequence
<220> FEATURE:
<223> OTHER INFORMATION: primer used for modified sequence

<400> SEQUENCE: 42
ggttatgtgt gtcggcag                                                     18

<210> SEQ ID NO 43
<211> LENGTH: 18
<212> TYPE: DNA
```

```
<213> ORGANISM: Artificial Sequence
<220> FEATURE:
<223> OTHER INFORMATION: primer used for unmodified template

<400> SEQUENCE: 43
attgggtgtg ttcgcgag                                                 18

<210> SEQ ID NO 44
<211> LENGTH: 18
<212> TYPE: DNA
<213> ORGANISM: Artificial Sequence
<220> FEATURE:
<223> OTHER INFORMATION: primer used for unmodified sequence

<400> SEQUENCE: 44
acgttagcac gaagaggc                                                 18

<210> SEQ ID NO 45
<211> LENGTH: 13
<212> TYPE: DNA
<213> ORGANISM: Artificial Sequence
<220> FEATURE:
<223> OTHER INFORMATION: duplex containing a single triazole linkage
      (ON1)
<220> FEATURE:
<221> NAME/KEY: modified_base
<222> LOCATION: (6)..(6)
<223> OTHER INFORMATION: m5c

<400> SEQUENCE: 45
cgacgcttgc agc                                                      13

<210> SEQ ID NO 46
<211> LENGTH: 13
<212> TYPE: DNA
<213> ORGANISM: Artificial Sequence
<220> FEATURE:
<223> OTHER INFORMATION: duplex containing a single triazole linkage
      (ON3)
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: triazole linkage

<400> SEQUENCE: 46
cgacgnttgc agc                                                      13

<210> SEQ ID NO 47
<211> LENGTH: 13
<212> TYPE: DNA
<213> ORGANISM: Artificial Sequence
<220> FEATURE:
<223> OTHER INFORMATION: duplex containing a single triazole linkage
      (ON4)
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (7)..(7)
<223> OTHER INFORMATION: n is LNA thymidine

<400> SEQUENCE: 47
cgacgcntgc agc                                                      13
```

```
<210> SEQ ID NO 48
<211> LENGTH: 13
<212> TYPE: DNA
<213> ORGANISM: Artificial Sequence
<220> FEATURE:
<223> OTHER INFORMATION: DNA target

<400> SEQUENCE: 48
gctgcaagcg tcg                                                          13

<210> SEQ ID NO 49
<211> LENGTH: 13
<212> TYPE: RNA
<213> ORGANISM: Artificial Sequence
<220> FEATURE:
<223> OTHER INFORMATION: RNA target

<400> SEQUENCE: 49
gcugcaagcg ucg                                                          13

<210> SEQ ID NO 50
<211> LENGTH: 13
<212> TYPE: DNA
<213> ORGANISM: Artificial Sequence
<220> FEATURE:
<223> OTHER INFORMATION: ON7
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (9)..(9)
<223> OTHER INFORMATION: m5c

<400> SEQUENCE: 50
cgacttctct agc                                                          13

<210> SEQ ID NO 51
<211> LENGTH: 13
<212> TYPE: DNA
<213> ORGANISM: Artificial Sequence
<220> FEATURE:
<223> OTHER INFORMATION: ON10
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(5)
<223> OTHER INFORMATION: n is LNA thymidine
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (10)..(10)
<223> OTHER INFORMATION: n is LNA thymidine

<400> SEQUENCE: 51
cgacntctcn agc                                                          13

<210> SEQ ID NO 52
<211> LENGTH: 13
<212> TYPE: DNA
<213> ORGANISM: Artificial Sequence
<220> FEATURE:
<223> OTHER INFORMATION: DNA target
```

```
<400> SEQUENCE: 52
gctagagaag tcg                                                    13
```

DINUCLEOTIDES

CROSS REFERENCE TO RELATED APPLICATIONS

This application claims the benefit under 35 U.S.C. § 119(e) of U.S. Provisional Patent Application No. 62/533,542, filed Jul. 17, 2017, the entire disclosure of which is incorporated herein by reference.

The project leading to this application has received funding from the European Union's Horizon 2020 research and innovation programme under the Marie Sklodowska-Curie grant agreement no: 656872.

SEQUENCE LISTING

Incorporated by reference in its entirety is a computer-readable nucleotide/amino acid sequence listing submitted concurrently herewith and identified as follows: One 17.6 KB ASCII (Text) file named "280043SeqList.txt" created on Sep. 28, 2018.

INTRODUCTION

The present invention relates to novel dinucleotides that are useful for the preparation of oligonucleotides. The present invention also relates to novel dinucleotides that are useful therapeutically.

BACKGROUND OF THE INVENTION

Oligonucleotides are of fundamental importance to many areas of molecular biology. They are essential tools in technologies such as DNA sequencing, forensics and genetic analysis. They can also be used therapeutically.

Oligonucleotides containing triazole inter-nucleoside linkages have attracted considerable attention in the last decade.[1-6] The most intensively studied of these is the biocompatible triazole-linkage shown in Formula (AA) below which has recently emerged as an important tool in the chemical synthesis of long pieces of DNA.[7]

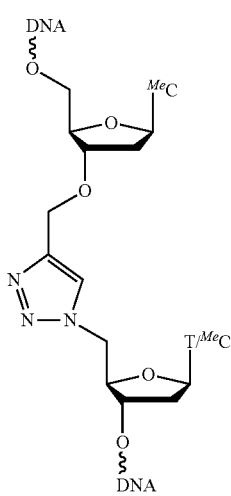

(AA)

The triazole linkage shown in Formula (AA) above is a mimic of natural phosphodiester-linked DNA and is functional in bacterial and human cells.[8-10] However, oligonucleotides incorporating this linkage form less stable duplexes with complementary RNA/DNA targets compared to unmodified DNA strands.[11, 12] This makes them unfit for use as antisense oligonucleotides where high binding affinity for the target nucleic acid is essential.

This problem was partially addressed by the introduction of an aminoethylphenoxazine nucleobase (G-clamp) on the 3'-side of the triazole linkage (see Formula (BB) below), which significantly enhances the thermal stability of the modified duplex.[13]

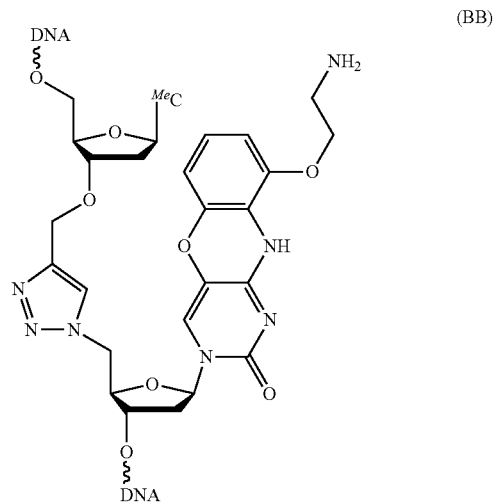

(BB)

However, G-clamp present in Formula (BB) is mildly mutagenic[14] and, being a mimic of 2'-deoxycytidine, it does not provide a solution for all nucleobase combinations.

Recently, oligonucleotides featuring triazole-linked morpholino nucleotides (see Formula (CC) below) have been shown to hybridize to their RNA targets with slightly improved affinity compared to triazole alone.[15] However, the resulting duplexes remain thermally less stable than their unmodified counterparts.

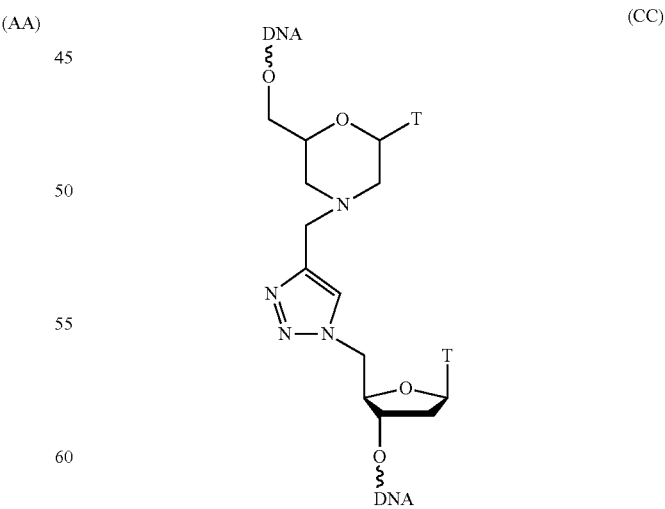

(CC)

The use of triazole inter-nucleoside linkages improves stability of the oligonucleotide to nucleases. However, in view of the foregoing, there is clearly a need for further improved triazole-linked oligonucleotides. In particular, there is a need for further improved triazole-linked oligonucleotides that possess improved binding affinities for complementary DNA and/or RNA strands and which are resistant to nuclease degradation.

Furthermore, there is a need for facile approaches to synthesise these oligonucleotides using conventional synthetic chemical techniques. U.S. Pat. No. 8,846,883 describes how these triazole inter-nucleoside linkages can be formed by "click" chemistry in which an oligonucleotide with a terminal azide reacts with another oligonucleotide with a terminal alkyne group to form an inter-nucleoside linkage comprising a triazole ring. However, chemical ligation is manual and slow process. Furthermore, absent a template to hold multiple oligonucleotide portions in place and ensure they ligate in the correct order, this reaction is only really useful to ligate two (oligo)nucleotide strands together provide a single triazole linkage. Even with a template to arrange the various portions in the correct order, the individual (oligo)nucleotides to be ligated will need to be short (e.g. in the case of therapeutic oligonucleotides) and this will impede their ability hybridise to the complementary DNA or RNA template, thereby reducing the effectiveness of templating.

The present invention was devised with the foregoing in mind.

SUMMARY OF THE INVENTION

According to one aspect of the present invention, there is provided a dinucleotide of Formula (I) (II) or (III) as defined herein.

According to a second aspect of the present invention, there is provided a process for making an oligonucleotide as defined herein.

According to a third aspect of the present invention, there is provided a dinucleotide of formula (III) as defined herein for use in therapy.

According to a fourth aspect of the present invention, there is provided a method of preparing a target oligonucleotide as defined herein, the method comprising reacting a dinucleotide of formula (I) or (II) with one or more further nucleotides, dinucleotides and/or oligonucleotides.

According to a fifth aspect of the present invention, there is provided an oligonucleotide prepared by the process of the fourth aspect of the present invention.

According to a sixth aspect of the present invention, there is provided the use of an oligonucleotide prepared by the process of the fourth aspect of the present invention as antisense RNA or interference RNA (RNAi, e.g. siRNA or miRNA) or an RNA component of a CRISPR-Cas system (e.g. crRNA, tracrRNA or gRNA).

According to another aspect of the present invention, there is provided the use of an oligonucleotide prepared by the process of the fourth aspect of the present invention as:
  a template for amplification in a polymerase chain reaction (PCR):
  as a template in a DNA replication process;
  as a template in a transcription process to provide a corresponding RNA transcript, or as a template in a reverse transcription process to provide a corresponding DNA transcript;
  as template in a translation process to produce a corresponding protein or peptide; or to guide one or more proteins of interest to a target DNA or RNA.

DETAILED DESCRIPTION OF THE INVENTION

Definitions

Figure 1:
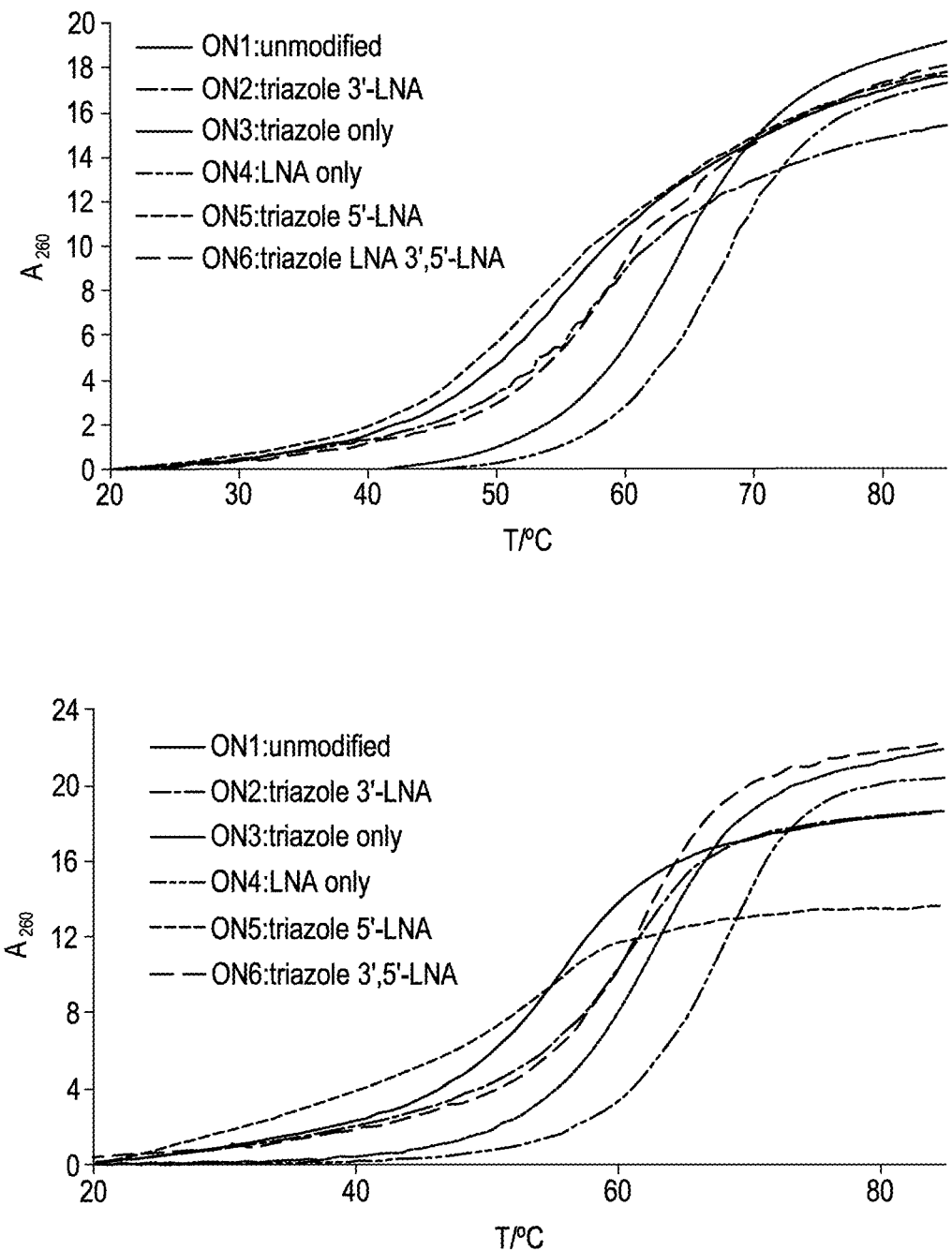
FIG. 1 shows representative melting curves for duplexes containing a single triazole linkage (MeC-T step, left against DNA target and right against RNA target). For sequences see Table 8.

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or examples of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

The phrase "oligonucleotide of the invention" means those oligonucleotides which are disclosed herein, both generically and specifically.

The term "oligonucleotide" refers to a polynucleotide strand. It will be appreciated by those skilled in the art that an oligonucleotide has a 5' and a 3' end and comprises a sequence of nucleosides linked together by inter-nucleoside linkages.

The terms "oligonucleotide analogue" and "nucleotide analogue" refer to any modified synthetic analogues of oligonucleotides or nucleotides respectively that are known in the art. Examples of oligonucleotide analogues include peptide nucleic acids (PNAs), morpholino oligonucleotides, phosphorothioate oligonucleotides, phosphorodithioate oligonucleotides, alkylphosphonate oligonucleotides, acylphosphonate oligonucleotides and phosphoramidite oligonucleotides.

The term "nucleobase analogue" refers to any analogues of nucleobases known in the art. The skilled person will appreciate there to be numerous natural and synthetic nucleobase analogues available in the art which could be employed in the present invention. As such, the skilled person will readily be able to identify suitable nucleobase analogues for use in the present invention. Commonly available nucleobase analogues are commercially available from a number of sources (for example, see the Glen Research catalogue (http://www.glenresearch.com/Catalog/contents.php). It will also be appreciated that the term "nucleobase analogue" covers: universal/degenerate bases (e.g. 3-nitropyrrole, 5-nitroindole and hypoxanthine); fluorescent bases (e.g. tricyclic cytosine analogues (tCO, tCS) and 2-aminopurine); base analogues bearing reactive groups selected from alkynes, thiols or amines; and base analogues that can crosslink oligonucleotides to DNA, RNA or proteins (e.g. 5-bromouracil or 3-cyanovinyl carbazole).

The nucleobase or nucleobase analogue is attached to a sugar moiety (typically ribose or deoxyribose) or a ribose or deoxyribose mimic, for example a chemically modified sugar derivative (e.g. a chemically modified ribose or deoxyribose) or a cyclic group that functions as a synthetic mimic of a ribose or deoxyribose sugar moiety (e.g. the morpholino ring present in morpholino oligonucleotides). The term "nucleoside" is used herein to refer to a moiety composed of a sugar/a ribose or deoxyribose mimic bound to a nucleobase/nucleobase analogue. The term nucleoside as used herein excludes the inter-nucleoside linkage that connects adjacent nucleosides together. An "inter-nucleoside linkage" is a linking group that connects the rings of the sugar/ribose or deoxyribose mimic of adjacent nucleosides.

The terms "locked nucleic acid", "LNA" or "locked nucleoside" are used herein to refer to nucleic acids or nucleosides comprising a ribose or deoxyribose moiety or analogues thereof as further defined herein (in formula (I) or (II)) in which the conformation of the ring is fixed or locked in a specific conformation, typically by a bridging group. Typically the bridging group connects the 2' and 4' carbon atoms of the ribose or deoxyribose rings and locks the ribose or deoxyribose in the 3'-endo conformation (which is often found in A-form duplexes). Examples of locked nucleic acid/nucleoside structures are well known in the art and are commercially available.

The Target Oligonucleotides

The applicants have discovered novel target oligonucleotide or oligonucleotide analogues having a 5' and a 3' end and comprising a sequence of nucleosides linked together by inter-nucleoside linkages, wherein at least one inter-nucleoside linkage is a triazole linker moiety and the nucleoside attached to the 3' end of the triazole linker moiety is a locked nucleoside.

It will be appreciated by those skilled in the art that an inter-nucleoside linkage will have a 5' end (or 5' side) that links to the nucleoside on the 5' side, and 3' end (or 3' side) that links to the nucleoside on the 3' side of linkage. The 3' and 5' nomenclature is well established in the nucleic acid field.

The applicant has surprisingly found that the provision of a locked nucleoside attached to the 3' end of the triazole linker moiety is associated with a notable increase in thermal melting temperature of duplexes formed by the hybridisation of the oligonucleotide of the invention with a complementary DNA or RNA strand. In addition, these oligonucleotides are much more stable to nuclease degradation when compared to corresponding oligonucleotides comprising just locked nucleosides alone. This indicates that these oligonucleotides will be suitable for use in vivo.

The combination of the two aforementioned advantages (namely the increased nuclease stability together with the increase in the thermal melting temperatures observed upon binding of the oligonucleotides of the present invention to complementary DNA or RNA strands) makes these new oligonucleotides particularly advantageous.

The locked nucleoside is directly attached to the 3' end of the triazole linker moiety at the 4' carbon of the locked ribose or deoxyribose ring.

The oligonucleotide may comprise multiple locked nucleosides in its sequence, for example there may be two, three, four, five or more locked nucleosides present. The additional locked nucleosides may be present at any position in the oligonucleotide.

It is preferred that the oligonucleotide comprises at least two locked nucleosides, one of which is directly attached to the 3' end of the triazole linker moiety and the other of which is directly linked to the 5' end of the triazole linker moiety. These particular oligonucleotides are associated with even greater nuclease stability when compared to the oligonucleotides of the invention with just one locked nucleoside present at the 3' end of the triazole linkage. It is therefore expected that the oligonucleotides of this embodiment of the invention will be particularly suitable for in vivo applications.

The oligonucleotide comprises one or more dinucleotide moieties of the formula:

Formula (IV)

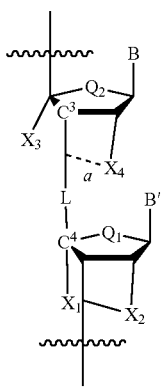

wherein:

$C^3$ is a 3' carbon;

$C^4$ is a 4' carbon;

bond a, $Q_1$, $Q_2$, B, B', $X_1$, $X_2$, $X_3$ and $X_4$ are all as defined herein and L is triazole linking moiety as defined herein.

In an embodiment, the entire oligonucleotide is formed of dinucleotide moieties of Formula (IV) above linked together. Such oligonucleotides have high proportions of triazole linkages.

The present invention relates to novel dinucleotide monomers that can be used to synthesise oligonucleotides comprising one or more dinucleotide moieties as defined above. The dinucleotide monomers can be incorporated into standard phosphoroamidite-based or H-phosphonate-based procedures for the synthesis of the target oligonucleotides. These procedures are typically solid-phase synthetic procedures that are fast, reliable and well established. Thus, the ability to be able to synthesis the target oligonucleotides by these procedures represents a major advance.

Dinucleotides of the Invention

According to one aspect of the present invention, there is provided a dinucleotide of Formula (I) or Formula (II), or a salt or solvate thereof, as shown below:

Formula (I)

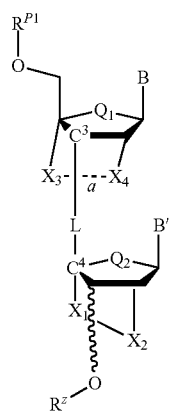

Formula (II)

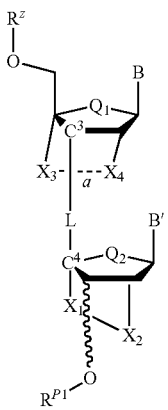

wherein:

$C^3$ and $C^4$ are the carbon atoms at the 3' and 4' positions of their respective 5-membered rings;

$Q_1$ and $Q_2$ are independently selected from $CR^pR^q$, O, S or $NR^s$, wherein $R^p$ and $R^q$ are each independently selected from H, (1-4C)alkyl or halo and $R^s$ is selected from hydrogen or (1-4C)alkyl;

B and B' are each independently a nucleobase or nucleobase analogue;

$R^{P1}$ is a protecting group;

bond a is absent or a single bond;

one of $X_1$ and $X_2$ is $(CR^aR^b)_x$ (where x is selected from 1 or 2) and the other is $CR^aR^b$, O, $NR^c$ or S, wherein $R^a$ and $R^b$ are independently selected from hydrogen, (1-2C)alkyl, hydroxy, amino, halo or mercapto, and $R^c$ is selected from hydrogen or a (1-6C)alkyl; or one of $X_1$ and $X_2$ is O and the other is $NR^c$;

one of $X_3$ and $X_4$ is $(CR^dR^e)_y$ (wherein y is selected from 1 or 2) and the other is $CR^dR^e$, O, $NR^f$ or S, wherein $R^d$ and $R^e$ are independently selected from hydrogen, (1-2C)alkyl, hydroxy, amino, halo or mercapto, and $R^f$ is selected from hydrogen or a (1-6C)alkyl; or one of $X_3$ and $X_4$ is O and the other is $NR^f$; or one of $X_3$ and $X_4$ is H and the other is selected from H, OH, $NH_2$, $OCH_3$ or F;

$R^z$ is a solid support or a group of formula $A_1$ or $A_2$ shown below:

(A₁)

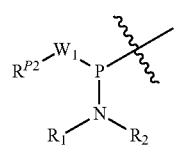

(A₂)

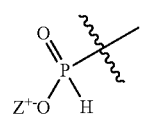

wherein:

denotes the point of attachment;
$W_1$ is selected from O, S or (1-4C)alkyl;
$R^{P2}$ is a protecting group;
$Z^+$ is a positively charged counter ion;
$R_1$ and $R_2$ are independently selected from hydrogen or (1-6C)alkyl, wherein said alkyl is optionally substituted with one or more substituents selected from hydroxy, halo, amino, nitro, cyano or (1-2C)haloalkyl; or
$R_1$ and $R_2$ are linked, such that, together with the nitrogen to which they are attached they form a 5-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro or hydroxy; and
L is a triazole phosphodiester mimic, optionally of Formula A or Formula B, shown below:

Formula A

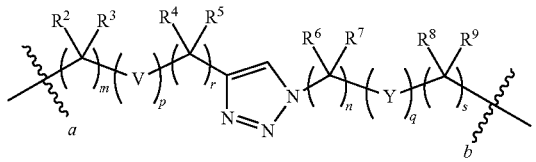

Formula B

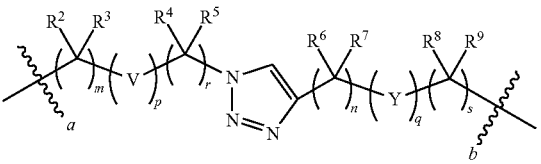

wherein:

denotes the point of attachment to $C^3$;

denotes the point of attachment to $C^4$;
$R^2$, $R^3$, $R^4$, $R^5$, $R^6$, $R^7$, $R^8$ and $R^9$ are each independently selected from hydrogen or (1-4C)alkyl, wherein each (1-4C)alkyl is optionally substituted with one or more $NH_2$, OH or SH;
V and Y are independently selected from O, S or $NR^x$, wherein $R^x$ is selected from hydrogen or (1-4C)alkyl;
m, n, r and s are integers independently selected from 0 to 2; and p and q are integers independently selected from 0 to 1;
with the proviso that:
i) the sum of integers m, n, p, q, r and s is either 0, 1, 2, 3, 4, 5 or 6;
ii) when $W_1$ is a (1-4C)alkyl, $R^{P2}$ is absent; and
iii) bond a is only absent when one of $X_3$ and $X_4$ is H and the other is selected from H, OH, $NH_2$, $OCH_3$ or F.

In an embodiment, the dinucleotide is of Formula (I).
In another embodiment, the dinucleotide is of Formula (II).

Particular dinucleotides of the invention include, for example, dinucleotides of the formula I or II, or salts and/or solvates thereof, wherein, unless otherwise stated, each of bond a, $Q_1$, $Q_2$, B, B', $R^{P1}$, $R^{P2}$, $X_1$, $X_2$, $X_3$, $X_4$, $R_2$, $W_1$, Z, $R_1$, $R_2$, L, and any associated substituent groups has any of the meanings defined hereinbefore or in any of paragraphs (1) to (55) hereinafter:—

(1) $Q_1$ and $Q_2$ are independently selected from $CR^pR^q$, O, S or $NR^s$, wherein $R^p$ and $R^q$ are each independently selected from H, (1-2C)alkyl or fluoro, and $R^s$ is selected from hydrogen or (1-4C)alkyl;

(2) $Q_1$ and $Q_2$ are independently selected from $CH_2$, O, S or $NR^s$, wherein $R^s$ is selected from hydrogen or (1-4C)alkyl;

(3) $Q_1$ and $Q_2$ are independently selected from O, S or $NR^s$, wherein $R^s$ is selected from hydrogen or (1-4C)alkyl;

(4) $Q_1$ and $Q_2$ are independently selected from O or S;

(5) $Q_1$ and $Q_2$ are both oxygen;

(6) $R^{P1}$ and $R^{P2}$ are protecting groups independently selected from the group consisting of an alkanoyl group (e.g. acetyl or pivaloyl), an aroyl group (e.g. benzoyl), an arylmethyl group (e.g. benzyl), an ether (e.g. methylether, t-butyl ether, β-methoxyethoxymethyl, allylether, methoxymethyl ether or p-methoxybenzyl ether), a silyl ether (e.g. trimethylsilyl, tert-butyldimethylsilyl, tri-iso-propylsilyloxymethyl or triisopropylsilyl), an alkylthiol (e.g. methylthiomethyl), an alkylcyano (e.g. β-cyanoethyl or 1,1-dimethyl-2-cyanoethyl), an alkyl thiobenzoyl (e.g. ethylthiobenzoyl), trityl-based compound (e.g. 4,4'-dimethoxytrityl, 4-methoxytriphenylmethyl or triphenylmethyl), a or a cyclic saturated heterocyclic ring (e.g. tetrahydropyranyl or tetrahydrofuran);

(7) $R^{P1}$ and $R^{P2}$ are protecting groups independently selected from the group consisting of an alkanoyl group (e.g. acetyl or pivaloyl), an aroyl group (e.g. benzoyl), an arylmethyl group (e.g. benzyl), an ether (e.g. methylether, t-butyl ether, β-methoxyethoxymethyl, allylether, methoxymethyl ether or p-methoxybenzyl ether), a silyl ether (e.g. trimethylsilyl, tert-butyldimethylsilyl, tri-iso-propylsilyloxymethyl or triisopropylsilyl), an alkylthiol (e.g. methylthiomethyl), an alkylcyano (e.g. β-cyanoethyl or 1,1-dimethyl-2-cyanoethyl), an alkyl thiobenzoyl (e.g. ethylthiobenzoyl) or a trityl-based compound (e.g. 4,4'-dimethoxytrityl, 4-methoxytriphenylmethyl or triphenylmethyl);

(8) $R^{P1}$ and $R^{P2}$ are protecting groups independently selected from the group consisting of an alkanoyl group (e.g. acetyl or pivaloyl), an aroyl group (e.g. benzoyl), an arylmethyl group (e.g. benzyl), an alkylcyano (e.g. β-cyanoethyl or 1,1-dimethyl-2-cyanoethyl), an alkyl thiobenzoyl (e.g. ethylthiobenzoyl) or a trityl-based compound (e.g. 4,4'-dimethoxytrityl, 4-methoxytriphenylmethyl or triphenylmethyl);

(9) $R^{P1}$ and $R^{P2}$ are protecting groups independently selected from the group consisting of acetyl, pivaloyl, benzoyl, benzyl, methylether, t-butyl ether, β-methoxyethoxymethyl, allylether, methoxymethyl ether, p-methoxybenzyl ether, trimethylsilyl, tert-butyldimethylsilyl, tri-iso-propylsilyloxymethyl, triisopropylsilyl, methylthiomethyl, β-cyanoethyl or 1,1-dimethyl-2-cyanoethyl, ethylthiobenzoyl, 4,4'-dimethoxytrityl, 4-methoxytriphenylmethyl or triphenylmethyl;

(10) $R^{P1}$ and $R^{P2}$ are protecting groups independently selected from the group consisting of acetyl, pivaloyl, benzoyl, benzyl, β-methoxyethoxymethyl, allylether, methoxymethyl ether, p-methoxybenzyl ether, trimethylsilyl, tert-butyldimethylsilyl, tri-iso-propylsilyloxymethyl, triisopropylsilyl, β-cyanoethyl or 1,1-dimethyl-2-cyanoethyl, ethylthiobenzoyl, 4,4'-dimethoxytrityl, 4-methoxytriphenylmethyl or triphenylmethyl;

(11) $R^{P1}$ is a trityl-based protecting group (e.g. 4,4'-dimethoxytrityl, 4-methoxytriphenylmethyl or triphenylmethyl);

(12) $R^{P1}$ is a 4,4'-dimethoxytrityl;

(13) $R^{P2}$ is an alkylcyano protecting group (e.g. β-cyanoethyl or 1,1-dimethyl-2-cyanoethyl);

(14) $R^{P2}$ is β-cyanoethyl;

(15) one of $X_1$ and $X_2$ is $CR^aR^b$ and the other of $X_1$ and $X_2$ is $CR^aR^b$, O, $NR^c$ or S, wherein $R^a$ and $R^b$ are independently selected from hydrogen, (1-2C)alkyl, hydroxy, amino, halo or mercapto, and $R^c$ is selected from hydrogen or a (1-6C)alkyl;

(16) one of $X_1$ and $X_2$ is $CR^aR^b$ and the other of $X_1$ and $X_2$ is $CR^aR^b$, O, $NR^c$ or S, wherein $R^a$ and $R^b$ are independently selected from hydrogen, methyl, hydroxy, amino or fluoro, and $R^c$ is selected from hydrogen or a (1-6C)alkyl;

(17) one of $X_1$ and $X_2$ is $CH_2$ and the other of $X_1$ and $X_2$ is $CH_2$, O, $NR^c$ or S, wherein $R^c$ is selected from hydrogen or a (1-6C)alkyl;

(18) one of $X_1$ and $X_2$ is $CH_2$ and the other of $X_1$ and $X_2$ is O, $NR^c$ or S, wherein $R^c$ is selected from hydrogen or a (1-6C)alkyl;

(19) one of $X_1$ and $X_2$ is $CH_2$ and the other of $X_1$ and $X_2$ is O or $NR^c$, wherein $R^c$ is selected from hydrogen or a (1-4C)alkyl;

(20) one of $X_1$ and $X_2$ is $CH_2$ and the other of $X_1$ and $X_2$ is O or S;

(21) one of $X_1$ and $X_2$ is $CH_2$ and the other of $X_1$ and $X_2$ is O;

(22) $X_1$ is $CH_2$ and $X_2$ is $CH_2$, O, $NR^c$ or S, wherein $R^c$ is selected from hydrogen or a (1-6C)alkyl;

(23) $X_1$ is $CH_2$ and $X_2$ is O or S;

(24) $X_1$ is $CH_2$ and $X_2$ is O;

(25) bond a is a single bond, and
  i) one of $X_3$ and $X_4$ is $CR^dR^e$ and the other is $CR^dR^e$, O, $NR^f$ or S, wherein $R^d$ and $R^e$ are independently selected from hydrogen, (1-2C)alkyl, hydroxy, amino, halo or mercapto, and $R^f$ is selected from hydrogen or a (1-6C)alkyl; or
  ii) one of $X_3$ and $X_4$ is O and the other is $NR^f$; or
  bond a is absent and one of $X_3$ and $X_4$ is H and the other is selected from H, OH, $NH_2$, $OCH_3$ or F;

(26) bond a is a single bond, and
  i) one of $X_3$ and $X_4$ is $CR^dR^e$ and the other is $CR^dR^e$, O, $NR^f$ or S, wherein $R^d$ and $R^e$ are independently selected from hydrogen, methyl, hydroxy, amino or fluoro, and $R^f$ is selected from hydrogen or a (1-6C) alkyl; or
  ii) one of $X_3$ and $X_4$ is O and the other is $NR^f$; or
  bond a is absent and one of $X_3$ and $X_4$ is H and the other is selected from H, OH, $NH_2$, $OCH_3$ or F;

(27) bond a is a single bond, and
  i) one of $X_3$ and $X_4$ is $CH_2$ and the other is $CH_2$, O, $NR^f$ or S, wherein $R^f$ is selected from hydrogen or a (1-6C)alkyl; or
  ii) one of $X_3$ and $X_4$ is O and the other is $NR^f$; or
  bond a is absent and one of $X_3$ and $X_4$ is H and the other is selected from H, OH, $NH_2$, $OCH_3$ or F;

(28) bond a is a single bond, and one of $X_3$ and $X_4$ is $CH_2$ and the other is $CH_2$, O, $NR^f$ or S, wherein $R^f$ is selected from hydrogen or a (1-6C)alkyl; or
  bond a is absent and one of $X_3$ and $X_4$ is H and the other is selected from H, OH, $NH_2$, $OCH_3$ or F;

(29) bond a is a single bond, and one of $X_3$ and $X_4$ is $CH_2$ and the other is O, $NR^f$ or S, wherein $R^f$ is selected from hydrogen or a (1-6C)alkyl; or
  bond a is absent and one of $X_3$ and $X_4$ is H and the other is selected from H or OH;

(30) bond a is a single bond, and one of $X_3$ and $X_4$ is $CH_2$ and the other is O, $NR^f$ or S, wherein $R^f$ is selected from hydrogen or a (1-6C)alkyl;

(31) bond a is a single bond, and one of $X_3$ and $X_4$ is $CH_2$ and the other is O or $NR^f$, wherein $R^f$ is selected from hydrogen or a (1-4C)alkyl;

(32) bond a is a single bond, and one of $X_3$ and $X_4$ is $CH_2$ and the other is O or S;

(33) bond a is a single bond, and $X_3$ is $CH_2$ and $X_4$ is O, $NR^f$ or S, wherein $R^f$ is selected from hydrogen or a (1-6C)alkyl;

(34) bond a is a single bond, and $X_3$ is $CH_2$ and $X_4$ is O or S;

(35) bond a is a single bond, and $X_3$ is $CH_2$ and $X_4$ is O;

(36) bond a is absent and one of $X_3$ and $X_4$ is H and the other is selected from H or OH;

(37) bond a is absent and $X_3$ is H and $X_4$ is OH;

(38) bond a is absent and both $X_3$ and $X_4$ are H;

(39) $R^z$ is a group of formula $A_1$ or $A_2$ shown below:

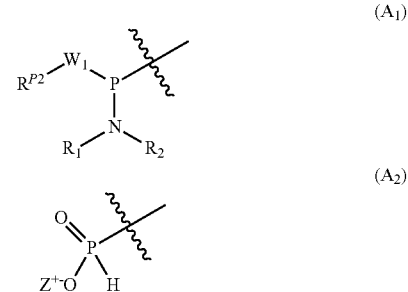

wherein:

denotes the point of attachment;
$W_1$ is selected from O or S;
$R^{P2}$ is a protecting group;
$Z^+$ is a positively charged counter ion (e.g. a monovalent cation such as $Na^+$, $K^+$, $^+NH_4$, $^+N(CH_3)_4$ or $^+N(CH_2CH_3)_4$);

R₁ and R₂ are independently selected from hydrogen or (1-6C)alkyl, wherein said alkyl is optionally substituted with one or more substituents selected from hydroxy, halo, amino, nitro, cyano or (1-2C)haloalkyl; or R₁ and R₂ are linked, such that, together with the nitrogen to which they are attached they form a 5-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro or hydroxy;

(40) R$^z$ is a group of formula A₁ shown below:

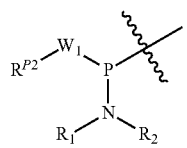

(A₁)

wherein:

denotes the point of attachment;
W₁ is selected from O or S;
R$^{P2}$ is a protecting group;
R₁ and R₂ are independently selected from hydrogen or (1-6C)alkyl, wherein said alkyl is optionally substituted with one or more substituents selected from hydroxy, halo, amino, nitro, cyano or (1-2C)haloalkyl; or R₁ and R₂ are linked, such that, together with the nitrogen to which they are attached they form a 5-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano, nitro or hydroxy;

(41) IV is a group of formula A₁ shown below:

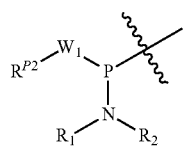

(A₁)

wherein:

denotes the point of attachment;
W₁ is O;
R$^{P2}$ is a protecting group;

R₁ and R₂ are independently selected from hydrogen or (1-6C)alkyl, wherein said alkyl is optionally substituted with one or more substituents selected from hydroxy, halo, amino, nitro, cyano or (1-2C)haloalkyl; or R₁ and R₂ are linked, such that, together with the nitrogen to which they are attached they form a 5-7 membered heterocyclic ring which is optionally substituted by one or more substituents selected from (1-4C)alkyl, halo, amino, cyano, nitro or hydroxy;

(42) R$^z$ is a group of formula A$_{1a}$ shown below:

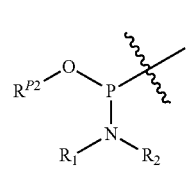

(A$_{1a}$)

wherein:

denotes the point of attachment;
R$^{P2}$ is an alkylcyano protecting group (e.g. β-cyanoethyl or 1,1-dimethyl-2-cyanoethyl);
R₁ and R₂ are independently selected from hydrogen or (1-6C)alkyl, wherein said alkyl is optionally substituted with one or more substituents selected from hydroxy, halo, amino, nitro, cyano or (1-2C)haloalkyl; or R₁ and R₂ are linked, such that, together with the nitrogen to which they are attached they form a 5-7 membered heterocyclic;

(43) R$^z$ is a group of formula A$_{1a}$ shown below:

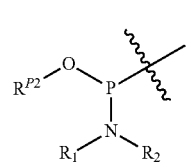

(A$_{1a}$)

wherein:

denotes the point of attachment;
R$^{P2}$ is an alkylcyano protecting group (e.g. β-cyanoethyl or 1,1-dimethyl-2-cyanoethyl);
R₁ and R₂ are independently selected from hydrogen or (1-6C)alkyl, wherein said alkyl is optionally substituted with one or more substituents selected from hydroxy, halo, amino, nitro, cyano or (1-2C)haloalkyl; or

(44) $R^z$ is a group of formula $A_{1a}$ shown below:

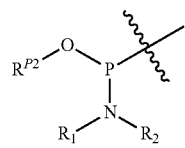

(A$_{1a}$)

wherein:

denotes the point of attachment;

$R^{P2}$ is an alkylcyano protecting group (e.g. β-cyanoethyl or 1,1-dimethyl-2-cyanoethyl);

$R_1$ and $R_2$ are independently selected from hydrogen or (1-6C)alkyl, or $R_1$ and $R_2$ are linked, such that, together with the nitrogen to which they are attached they form a 5-7 membered heterocyclic (e.g. pyrrolidin-1-yl);

(45) $R^z$ is a group of formula $A_{1a}$ shown below:

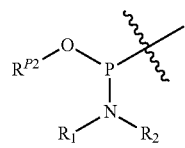

(A$_{1a}$)

wherein:

denotes the point or attachment;

$R^{P2}$ is an alkylcyano protecting group (e.g. β-cyanoethyl or 1,1-dimethyl-2-cyanoethyl);

$R_1$ and $R_2$ are independently selected from hydrogen or (1-6C)alkyl (e.g. isopropyl);

(46) $R^z$ is a group of formula $A_{1b}$ shown below:

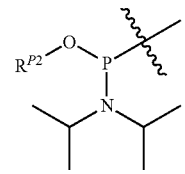

(A$_{1b}$)

wherein:

denotes the point of attachment; and $R^{P2}$ is a protecting group;

(47) $R^z$ is a group of formula $A_{1b}$ shown below:

(A$_{1b}$)

wherein:

denotes the point of attachment; and $R^{P2}$ is an alkylcyano protecting group (e.g. β-cyanoethyl or 1,1-dimethyl-2-cyanoethyl);

(48) $R^z$ is a group of formula $A_{1c}$ shown below:

(A$_{1c}$)

wherein:

denotes the point of attachment;

(49) L is a triazole phosphodiester mimic of Formula A or Formula B, shown below:

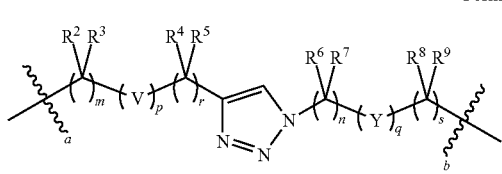

Formula A

-continued

Formula B

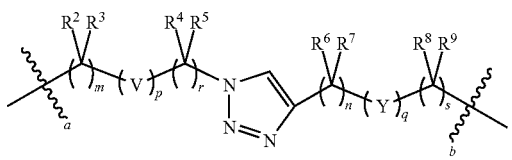

wherein:

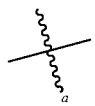

denotes the point of attachment to $C^3$;

denotes the point of attachment to $C^4$;
$R^2$, $R^3$, $R^4$, $R^5$, $R^6$, $R^7$, $R^8$ and $R^9$ are each independently selected from hydrogen or (1-4C)alkyl;
V and Y are independently selected from O, S or $NR^x$, wherein $R^x$ is selected from hydrogen or (1-4C)alkyl;
m, n, r and s are integers independently selected from 0 to 2; and
p and q are integers independently selected from 0 to 1;
with the proviso that the sum of integers m, n, p, q, r and s is either 0, 1, 2, 3, 4 or 5;

(50) L is a triazole phosphodiester mimic of Formula A or Formula B, shown below:

Formula A

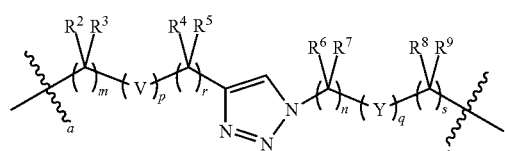

Formula B

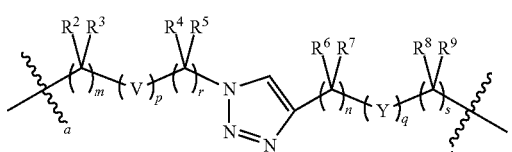

wherein:

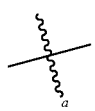

denotes the point of attachment to $C^3$;

denotes the point of attachment to $C^4$;
$R^2$, $R^3$, $R^4$, $R^5$, $R^6$, $R^7$, $R^8$ and $R^9$ are each independently selected from hydrogen or (1-4C)alkyl;
V and Y are independently selected from O or $NR^x$, wherein $R^x$ is selected from hydrogen or (1-4C)alkyl;
m, n, r and s are integers independently selected from 0 to 2; and
p and q are integers independently selected from 0 to 1;
with the proviso that the sum of integers m, n, p, q, r and s is either 0, 1, 2, 3, 4 or 5;

(51) L is a triazole phosphodiester mimic of Formula A or Formula B, shown below:

Formula A

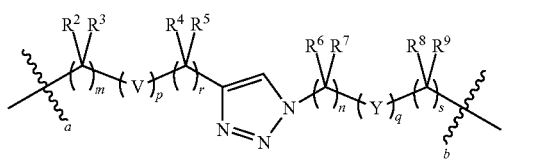

Formula B

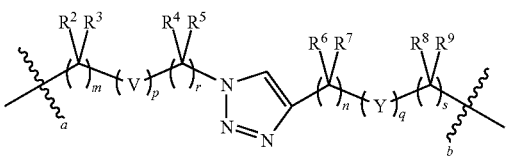

wherein:

denotes the point or attachment to $C^3$;

denotes the point of attachment to $C^4$;
$R^2$, $R^3$, $R^4$, $R^5$, $R^6$, $R^7$, $R^8$ and $R^9$ are each independently selected from hydrogen or methyl;
V and Y are independently selected from O or NH;
m, n, r and s are integers independently selected from 0 to 2; and
p and q are integers independently selected from 0 to 1;
with the proviso that the sum of integers m, n, p, q, r and s is either 0, 1, 2, 3, 4 or 5;

(52) L is a triazole phosphodiester mimic of Formula A or Formula B, shown below:

Formula A
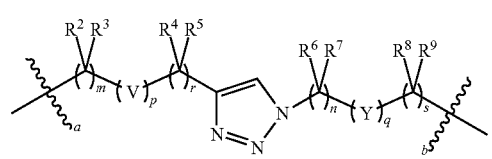

Formula B
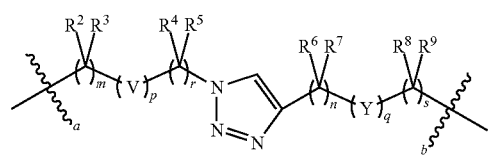

wherein:

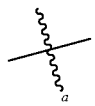

denotes the point of attachment to $C^3$;

denotes the point of attachment to $C^4$;
$R^2$, $R^3$, $R^4$, $R^5$, $R^6$, $R^7$, $R^8$ and $R^9$ are hydrogen;
V and Y are O;
m, n, r and s are integers independently selected from 0 to 2; and
p and q are integers independently selected from 0 to 1;
with the proviso that the sum of integers m, n, p, q, r and s is either 0, 1, 2, 3, 4 or 5;

(53) L is a triazole phosphodiester mimic selected from:

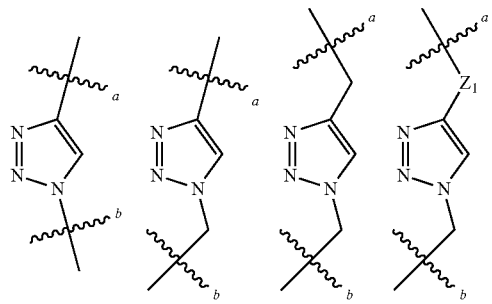

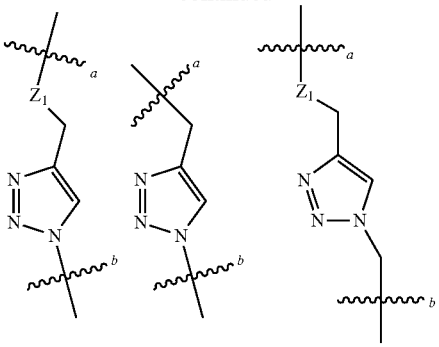

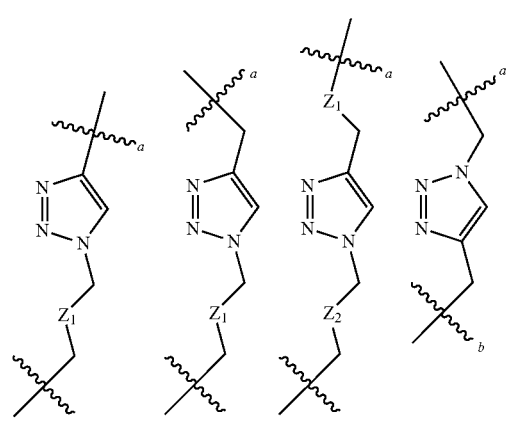

$Z_1$ and $Z_2$ are independently selected from O or NH;
denotes the point of attachment to $C^3$;
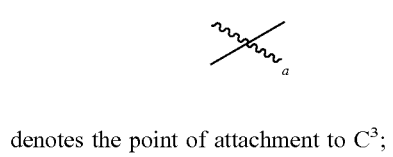
denotes the point of attachment to $C^4$;
(54) L is a triazole phosphodiester mimic selected from:
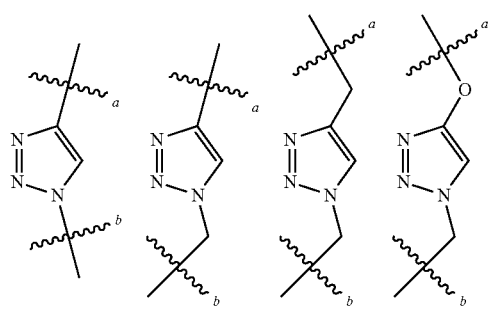
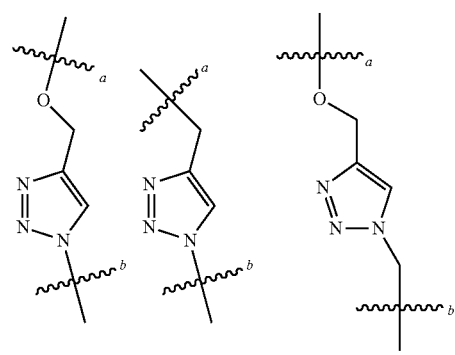
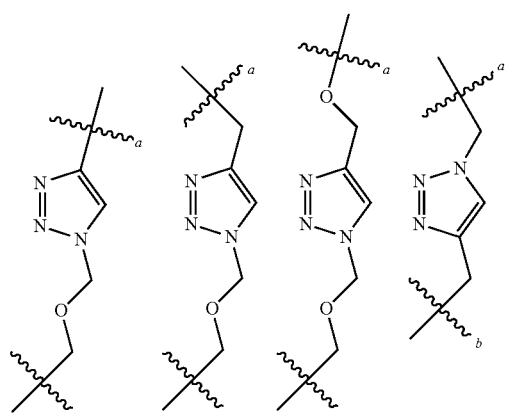
-continued
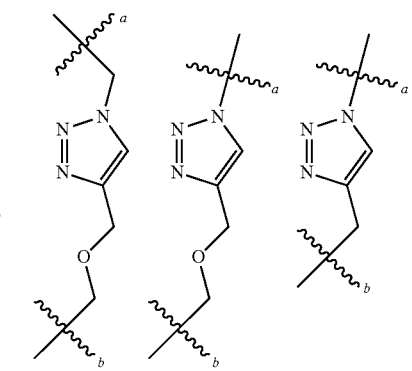
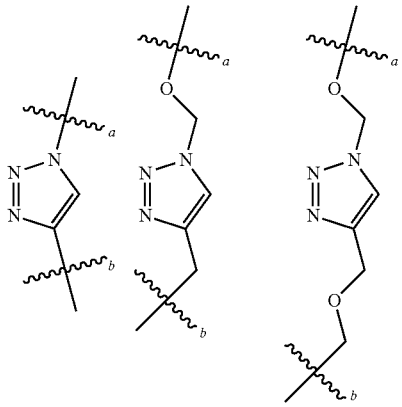
denotes the point of attachment to $C^3$;
denotes the point of attachment to $C^4$;
(55) L is a triazole phosphodiester mimic of the formula shown below:
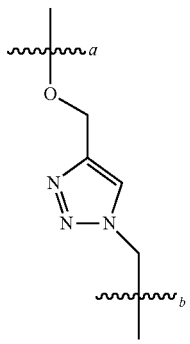

wherein:

denotes the point of attachment to $C^3$;

denotes the point of attachment to $C^4$.

Suitably, $Q_1$ and $Q_2$ are as defined in any one of paragraphs (1) to (5) above. Most suitably, $Q_1$ and $Q_2$ are as defined in paragraph (5) above.

Suitably, $R^{P1}$ is as defined in any one of paragraphs (6) to (12) above. Most suitably $R^{P1}$ is as defined in paragraph (12) above.

Suitably, $R^{P2}$ is as defined in any one of paragraphs (6) to (10) or (13) to (14) above. Most suitably, $R^{P2}$ is as defined in paragraph (14) above.

Suitably, $X_1$ and $X_2$ are as defined in any one of paragraphs (15) to (24) above. Most suitably $X_1$ and $X_2$ are as defined in paragraph (24) above.

Suitably, bond a is present.

Suitably, $X_3$ and $X_4$ are as defined in any one of paragraphs (25) to (38) above. More suitably, $X_3$ and $X_4$ are as defined in any one of paragraphs (28) to (35) above. Most suitably, $X_3$ and $X_4$ are as defined in paragraph (35) above.

Suitably, $R^z$ is as defined in any one of paragraphs (39) to (48) above. Most suitably, $R^z$ is as defined in paragraph (48) above.

Suitably, L is as defined in any one of paragraphs (49) to (55) above. Most suitably, L is as defined in paragraph (55) above.

Throughout the application it will be appreciated that B can be any suitable nucleobase (e.g. cytosine (C), guanine (G), adenine (A), thymine (T) or uracil (U)) or any suitable modified analogue thereof. In an embodiment, B is a nucleobase selected from A, G, C, T or U.

In a particular group of dinucleotides of the invention, the dinucleotide is of Formula (I) and $Q_1$ and $Q_2$ are oxygen, i.e. the dinucleotides have the structural formula Ia (a sub-definition of Formula (I)) shown below:

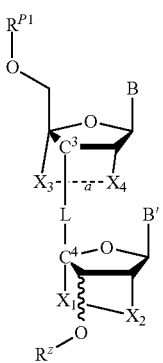

Formula Ia wherein $C^3$, $C^4$, bond a, $R^{P1}$, $R^z$, $X_1$, $X_2$, $X_3$, $X_4$, B, B' and L each have any one of the meanings defined herein.

In an embodiment of the dinucleotides of Formula Ia:
$R^{P1}$ is as defined in any one of paragraphs (6) to (12) above;
$X_1$ and $X_2$ are as defined in any one of paragraphs (15) to (24) above;
bond a, $X_3$ and $X_4$ are as defined in any one of paragraphs (25) to (38) above;
$R^z$ is as defined in any one of paragraphs (39) to (48) above; and
L is as defined in any one of paragraphs (49) to (55) above.

In another embodiment of the dinucleotides of Formula Ia:
$R^{P1}$ is as defined in paragraph (12) above;
$X_1$ and $X_2$ are as defined in paragraph (24) above;
bond a, $X_3$ and $X_4$ are as defined in any one of paragraphs (35) or (38) above;
$R^z$ is as defined in paragraph (48) above; and
L is as defined in paragraph (55) above.

In another particular group of dinucleotides of the invention, the dinucleotide is of Formula (I) and $R^z$ is as shown below, i.e. the dinucleotides have the structural formula Ib (a sub-definition of Formula (I)) shown below:

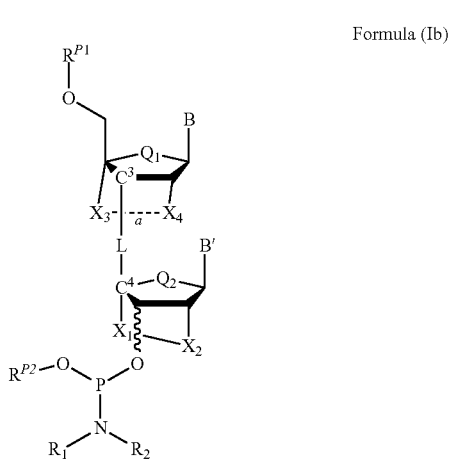

Formula (Ib)

wherein $C^3$, $C^4$, $Q_1$, $Q_2$, bond a, $R^{P1}$, $R^{P2}$, $R_1$, $R_2$, $X_1$, $X_2$, $X_3$, $X_4$, B, B' and L each have any one of the meanings defined herein.

In an embodiment of the dinucleotides of Formula Ib:
$Q_1$ and $Q_2$ are as defined in any one of paragraphs (1) to (5) above;
$R^{P1}$ is as defined in any one of paragraphs (6) to (12) above;
$R^{P2}$ is as defined in any one of paragraphs (6) to (10) or (13) to (14) above;
$X_1$ and $X_2$ are as defined in any one of paragraphs (15) to (24) above;
bond a, $X_3$ and $X_4$ are as defined in any one of paragraphs (25) to (38) above;
$R^1$ and $R_2$ is as defined in any one of paragraphs (39) to (45) above; and
L is as defined in any one of paragraphs (49) to (55) above.

In another embodiment of the dinucleotides of Formula Ib:
$Q_1$ and $Q_2$ are as defined in paragraph (5) above;
$R^{P1}$ is as defined in paragraph (6) above;
$R^{P2}$ is as defined in paragraph (14) above;
$X_1$ and $X_2$ are as defined in paragraph (24) above;

bond a, $X_3$ and $X_4$ are as defined in any one of paragraphs (35) or (38) above;

$R^1$ and $R_2$ is as defined in paragraph (45) above; and

L is as defined in paragraph (55) above.

In another particular group of dinucleotides of the invention, the dinucleotide is of Formula (I), $Q_1$ and $Q_2$ are O, and $R^z$ is as shown below, i.e. the dinucleotides have the structural formula Ic (a sub-definition of Formula (I)) shown below:

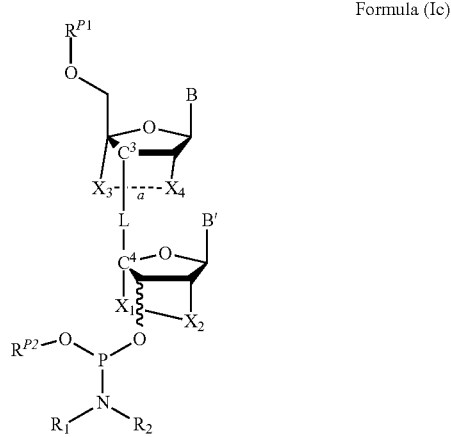

Formula (Ic)

wherein $C^3$, $C^4$, bond a, $R^{P1}$, $R^{P2}$, $R_1$, $R_2$, $X_1$, $X_2$, $X_3$, $X_4$, B, B' and L each have any one of the meanings defined herein.

In an embodiment of the dinucleotides of Formula Ic:

$R^{P1}$ is as defined in any one of paragraphs (6) to (12) above;

$R^{P2}$ is as defined in any one of paragraphs (6) to (10) or (13) to (14) above;

$X_1$ and $X_2$ are as defined in any one of paragraphs (15) to (24) above;

bond a, $X_3$ and $X_4$ are as defined in any one of paragraphs (25) to (38) above;

$R^1$ and $R_2$ is as defined in any one of paragraphs (39) to (45) above; and

L is as defined in any one of paragraphs (49) to (55) above.

In another embodiment of the dinucleotides of Formula Ic:

$R^{P1}$ is as defined in paragraph (6) above;

$R^{P2}$ is as defined in paragraph (14) above;

$X_1$ and $X_2$ are as defined in paragraph (24) above;

bond a, $X_3$ and $X_4$ are as defined in any one of paragraphs (35) or (38) above;

$R^1$ and $R_2$ is as defined in paragraph (45) above; and

L is as defined in paragraph (55) above.

In another particular group of dinucleotides of the invention, the dinucleotide is of Formula (I), $Q_1$ and $Q_2$ are O, and $R^z$ and $R^{P1}$ are as shown below, i.e. the dinucleotides have the structural formula Id (a sub-definition of Formula (I)) shown below:

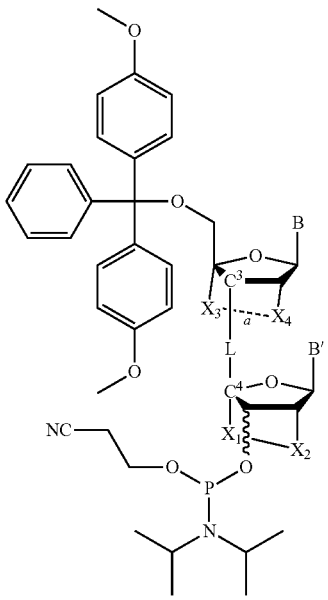

Formula (Id)

wherein $C^3$, $C^4$, bond a, $X_1$, $X_2$, $X_3$, $X_4$, B, B' and L each have any one of the meanings defined herein.

In an embodiment of the dinucleotides of Formula Id:

$X_1$ and $X_2$ are as defined in any one of paragraphs (15) to (24) above;

bond a, $X_3$ and $X_4$ are as defined in any one of paragraphs (25) to (38) above; and L is as defined in any one of paragraphs (49) to (55) above.

In another embodiment of the dinucleotides of Formula Id:

$X_1$ and $X_2$ are as defined in paragraph (24) above;

bond a, $X_3$ and $X_4$ are as defined in any one of paragraphs (35) or (38) above; and L is as defined in paragraph (55) above.

In another particular group of dinucleotides of the invention, the dinucleotide is of Formula (II) and $Q_1$ and $Q_2$ are oxygen, i.e. the dinucleotides have the structural formula IIa (a sub-definition of Formula (II)) shown below:

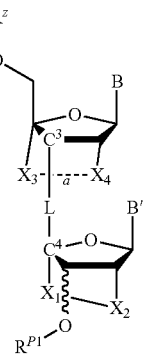

Formula IIa wherein $C^3$, $C^4$, bond a, $R^{P1}$, $R^z$, $X_1$, $X_2$, $X_3$, $X_4$, B, B' and L each have any one of the meanings defined herein.

an embodiment of the dinucleotides of Formula IIa:

$R^{P1}$ is as defined in any one of paragraphs (6) to (12) above;

$X_1$ and $X_2$ are as defined in any one of paragraphs (15) to (24) above;

bond a, $X_3$ and $X_4$ are as defined in any one of paragraphs (25) to (38) above;

$R^z$ is as defined in any one of paragraphs (39) to (48) above; and

L is as defined in any one of paragraphs (49) to (55) above.

In another embodiment of the dinucleotides of Formula IIa:

$R^{P1}$ is as defined in paragraph (12) above;

$X_1$ and $X_2$ are as defined in paragraph (24) above;

bond a, $X_3$ and $X_4$ are as defined in any one of paragraphs (35) or (38) above;

$R^z$ is as defined in paragraph (48) above; and

L is as defined in paragraph (55) above.

In another particular group of dinucleotides of the invention, the dinucleotide is of Formula (II), $Q_1$ and $Q_2$ are O, and $R^z$ and $R^{P1}$ are as shown below, i.e. the dinucleotides have the structural formula IIb (a sub-definition of Formula (II)) shown below:

Formula IIb

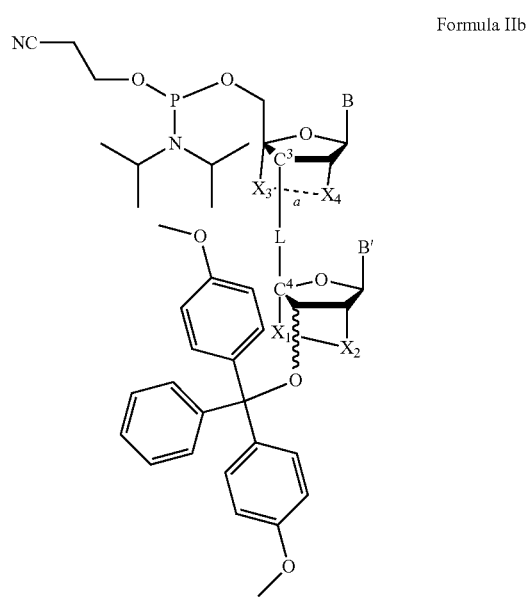

wherein $C^3$, $C^4$, bond a, $X_1$, $X_2$, $X_3$, $X_4$, B, B' and L each have any one of the meanings defined herein.

In an embodiment of the dinucleotides of Formula IIb:

$X_1$ and $X_2$ are as defined in any one of paragraphs (15) to (24) above;

bond a, $X_3$ and $X_4$ are as defined in any one of paragraphs (25) to (38) above; and L is as defined in any one of paragraphs (49) to (55) above.

In another embodiment of the dinucleotides of Formula IIb:

$X_1$ and $X_2$ are as defined in paragraph (24) above;

bond a, $X_3$ and $X_4$ are as defined in any one of paragraphs (35) or (38) above; and L is as defined in paragraph (55) above.

Particular dinucleotides of the present invention include any of the dinucleotides exemplified in the present application, and, in particular, any of the following:

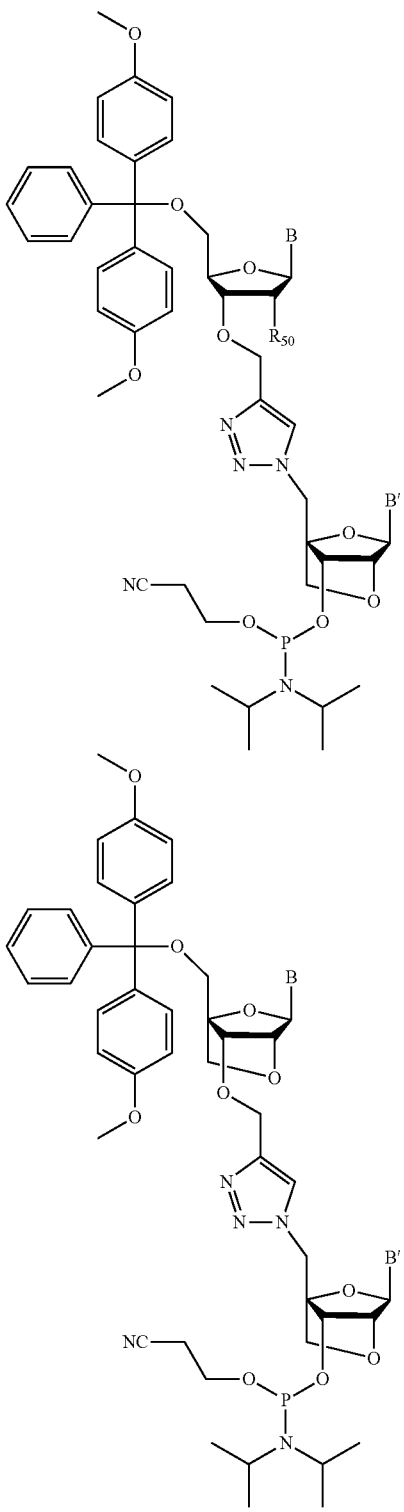

wherein B and B' are each independently a nucleobase and $R_{50}$ is selected from H, OH, $NH_2$, $OCH_3$ or F.

According to another aspect of the present invention, there is provided a dinucleotide of Formula III shown below:

Formula III

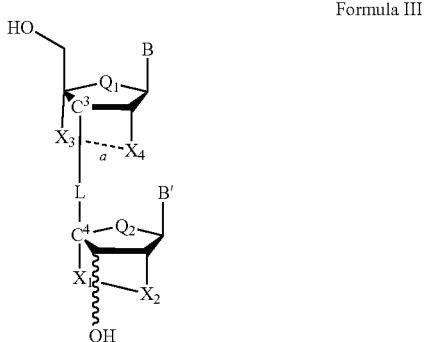

wherein bond a, $C^3$, $C^4$, $Q_1$, $Q_2$, B, $X_1$, $X_2$, $X_3$, $X_4$ and L are each as defined hereinabove.

It will be understood that features, including optional, suitable, and preferred features in relation to any one of the aspects of the present invention detailed above (i.e. the dinucleotides of Formula I or Formula II) may also be features, including optional, suitable and preferred features in relation to any other aspects of the invention (i.e. the dinucleotides of Formula III).

Synthesis

The dinucleotides of the present invention can be prepared by any suitable technique known in the art. Particular processes for the preparation of these dinucleotides are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the dinucleotides of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

The resultant dinucleotides of formula (I) or formula (II) may be isolated and purified using techniques well known in the art.

Uses and Applications

Dinucleotides of Formula (III) herein may be used therapeutically for the treatment of various diseases and disorders, such as cancer, genetic disorders and infection. Thus, in one aspect, the present invention provides a dinucleotide of formula (III) as defined herein for use in therapy.

In another aspect there is provided a method for the treatment of a disease or disorder, said method involving administering a therapeutically effective amount of a dinucleotide as defined herein, or a pharmaceutically acceptable salt or solvate thereof. In an embodiment, the disease or disorder is cancer. In a further embodiment, the disease or disorder is a genetic disorder. In another embodiment, the disease or disorder is an infection.

According to another aspect of the present invention, there is provided a method of preparing a target oligonucleotide as defined herein, the method comprising reacting a dinucleotide of formula (I) or (II) with one or more further nucleotides, dinucleotides and/or oligonucleotides. In an embodiment, the target oligonucleotide comprises more than one dinucleotide of formula (I) or (II). In an alternative embodiment, the target oligonucleotide is composed entirely of dinucleotide moieties formed by the reaction of a dinucleotide of formula (I) or (II) with other dinucleotides of formula (I) or (II) respectively.

Illustrative non-limiting examples of dinucleotides of formula (I) reacting with other nucleotides are shown in FIGS. 28 to 32 herein.

According to a further aspect of the present invention, there is provided an oligonucleotide prepared by the process defined above.

According to a further aspect of the present invention, there is provided the use of an oligonucleotide prepared by the process of the fourth aspect of the present invention as antisense RNA or interference RNA (RNAi, e.g. siRNA or miRNA) or an RNA component of a CRISPR-Cas system (e.g. crRNA, tracrRNA, gRNA).

According to another aspect of the present invention, there is provided the use of an oligonucleotide prepared by the process of the fourth aspect of the present invention as:
a template for amplification in a polymerase chain reaction (PCR):
as a template in a DNA replication process;
as a template in a transcription process to provide a corresponding RNA transcript, or as a template in a reverse transcription process to provide a corresponding DNA transcript;
as template in a translation process to produce a corresponding protein or peptide or to guide one or more proteins of interest to a target DNA or RNA.

Illustrative Examples of Oligonucleotides in CRISPR-Cas Systems

In general terms, there are two main classes of CRISPR-Cas systems (Makarova et al. *Nat Rev Microbiol.* 13:722-736 (2015)), which encompass five major types and 16 different subtypes based on cas gene content, cas operon architecture, Cas protein sequences, and process steps (Makarova et al. *Biol Direct.* 6:38 (2011); Makarova and Koonin *Methods Mol Biol.* 1311:47-75 (2015); Barrangou, R. *Genome Biology* 16:247 (2015)). This classification in either Class 1 or Class 2 is based upon the Cas genes involved in the interference stage.

Class 1 systems have a multi-subunit crRNA-effector complex such as Cascade-Cas3, whereas Class 2 systems have a crRNA-effector complex having a single Cas protein, such as Cas9, Cas12 (previously referred to as Cpf1) and Cas 13a (previously referred to as C2c2). For Type II systems there is a second RNA component tracrRNA which hybridises to crRNA to form a crRNA:tracr RNA duplex, these two RNA components may be linked to form single guide RNA.

RNA components in such CRISPR-Cas systems may be adapted to be an oligonucleotide in accordance with the invention or a dinucleotide of the invention may be comprised within an RNA components of a CRISPR-Cas system. It would be a matter of routine for a person of ordinary skill in the art to synthesise a crRNA, pre-crRNA, tracrRNA or guideRNA comprising a dinucleotide of the invention or having at least one inter-nucleoside linkage which is a triazole linker moiety between two nucleosides with a locked nucleoside positioned at the 3' end of the triazole linker moiety, and which retains the desired function of the RNA component (e.g., to guide the crRNA:effector complex to a target site). Standard methods are known in the art for testing whether oligonucleotides of the invention when used as such CRISPR RNA components retain the desired function (e.g. by comparing the desired function to that of a control CRISPR RNA component which has the same nucleosides without any-triazole linker moieties between nucleosides or locked nucleosides).

The term "CRISPR RNA components" or "RNA component of a CRISPR-Cas system" is used herein, as in most CRISPR-Cas systems, the nucleic acid sequences which guide the effector protein(s) to a desired target sequence are RNA components. However, CRISPR hybrid DNA/RNA polynucleotides which can also function to guide effector protein(s) to a desired target site in a DNA or RNA sequence are also known in the art—see for example Rueda et al. (Mapping the sugar dependency for rational generation of a DNA-RNA hybrid-guided Cas9 endonuclease, Nature Communications 8, Article Number: 1610 (2017)). Accordingly, reference to CRISPR RNA components herein may also encompass hybrid RNA/DNA components such as crDNA/RNA, tracrDNA/RNA or gDNA/RNA.

Advantageously the oligonucleotides of the invention may have particular utility in in vivo gene therapy applications. For example, one way of carrying out in vivo therapy using a Type II CRISPR-Cas system involves delivering the Cas9 and tracrRNA via a virus, which can assemble inactive complexes inside of cells. The crRNA can then be administered later to assemble and selectively activate CRISPR/Cas9 complexes, which would then go on to target and edit specific sites in the human genome, such as disease relevant genes (Gagnon and Corey, Proc. Natl. Acad. Sci. USA 112:15536-15537, 2015; Randar, et al, Proc. Natl. Acad. Sci. USA 112:E7110-71 17, 2015). For this gene therapy approach to work the crRNA should be extremely resistant to nucleases and cellular degradation, as well as confer high activity and specificity to the assembled CRISPR/Cas9 complex. Hence, the increased stability of the oligonucleotides of the invention to degradation is highly desirable. Alternatively, crRNA:effector complexes (i.e. CRISPR-Cas complexes, such as CRISPR/Cas9) can be assembled in vitro and directly transfected into cells for genome editing (Liang, et al, J. Biotechnol. 208:44-53, 2015; Zuris, et al, Nat. Biotechnol. 33:73-80, 2015). Special transfection reagents, such as CRISPRMAX (Yu, et al, Biotechnol. Lett. 38:919-929, 2016), have been developed for this purpose. Oligonucleotides of the invention when used as crRNAs may improve this approach by offering stability against degradation.

Accordingly, the oligonucleotides of the invention when used as CRISPR RNA components can advantageously be used for the various applications of CRISPR-Cas systems known in the art including: gene-editing, gene activation (CRISPRa) or gene interference (CRISPRi), base-editing, multiplex engineering (CRISPRm), DNA amplification, diagnostics (e.g. SKERLOCK or DETECTR), cell recording (e.g. CAMERA), typing bacteria, antimicrobial applications, synthesising new chemicals etc.

Suitably, in diagnostic applications such as SHERLOCK and DETECTR the oligonucleotides of the invention can be used as RNA components such as the "sacrificial RNA molecules" used to create a signal.

EXAMPLES

In this section, ON is an abbreviation for oligonucleotide.

General Synthetic Procedures

All reagents were purchased from Sigma-Aldrich, Alfa Aesar, Fisher Scientific, or Link Technologies and used without further purification. Pyridine (from KOH) and POCl$_3$ were freshly distilled before use, and THF was obtained using the MBraun SPS Bench Top solvent purification system (SPS). All air/moisture sensitive reactions were carried out under inert atmosphere (argon) in oven-dried glassware. Reactions were monitored by thin layer chromatography (TLC) using Merck Kieselgel 60 F24 silica gel plates (0.22 mm thickness, aluminium backed). The compounds were visualized by UV irradiation at 254/265 nm and by staining in p-anisaldehyde solution. Column chromatography was carried out under pressure (Flash Master Personal) using Biotage Isolute SPE columns. Columns were primed with CH$_2$Cl$_2$ containing 1% pyridine prior to use. $^1$H and $^{13}$C spectra were measured on a Bruker AVII 500 spectrometer at 500 MHz and 126 MHz, respectively. Chemical shifts are given in ppm and were internally referenced to the appropriate residual solvent signal, all coupling constants (J) are quoted in Hertz (Hz). Assignment of compounds was aided by COSY, HSQC, HMBC, and DEPT-135 experiments. High-resolution mass spectra were measured on a Bruker 9.4 FT-ICR-MS mass spectrometer, and samples were run in MeOH.

Synthesis of 5'-azido LNA (100)

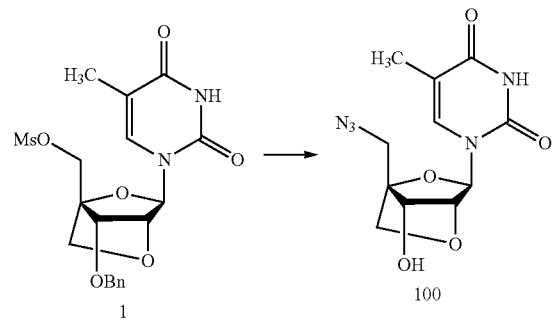 [SMILES: Cc1cn([C@@H]2O[C@@]3(COS(C)(=O)=O)COC2[C@H]3OCc2ccccc2)c(=O)[nH]c1=O ; Cc1cn([C@@H]2O[C@@]3(CN=[N+]=[N-])COC2[C@H]3O)c(=O)[nH]c1=O]

To a solution of nucleoside 1 (prepared according to Koshkin et al., *J. Org. Chem.* (2010), 66, 8504-8512) (1.0 g, 2.28 mmol) in MeOH (15 mL) was added Pd(OH)$_2$/C (20% wt % loading, 200 mg). The mixture was degassed with argon (5 min) and then with hydrogen (10 min). The reaction mixture was stirred under hydrogen at room temperature for 16 h. Catalyst was filtered off and the filter cake was washed with MeOH (50 mL). Filtrate was concentrated under reduced pressure and the residue was dissolved in DMF (10 mL). NaN$_3$ (300 mg, 4.61 mmol) was added and the reaction mixture was stirred at 90° C. for 2 h. Solvent was removed at reduced pressure and residue was purified using column chromatography (0 to 7% MeOH in CH$_2$Cl$_2$) to afford 5'-azido LNA 100 (0.43 g, 64%) as white foam. R$_f$ (0.5, 7% MeOH in CH$_2$Cl$_2$). $^1$H NMR (500 MHz, DMSO) δ 11.40 (s, 1H), 7.48 (d, J=1.2 Hz, 1H), 5.88 (bs, 1H), 5.48 (s, 1H), 4.20 (s, 1H), 3.99 (d, J=14.0 Hz, 1H), 3.92 (s, 1H), 3.88 (d, J=8.0 Hz, 1H), 3.79 (d, J=14.0 Hz, 1H), 3.74 (d, J=8.0 Hz, 1H), 1.82 (d, J=1.2 Hz, 3H). $^{13}$C NMR (126 MHz, DMSO) δ 164.2, 150.4, 134.8, 109.2, 87.4, 87.1, 79.5, 71.6, 70.4, 47.9, 12.8.

Synthesis of 5'-O-(4,4'-dimethoxytrityl)-3'-O-propargyl-LNA Thymidine (3)

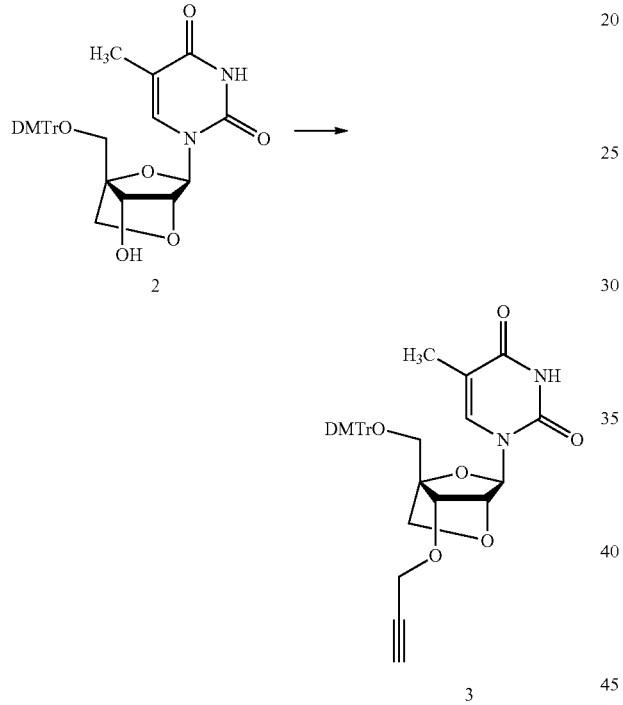

Nucleoside 2 (prepared according to Obika et al., *Bioorg. Med. Chem.* (2001), 9, 1001-1011) (2.00 g, 3.50 mmol) was co-evaporated with anhydrous THF (3×15 mL) and re-dissolved in anhydrous THF (24 mL). The solution was cooled to 0° C. and NaH (60% suspension in mineral oil, 0.348 g, 14.5 mmol) was added in portions over 5 min. The reaction mixture was stirred on ice for 30 min and at room temperature for 1 h. Propargyl bromide (0.374 mL, 4.20 mmol) was added at 0° C. and the reaction was stirred on ice for 30 min and at room temperature for 16 h. Solvent was removed at reduced pressure and the residue was dissolved in EtOAc (100 mL) and washed with brine (2×50 mL). The organic phase was dried (Na$_2$SO$_4$) and concentrated and the resulting crude was purified using column chromatography (EtOAc in hexane, 10% to 80%, v/v) to obtain compound 3 (1.68 g, 2.75 mmol, 79%) as a white foam. R$_f$=0.4 (70% EtOAc in hexane, v/v). ESI HRMS m/z 633.2208 ([M+Na]$^+$, C$_{35}$H$_{34}$O$_8$N$_2$Na$^+$ calc. 633.2207. $^1$H NMR (500 MHz, DMSO-d$_6$) δ 11.47 (s, 1H, NH), 7.59 (d, J=1.1 Hz, 1H, H-6), 7.46-7.45 (m, 2H, DMTr), 7.36-7.31 (m, 6H, DMTr), 7.28- 7.25 (m, 1H, DMTr), 6.93 (d, J=8.8 Hz, 4H, DMTr), 5.52 (s, 1H, H-1'), 4.60 (s, 1H, H-2'), 4.37-4.32 (m, 2H, H-3', CH$_2$—C≡CH), 4.29 (dd, J=15.9, 2.4 Hz, 1H, CH$_2$—C≡CH), 3.75 (s, 6H, OCH$_3$), 3.72-3.70 (d, J=8.0 Hz, 1H, H-5"), 3.69-3.68 (d, J=8.0 Hz, 1H, H-5"), 3.58 (t, J=2.4 Hz, 1H, C≡CH), 3.39 (d, J=11.8 Hz, 1H, H-5'), 3.36-3.34 (m, 1H, H-5', merged with H$_2$O signal from DMSO-d$_6$), 1.56 (d, J=1.1 Hz, 3H, CH$_3$). $^{13}$C NMR (126 MHz, DMSO) δ 164.3 (C4), 158.7 (DMTr), 150.3 (C2), 145.0, 135.6, 135.4 (DMTr), 134.5 (C6), 130.25, 130.18, 128.5, 128.1, 127.3, 113.8 (DMTr), 109.1 (C5), 87.1 (C4'), 87.0 (C1'), 86.3 (DMTr), 80.2 (C≡CH), 78.6 (C≡CH), 76.5 (C2'), 75.8 (C3'), 72.1 (C5"), 58.4 (C5'), 57.4 (CH$_2$—C≡CH), 55.5 (OCH$_3$), 12.9 (CH$_3$).

Synthesis of 5'-O-(4,4'-dimethoxytrityl)-3'-O-propargyl-5-methyl LNA Cytidine (4)

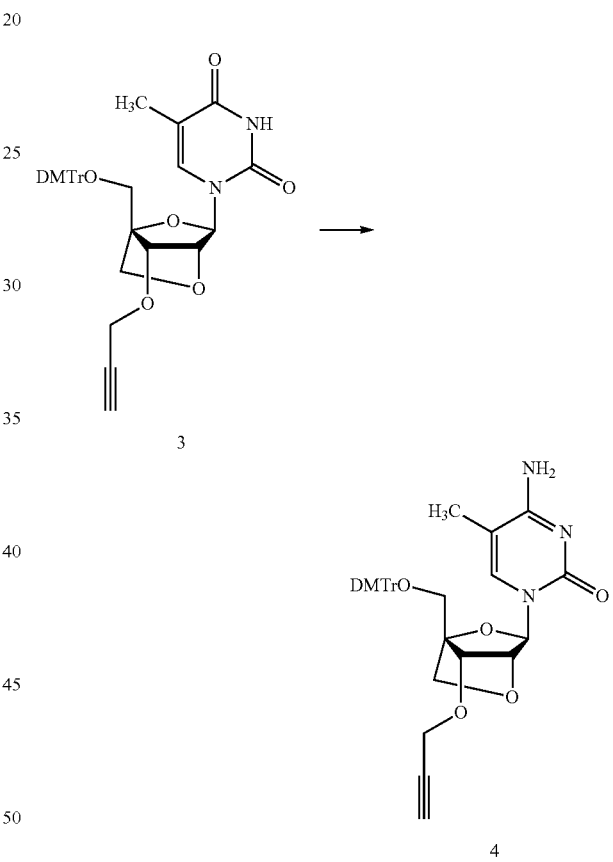

Nucleoside 3 (0.408 g, 0.668 mmol) was co-evaporated with anhydrous pyridine (3×10 mL) and re-dissolved in anhydrous pyridine (5 mL). The solution was cooled to 0° C. and N-methylimidazole (0.7 mL, 8.8 mmol) was added. The reaction mixture was stirred at 0° C. for 15 min, whereupon a freshly distilled POCl$_3$ (0.25 mL, 2.7 mmol) was added dropwise. The reaction was stirred at 0° C. for 30 min and then at room temperature for an additional 30 min Concentrated aqueous ammonia (5 mL) was added and the reaction was stirred at room temperature for 16 h. The solvents were removed under reduced pressure. The residue was dissolved in CH$_2$Cl$_2$ (50 mL) and washed with brine (2×30 mL). The aqueous phase was back extracted with CH$_2$Cl$_2$ (2×30 mL). The combined organic phase was dried (Na$_2$SO$_4$), and concentrated under reduced pressure. The crude was then purified using column chromatography (0% to 7% MeOH/CH$_2$Cl$_2$) to obtain nucleoside 4 (0.233 g, 0.382 mmol, 57%) as a white foam. R$_f$=0.5 (8% MeOH in CH$_2$Cl$_2$, v/v). ESI HRMS m/z 608.2406 ([M−H]$^−$, C$_{35}$H$_{34}$O$_7$N$_3$$^−$ calc. 608.2402. $^1$H NMR (500 MHz, DMSO-d$_6$) δ 7.57 (s, 1H, H-6), 7.47-7.45 (m, 2H, DMTr), 7.41 (broad s, 1H, N—H), 7.37-7.31 (m, 6H, DMTr), 7.28-7.25 (m, 1H, DMTr), 6.93 (d, J=8.8 Hz, 4H, DMTr), 6.85 (broad s, 1H, NH), 5.50 (s, 1H, H-1'), 4.56 (s, 1H, H-2'), 4.34-4.30 (m, 2H, H-3', C<u>H</u>$_2$—C≡CH), 4.25 (dd, J=16.0 Hz, 2.4 Hz, 1H, C<u>H</u>$_2$—C≡CH), 3.75 (s, 6H, OCH$_3$), 3.68 (s, 2H, H-5"), 3.56 (t, J=2.4 Hz, 1H, C≡CH), 3.36 (s, 2H, H-5', merged with H$_2$O signal from DMSO-d$_6$), 1.62 (s, 3H, CH$_3$). $^{13}$C NMR (126 MHz, DMSO) δ 166.0 (C4), 158.7 (DMTr), 155.1 (C2), 144.9 (DMTr), 136.8 (C6), 135.7, 135.5, 130.25, 130.18, 128.5, 128.2, 127.3, 113.83, 113.81 (DMTr), 101.4 (C5), 87.5 (C1'), 86.8 (C4'), 86.3 (DMTr), 80.1 (<u>C</u>≡CH), 78.6 (C≡<u>C</u>H), 76.5 (C2'), 75.5 (C3'), 72.0 (C5"), 58.5 (C5'), 57.4 (<u>CH$_2$</u>—C≡CH), 55.5 (OCH$_3$), 14.0 (CH$_3$).

Synthesis of N6-benzoyl-5'-O-(4,4'-dimethoxytrityl)-3'-O-propargyl-5-methyl-LNA Cytidine (101)

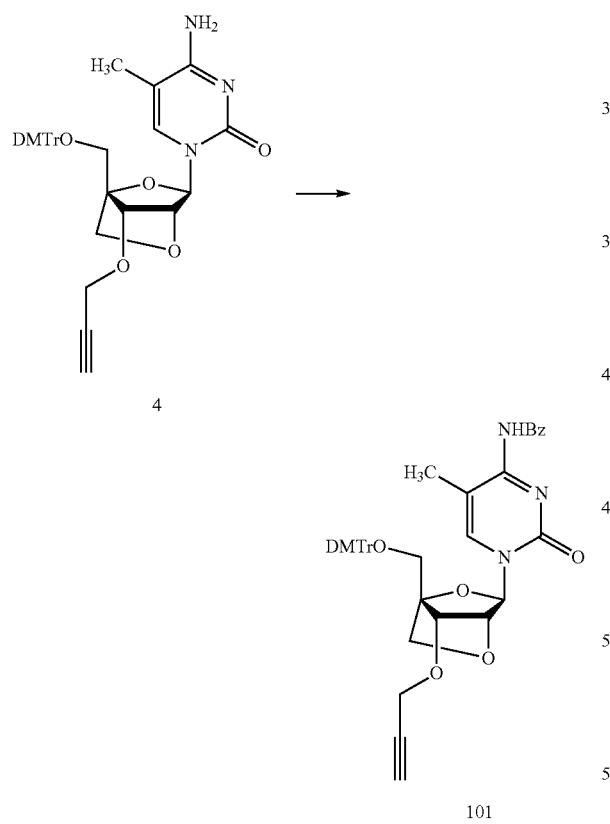

101

To a solution of nucleoside 4 (0.74 g, 1.21 mmol) in DMF (5 mL) was added benzoic anhydride (0.41 g, 1.81 mmol). The reaction mixture was stirred at room temperature for 18 h. Solvent was removed and residue was taken up in EtOAc (100 mL), washed with sat. aqueous NaHCO$_3$ (50 mL), brine (2×50 mL), dried (Na$_2$SO$_4$) and concentrated. The crude mixture was purified using column chromatography (0 to 50% EtOAc in hexane) to obtain 101 (0.75 g, 86%) as a white foam. R$_f$ (0.4, 40% EtOAc in hexane). ESI HRMS m/z 712.2663 ([M−H]$^−$, C$_{42}$H$_{38}$O$_8$N$_3$$^−$ calc. 712.2664. $^1$H NMR (400 MHz, DMSO) δ 13.14 (bs, 1H), 8.18 (s, 2H), 7.86 (s, 1H), 7.62-7.59 (m, 1H), 7.53-7.47 (m, 4H), 7.39-7.34 (m, 6H), 7.29-7.26 (m, 1H), 6.96-6.93 (m, 4H), 5.60 (s, 1H), 4.69 (s, 1H), 4.40 (s, 1H), 4.36 (dd, J=16.0 Hz, 2.4 Hz, 1H), 4.30 (dd, J=16.0 Hz, 2.4 Hz, 1H), 3.76 (s, 6H), 3.74-3.72 (m, 2H), 3.57 (t, J=2.4 Hz, 1H), 3.44 (d, J=11.2 Hz, 1H), 3.38 (d, J=11.2 Hz, 1H). 1.81 (s, 3H).

Synthesis of N6-benzoyl-5'-O-(4,4'-dimethoxytrityl)-3'-O-propargyl-5-methyl-2'-deoxycytidine (102)

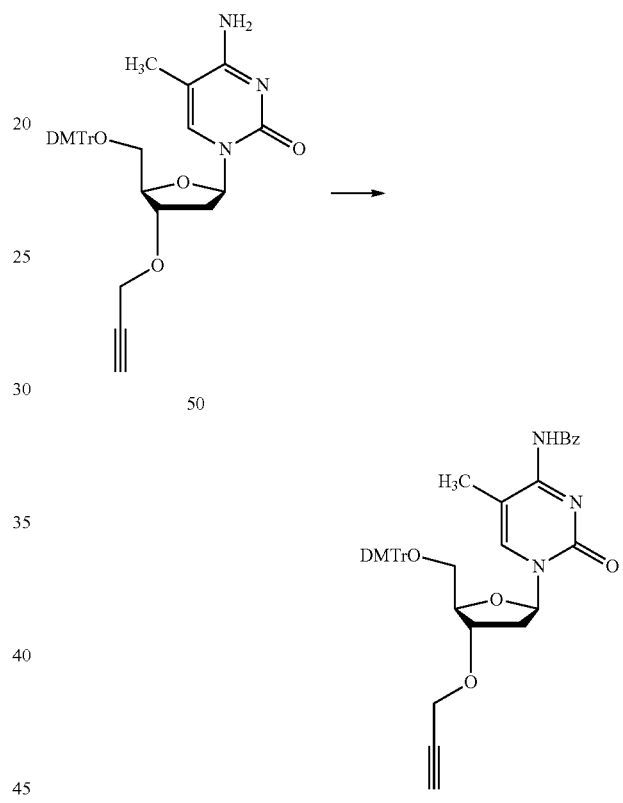

102

To a solution of nucleoside 50 (prepared according to El-Sagheer & Brown, *Proc. Natl. Acad. Sci.* USA, (2010), 107, 15329-15334) (1.20 g, 2.00 mmol) in DMF (5 mL) was added benzoic anhydride (0.93 g, 4.11 mmol). The reaction mixture was stirred at room temperature for 20 h. Solvent was removed and residue was taken up in EtOAc (100 mL), washed with sat. aqueous NaHCO$_3$ (50 mL), brine (2×50 mL), dried (Na$_2$SO$_4$) and concentrated. The crude mixture was purified using column chromatography (0 to 50% EtOAc in hexane) to obtain 102 (1.30 g, 92%) as a white foam. R$_f$ (0.5, 50% EtOAc in hexane). $^1$H NMR (400 MHz, DMSO) δ 12.93 (bs, 1H), 8.16 (d, J=7.6 Hz, 2H), 7.82 (s, 1H), 7.63-7.58 (m, 1H), 7.52-7.48 (m, 2H), 7.43-7.40 (m, 2H), 7.37-7.23 (m, 7H), 6.94-6.90 (m, 4H), 6.15 (t, J=6.8 Hz, 1H), 4.51-4.48 (m, 1H), 4.24 (t, J=2.3 Hz, 2H), 4.12 (t, J=3.6 Hz, 1H), 3.74 (s, 6H), 3.53 (t, J=2.3 Hz, 2H), 3.33-3.29 (m, 1H), 3.23 (dd, J=10.6 Hz, 3.5 Hz, 1H), 2.48-2.44 (m, 1H), 2.42-2.35 (m, 1H), 1.81 (s, 3H).

Synthesis of DNA/DNA Triazole Nucleoside (60)

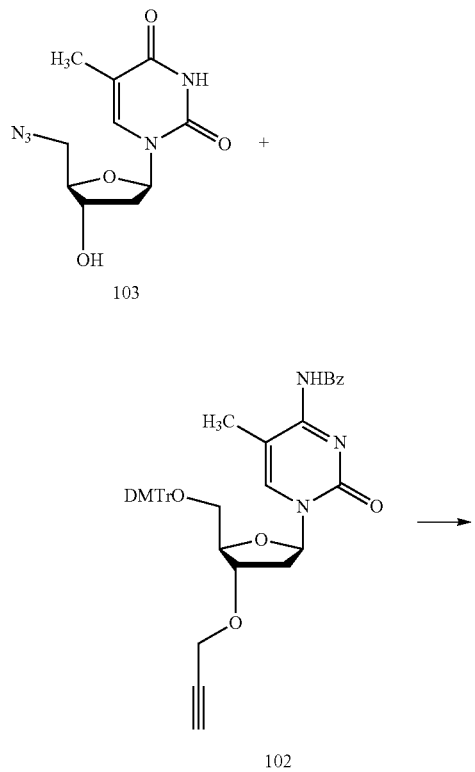

mixture was degassed with argon and stirred at room temperature for 2 h. Reaction was diluted with EtOAc (100 mL), washed with H$_2$O (50 mL) and sat. aqueous solution of EDTA (3×50 mL). The combined aqueous phase was back extracted with EtOAc (50 mL) and the combined organic phase was dried (Na$_2$SO$_4$) and concentrated under reduced pressure. The residue was purified using column chromatography (0-6% MeOH in CH$_2$Cl$_2$) to obtain 60 (0.50 g, 80%) as a white foam. R$_f$ (0.4, 6% MeOH in CH$_2$Cl$_2$). ESI HRMS m/z 953.3824 ([M+H]$^+$, C$_{51}$H$_{53}$O$_{11}$N$_8$$^+$ calc. 953.3828. $^1$H NMR (500 MHz, DMSO) δ 12.97 (s, 1H), 11.32 (s, 1H), 8.19 (d, J=7.2 Hz, 2H), 8.10 (s, 1H), 7.82 (s, 1H), 7.60 (t, J=7.0 Hz, 1H), 7.50 (t, J=7.8 Hz, 2H), 7.40-7.39 (m, 2H), 7.35-7.32 (m, 3H), 7.28-7.24 (m, 5H), 6.93-6.91 (m, 4H), 6.18-6.15 (m, 2H), 5.52 (d, J=4.4 Hz, 1H), 4.71 (dd, J=14.2 Hz, 4.4 Hz, 1H), 4.63-4.56 (m, 3H), 4.46-4.44 (m, 1H), 4.31-4.27 (m, 1H), 4.13 (s, 1H), 4.10-4.06 (m, 1H), 3.76 (s, 6H), 3.31 (dd, J=9.8 Hz, 4.4 Hz, 1H), 3.23-3.22 (m, 1H), 2.46-2.42 (m, 2H), 2.22-2.17 (m, 1H), 2.13-2.09 (m, 1H), 1.79 (s, 3H), 1.68 (s, 3H). $^{13}$C NMR (126 MHz, DMSO) δ 178.6, 164.1, 159.2, 158.7, 150.8, 147.9, 145.1, 144.2, 138.6, 137.1, 136.5, 135.8, 135.6, 133.2, 130.2, 129.9, 128.8, 128.5, 128.1, 127.3, 125.2, 113.8, 110.7, 110.3, 86.6, 85.4, 84.5, 84.4, 83.8, 78.9, 71.2, 64.0, 62.3, 55.5, 51.6, 38.4, 37.4, 13.0, 12.5.

Synthesis of DNA/LNA Triazole Nucleoside (70)

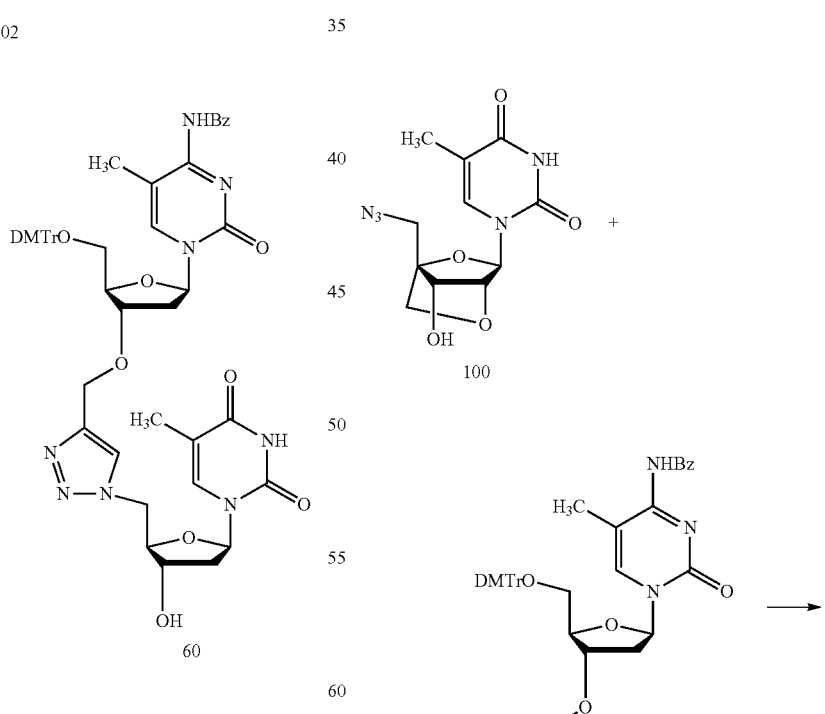

Nucleosides 103 (prepared according to Said et al., *Synlett*, (2012), 23, 2923-2926) (175 mg, 0.66 mmol) and 102 (0.50 g, 0.73 mmol) were dissolved in THF:H$_2$O:t-BuOH (10 mL, 3:1:1, v/v/v). To this solution was added pyridine (2-3 drops), CuSO$_4$ (1.5 mL, 7.5% aqueous, w/v), and sodium ascorbate (1.7 mL, 1M aqueous). The reaction -continued

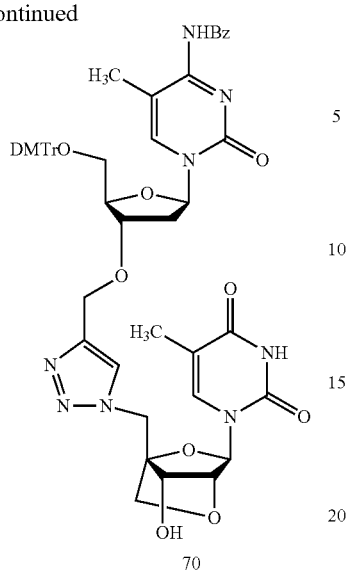

70

Nucleosides 100 (237 mg, 0.80 mmol) and 102 (0.60 g, 0.88 mmol) were dissolved in THF:H$_2$O:t-BuOH (10 mL, 3:1:1, v/v/v). To this solution was added pyridine (2-3 drops), CuSO$_4$ (1.8 mL, 7.5% aqueous, w/v), and sodium ascorbate (2.0 mL, 1M aqueous). The reaction mixture was degassed with argon and stirred at room temperature for 2 h. Reaction was diluted with EtOAc (100 mL), washed with H$_2$O (50 mL) and sat. aqueous solution of EDTA (3×50 mL). The combined aqueous phase was back extracted with EtOAc (50 mL) and the combined organic phase was dried (Na$_2$SO$_4$) and concentrated under reduced pressure. The residue was purified using column chromatography (0 to 6% MeOH in CH$_2$Cl$_2$) to obtain 70 (0.65 g, 82%) as a white foam. R$_f$ (0.4, 6% MeOH in CH$_2$Cl$_2$). ESI HRMS m/z 979.3717 ([M−H]$^-$, C$_{52}$H$_{51}$O$_{12}$N$_8^-$ calc. 979.3631. $^1$H NMR (500 MHz, DMSO) δ 12.36 (s, 1H), 11.94 (s, 1H), 8.21-8.18 (m, 3H), 7.82 (s, 1H), 7.60 (t, J=7.4 Hz, 1H), 7.50 (t, J=7.6 Hz, 2H), 7.41-7.31 (m, 2H), 7.34 (t, J=7.8 Hz, 2H), 7.29-7.13 (m, 5H), 6.92 (d, J=8.8 Hz, 4H), 6.60 (s, 1H), 6.16 (t, J=6.7 Hz, 1H), 6.07 (s, 1H), 5.40 (s, 1H), 4.99 (d, J=15.1 Hz, 1H), 4.88 (d, J=15.1 Hz, 1H), 4.66 (d, J=12.0 Hz, 1H), 4.62 (d, J=12.0 Hz, 1H), 4.47-4.45 (m, 1H), 4.18 (s, 1H), 41.4-4.12 (m, 1H), 4.03 (d, J=8.0 Hz, 1H), 3.79 (s, 1H), 3.74 (s, 6H), 3.59 (d, J=8.0 Hz, 1H), 3.32-3.29 (m, 1H), 3.25-3.22 (m, 1H), 2.47-2.41 (m, 2H), 1.67 (s, 6H). $^{13}$C NMR (126 MHz, DMSO) δ 164.1, 158.7, 158.6, 150.2, 145.1, 144.3, 135.8, 135.6, 134.1, 133.0, 130.19, 130.16, 129.8, 128.8, 128.5, 128.1, 127.3, 126.3, 113.8, 109.1, 87.1, 86.6, 86.3, 83.9, 79.5, 79.0, 64.0, 62.4, 55.5, 46.5, 39.7, 12.5.

Synthesis of LNA/DNA Triazole Nucleoside (80)

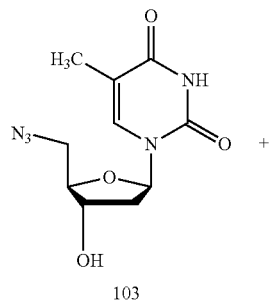

103

-continued

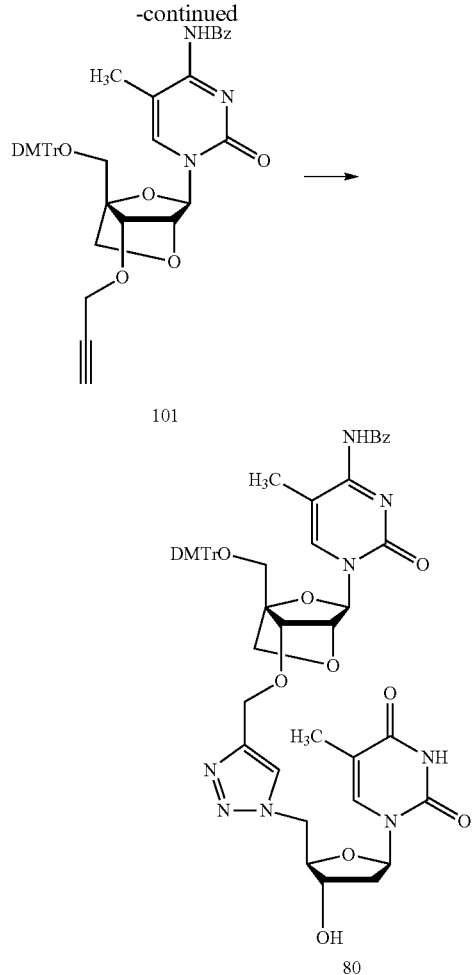

Nucleosides 103 (170 mg, 0.66 mmol) and 101 (0.50 g, 0.73 mmol) were dissolved in THF:H$_2$O:t-BuOH (10 mL, 3:1:1, v/v/v). To this solution was added pyridine (2-3 drops), CuSO$_4$ (1.5 mL, 7.5% aqueous, w/v), and sodium ascorbate (1.7 mL, 1M aqueous). The reaction mixture was degassed with argon and stirred at room temperature for 2 h. Reaction was diluted with EtOAc (100 mL), washed with H$_2$O (50 mL) and sat. aqueous solution of EDTA (3×50 mL). The combined aqueous phase was back extracted with EtOAc (50 mL) and the combined organic phase was dried (Na$_2$SO$_4$) and concentrated under reduced pressure. The residue was purified using column chromatography (0 to 6% MeOH in CH$_2$Cl$_2$) to obtain 80 (0.54 g, 87%) as a white foam. R$_f$ (0.5, 7% MeOH in CH$_2$Cl$_2$). ESI HRMS m/z 979.3621 ([M−H]$^-$, C$_{52}$H$_{51}$O$_{12}$N$_8^-$ calc. 979.3631. $^1$H NMR (500 MHz, DMSO) δ 13.17 (s, 1H), 11.31 (s, 1H), 8.23 (s, 2H), 8.03 (s, 1H), 7.85 (s, 1H), 7.61 (t, J=7.6 Hz, 1H), 7.52 (t, J=7.6 Hz, 2H), 7.42-7.42 (m, 2H), 7.34-7.23 (m, 8H), 6.93-6.90 (m, 4H), 6.16 (t, J=7.0 Hz, 1H), 5.60 (s, 1H), 5.50 (d, J=4.3 Hz, 1H), 4.72 (d, J=12.0 Hz, 1H), 4.68-4.64 (m, 3H), 4.58 (dd, J=14.3 Hz, 7.6 Hz, 1H), 4.41 (s, 1H), 4.29-4.25 (m, 1H), 4.07-4.04 (m, 1H), 3.75-3.71 (m, 7H), 3.41 (d, J=11.2 Hz, 1H), 3.36-3.31 (m, 2H, merged with H$_2$O signal from DMSO), 2.21-2.15 (m, 1H), 2.12-2.07 (m, 1H), 1.86 (s, 3H), 1.76 (s, 3H). $^{13}$C NMR (126 MHz, DMSO) δ 178.7, 164.1, 159.7, 158.65, 158.63, 150.8, 147.5, 145.0, 143.9, 137.4, 137.2, 136.5, 135.7, 135.4, 133.0, 130.2, 130.1, 129.8, 128.8, 128.5, 128.0, 127.3, 125.2, 113.8, 110.3, 109.9, 87.6, 87.4, 86.3, 84.5, 84.4, 76.6, 76.5, 72.2, 71.2, 63.1, 58.4, 55.5, 51.7, 38.4, 14.0, 12.5.

Synthesis of LNA/LNA Triazole Nucleoside (90)

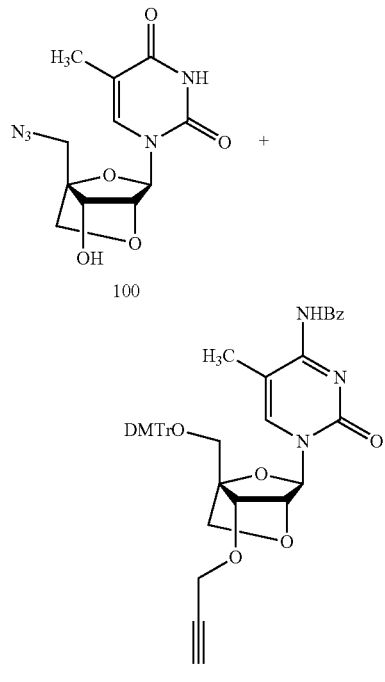

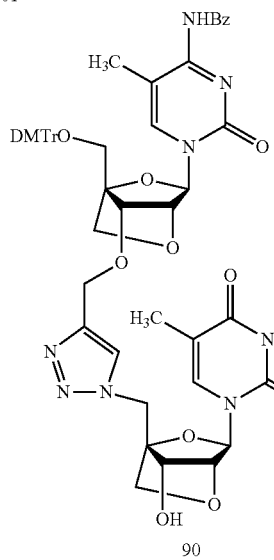

Nucleosides 100 (120 mg, 0.40 mmol) and 101 (0.36 g, 0.50 mmol) were dissolved in THF:H$_2$O:t-BuOH (5 mL, 3:1:1, v/v/v). To this solution was added pyridine (2-3 drops), CuSO$_4$ (0.9 mL, 7.5% aqueous, w/v), and sodium ascorbate (1.0 mL, 1M aqueous). The reaction mixture was degassed with argon and stirred at room temperature for 2 h. Reaction was diluted with EtOAc (50 mL), washed with H$_2$O (30 mL) and sat. aqueous solution of EDTA (3×30 mL). The combined aqueous phase was back extracted with EtOAc (20 mL) and the combined organic phase was dried (Na$_2$SO$_4$) and concentrated under reduced pressure. The residue was purified using column chromatography (0 to 6% MeOH in CH$_2$Cl$_2$) to obtain 90 (0.32 g, 79%) as a white foam. R$_f$ (0.4, 6% MeOH in CH$_2$Cl$_2$. ESI HRMS m/z 1009.3721 ([M+H]$^+$, C$_{53}$H$_{53}$O$_{13}$N$_8$$^+$ calc. 1009.3726. $^1$H NMR (400 MHz, DMSO) δ 13.22 (s, 1H), 11.39 (s, 1H), 8.24 (s, 2H), 8.18 (s, 1H), 7.92 (s, 1H), 7.65 (t, J=7.5 Hz, 1H), 7.55 (t, J=7.5 Hz, 2H), 7.48-7.46 (m, 2H), 7.40-7.27 (m, 8H), 6.97-6.93 (m, 4H), 6.67 (s, 1H), 6.11 (d, J=4.2 Hz, 1H), 5.65 (s, 1H), 5.45 (s, 1H), 5.02 (d, J=15.2 Hz, 1H), 4.87 (d, J=15.2 Hz, 1H), 4.82 (d, J=12.1 Hz, 1H), 4.75-4.71 (m, 2H), 4.48 (s, 1H), 4.21 (s, 1H), 4.03 (d, J=8.0 Hz, 1H), 3.85 (d, J=4.2 Hz, 1H), 3.79-3.76 (m, 7H), 3.55 (d, J=8.0 Hz, 1H), 3.47-3.43 (m, 2H), 1.90 (s, 3H), 1.65 (s, 3H).

Synthesis of DNA/DNA Triazole Phosphoramidite (10)

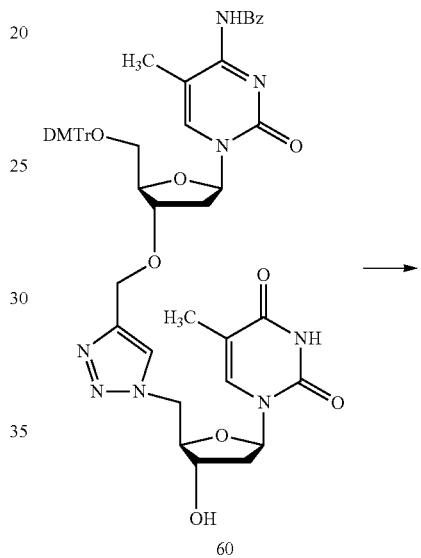

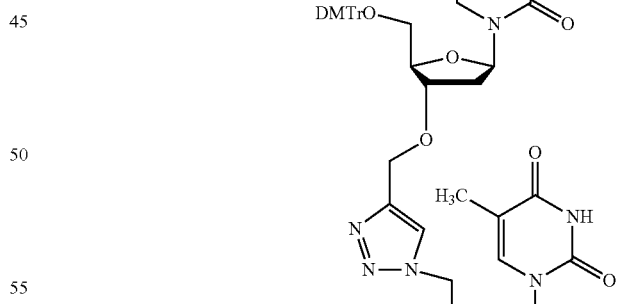

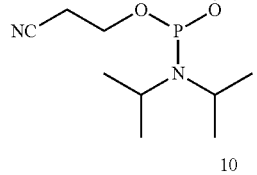

Nucleoside 60 (250 mg, 0.26 mmol) was dissolved in dry $CH_2Cl_2$ (5 mL). DIPEA (200 μL, 1.14 mmol) and 2-cyanoethyl N,N-diisopropylchlorophosphoramidite, (120 μL, 0.56 mmol), were added and reaction mixture was stirred at room temperature for 2 h. Reaction was diluted with $CH_2Cl_2$ (30 mL) and washed with sat. aqueous KCl (30 mL). The organic phase was dried ($Na_2SO_4$) and concentrated under reduced pressure. The residue was purified using column chromatography (0 to 3% MeOH in $CH_2Cl_2$) to obtain 10 (150 mg, 50%) as a white foam. $R_f$ (0.4, 3% MeOH in $CH_2Cl_2$). ESI HRMS m/z 1153.4915 ($[M+H]^+$, $C_{60}H_{70}O_{12}N_{10}P^+$ calc. 1153.4906. $^{31}P$ NMR (126 MHz, $CD_3CN$) δ 148.76, 148.53.

Nucleoside 70 (300 mg, 0.31 mmol) was dissolved in dry $CH_2Cl_2$ (5 mL). DIPEA (0.22 mL, 1.24 mmol) and 2-cyanoethyl N,N-diisopropylchlorophosphoramidite, (0.14 mL, 0.62 mmol), were added and reaction mixture was stirred at room temperature for 2 h. Reaction was diluted with $CH_2Cl_2$ (30 mL) and washed with sat. aqueous KCl (30 mL). The organic phase was dried ($Na_2SO_4$) and concentrated under reduced pressure. The residue was purified using column chromatography (0 to 3% MeOH in $CH_2Cl_2$) to obtain 11 (225 mg, 62%) as a white foam. $R_f$ (0.5, 4% MeOH in $CH_2Cl_2$). ESI HRMS m/z 1181.4861 ($[M+H]^+$, $C_{61}H_{70}O_{13}N_{10}P^+$ calc. 1181.4856. $^{31}P$ NMR (126 MHz, $CD_3CN$) δ 149.22, 148.86.

Synthesis of DNA/LNA Triazole Phosphoramidite (11)

Synthesis of LNA/DNA Triazole Phosphoramidite (12)

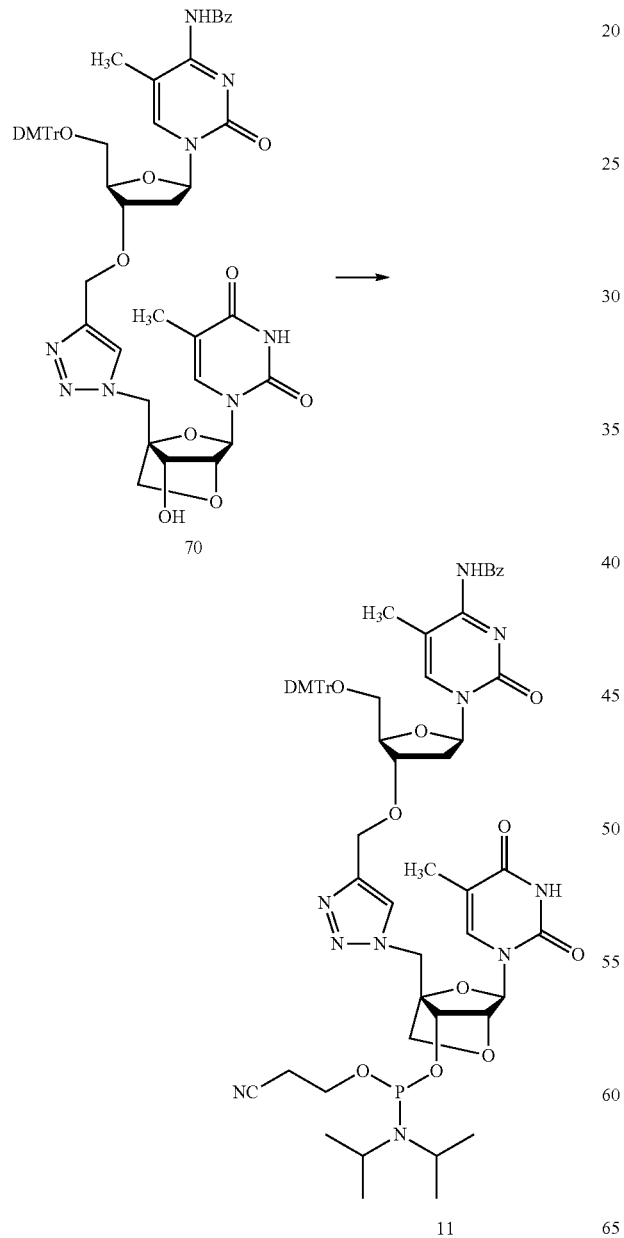

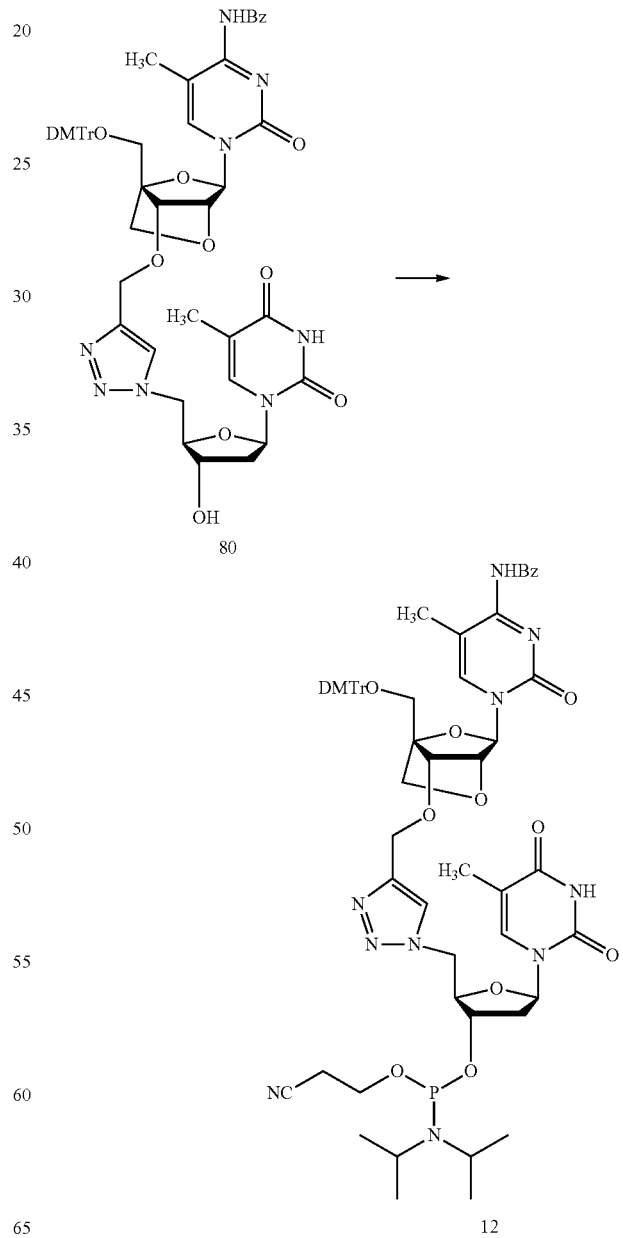

Nucleoside 80 (350 mg, 0.36 mmol) was dissolved in dry $CH_2Cl_2$ (5 mL). DIPEA (250 µL, 1.44 mmol) and 2-cyanoethyl N,N-diisopropylchlorophosphoramidite, (180 µL, 0.72 mmol), were added and reaction mixture was stirred at room temperature for 2 h. Reaction was diluted with $CH_2Cl_2$ (30 mL) and washed with sat. aqueous KCl (30 mL). The organic phase was dried ($Na_2SO_4$) and concentrated under reduced pressure. The residue was purified using column chromatography (0 to 3% MeOH in $CH_2Cl_2$) to obtain 12 (320 mg, 76%) as a white foam. $R_f$ (0.5, 5% MeOH in $CH_2Cl_2$). ESI HRMS m/z 1181.4859 ([M+H]$^+$, $C_{61}H_{70}O_{13}N_{10}P^+$ calc. 1181.4856. $^{31}P$ NMR (126 MHz, $CD_3CN$) δ 148.69, 148.55.

Synthesis of LNA/LNA Triazole Phosphoramidite (13)

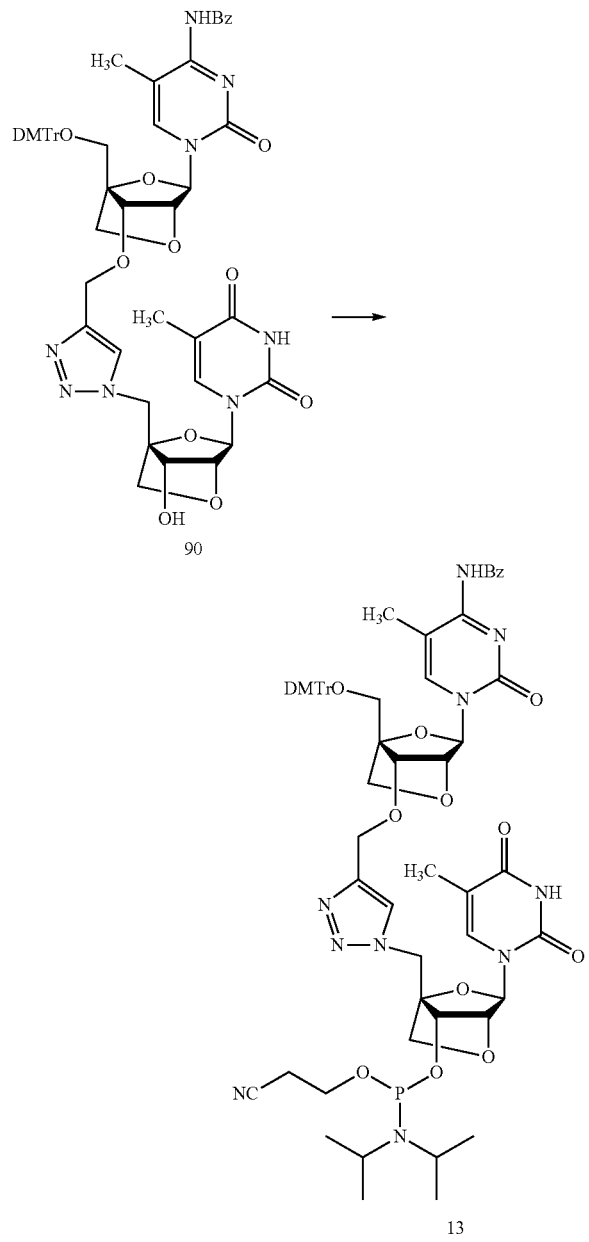

Nucleoside 90 (280 mg, 0.28 mmol) was dissolved in dry $CH_2Cl_2$ (5 mL). DIPEA (0.18 mL, 1.03 mmol) and 2-cyanoethyl N,N-diisopropylchlorophosphoramidite, (136 µL, 0.58 mmol), were added and reaction mixture was stirred at room temperature for 2 h. Reaction was diluted with $CH_2Cl_2$ (30 mL) and washed with sat. aqueous KCl (30 mL). The organic phase was dried ($Na_2SO_4$) and concentrated under reduced pressure. The residue was purified using column chromatography (0 to 3% MeOH in $CH_2Cl_2$) to obtain 13 (245 mg, 73%) as a white foam. $R_f$ (0.5, 4% MeOH in $CH_2Cl_2$). ESI HRMS m/z 1209.4813 ([M+H]$^+$, $C_{62}H_{70}O_{14}N_{10}P^+$ calc. 1209.4805. $^{31}P$ NMR (126 MHz, $CD_3CN$) δ 149.27, 148.87.

Synthesis and Purification of Oligonucleotides

Standard DNA phosphoramidites, solid supports and reagents were purchased from Link Technologies and Applied Biosystems. LNA phosphoramidites were obtained from Exiqon.

Synthesis of Activated Resin

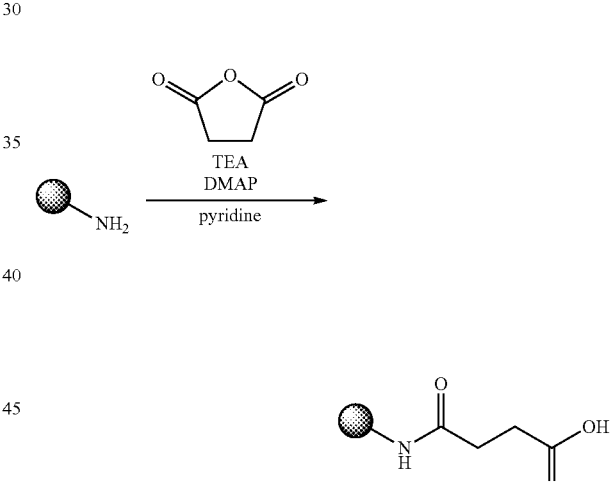

Amino-SynBase resin 500/100 (Link Technologies, Glasgow, UK) (500 Å pore size, loading 69 µmol/g, 4.06 g, 0.28 mmol of amine) was activated using 3% solution of trichloroacetic acid in $CH_2Cl_2$ for 3 h in a stoppered glass vessel fitted with a sinter and tap. The solvents were removed by filtration and the support was washed with triethylamine:diisopropylethylamine (9:1), $CH_2Cl_2$, and diethyl ether. The support was dried under vacuum for 1 h and re-suspended in anhydrous pyridine (10 mL). A solution of succinic anhydride (0.813 g, 8.13 mmol) and DMAP (160 mg, 1.3 mmol) in anhydrous pyridine (5 mL) was added and the vessel was rotated at room temperature for 20 h. The solvents were removed by filtration, and the support was washed with pyridine, $CH_2Cl_2$, and diethyl ether and dried under high vacuum for 1 h.

Synthesis of Resin-Bound Dimers

Dimers were loaded onto an activated resin to allow modification at the 3′-end.

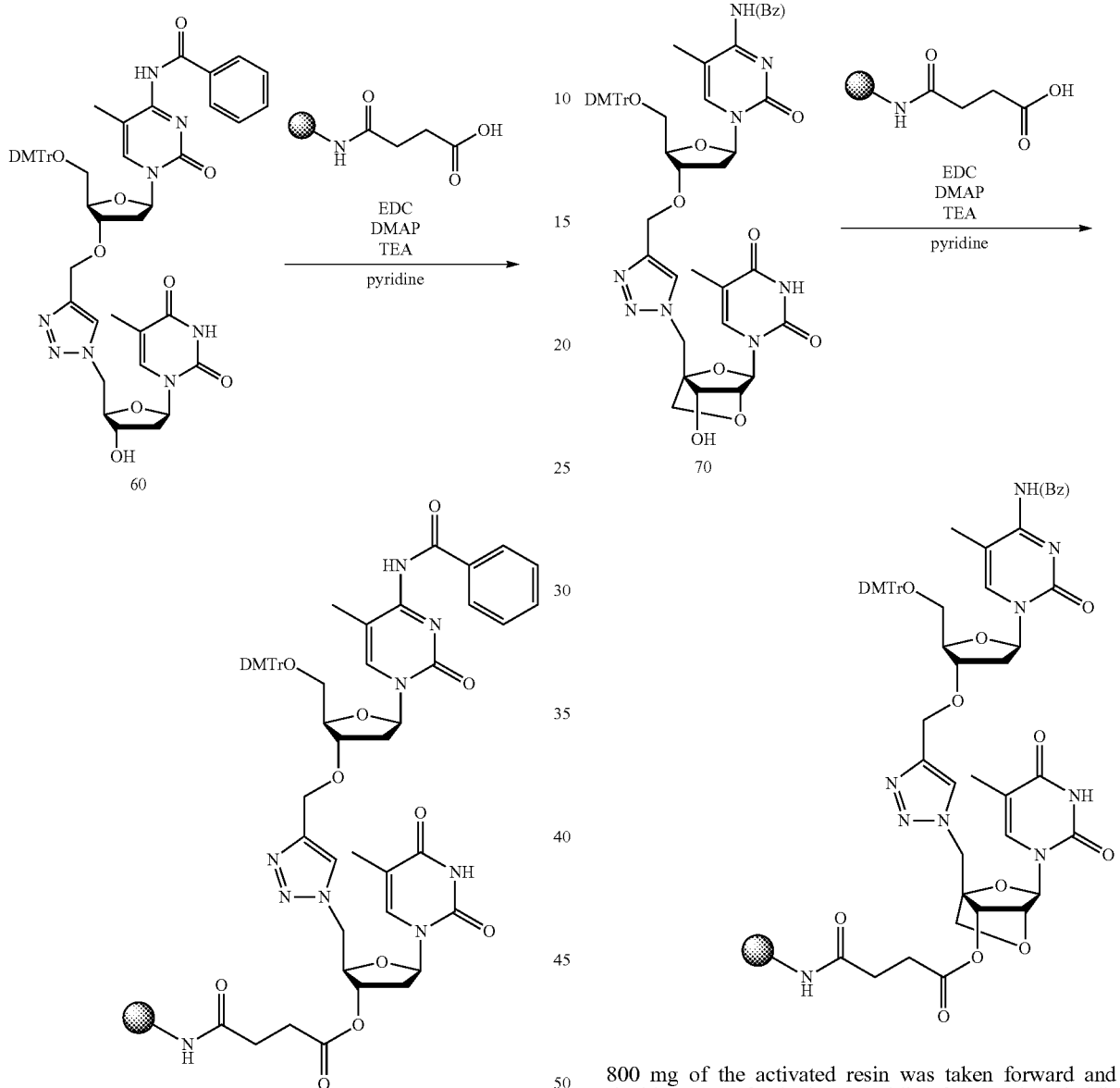

60

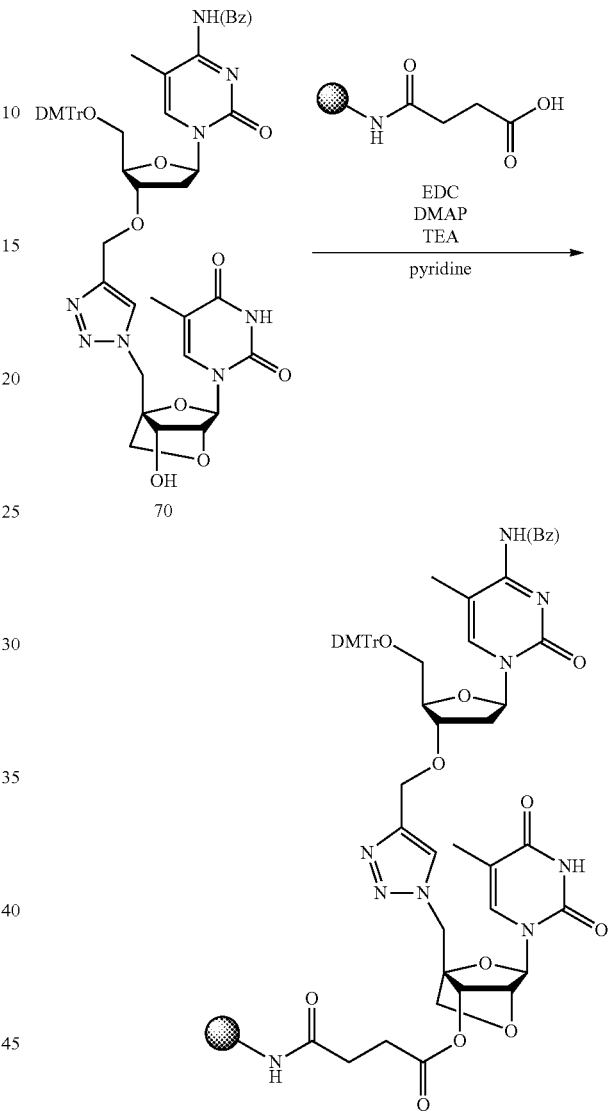

70

500 mg of the activated resin was taken forward and soaked in 1 mL of anhydrous pyridine for 10 min. Ethyldimethylaminopropylcarbodiimide hydrochloride (EDC) (170 mg, 1.09 mmol), DMAP (36 mg, 0.29 mmol), triethylamine (44 µL, 0.32 mmol), and compound 60 (56 mg, 59 µmol) were added to the resin. The reaction vessel was rotated for 20 h at room temperature, after which pentachlorophenol (26 mg, 98 µmol) was added and the vessel was rotated for an additional 3 h. The solvents were removed by filtration, and the support was washed with pyridine, $CH_2Cl_2$, and diethyl ether. Piperidine (10% in DMF, 2 mL) was added and the vessel was rotated for 5 min at room temperature. The solvent was removed by filtration and the support was washed with $CH_2Cl_2$ and diethyl ether. Capping reagent (oligonucleotide synthesis grade, acetic anhydride/pyridine/THF:N-methylimidazole in THF, 1:1, 2 mL) was added and the vessel was rotated at room temperature for 1 h. The solvent was removed by filtration, and the resin was washed with pyridine, $CH_2Cl_2$, and diethyl ether and dried under high vacuum overnight.

800 mg of the activated resin was taken forward and soaked in 1 mL of anhydrous pyridine for 10 min Ethyldimethylaminopropylcarbodiimide hydrochloride (EDC) (0.329 g, 2.12 mmol), DMAP (14 mg, 0.11 mmol), triethylamine (85 µL, 0.61 mmol), and compound 70 (100 mg, 0.102 mmol) were added to the resin. The reaction vessel was rotated for 20 h at room temperature, after which pentachlorophenol (49 mg, 0.18 mmol) was added and the vessel was rotated for an additional 3 h. The solvents were removed by filtration, and the support was washed with pyridine, $CH_2Cl_2$, and diethyl ether. Piperidine (10% in DMF, 2 mL) was added and the vessel was rotated for 5 min at room temperature. The solvent was removed by filtration and the support was washed with $CH_2Cl_2$ and diethyl ether. Capping reagent (oligonucleotide synthesis grade, acetic anhydride/pyridine/THF:N-methylimidazole in THF, 1:1, 2 mL) was added and the vessel was rotated at room temperature for 1 h. The solvent was removed by filtration, and the resin was washed with pyridine, $CH_2Cl_2$, and diethyl ether and dried under high vacuum overnight.

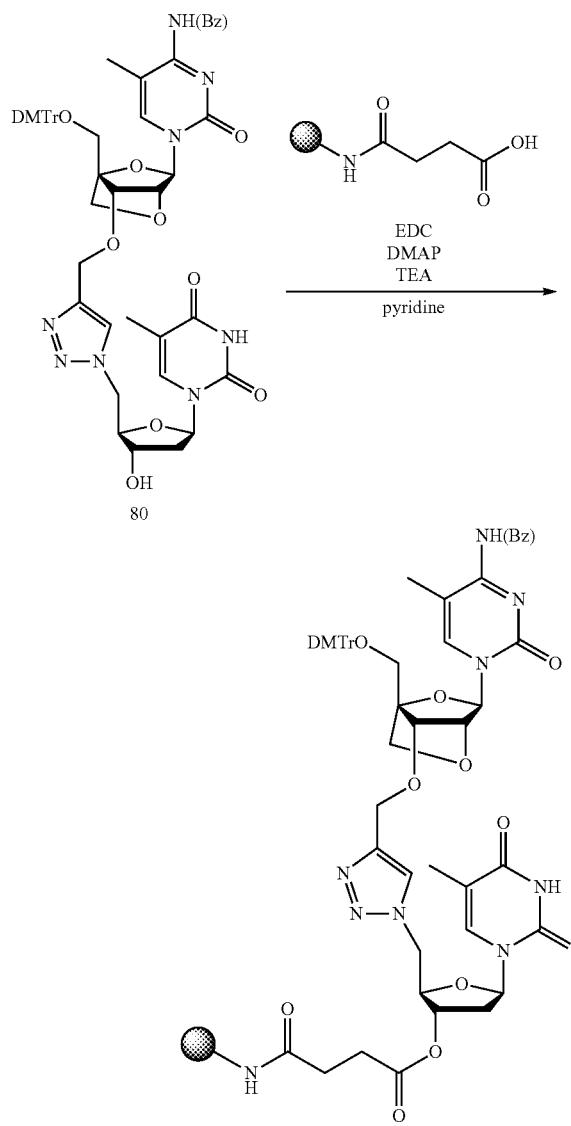

80

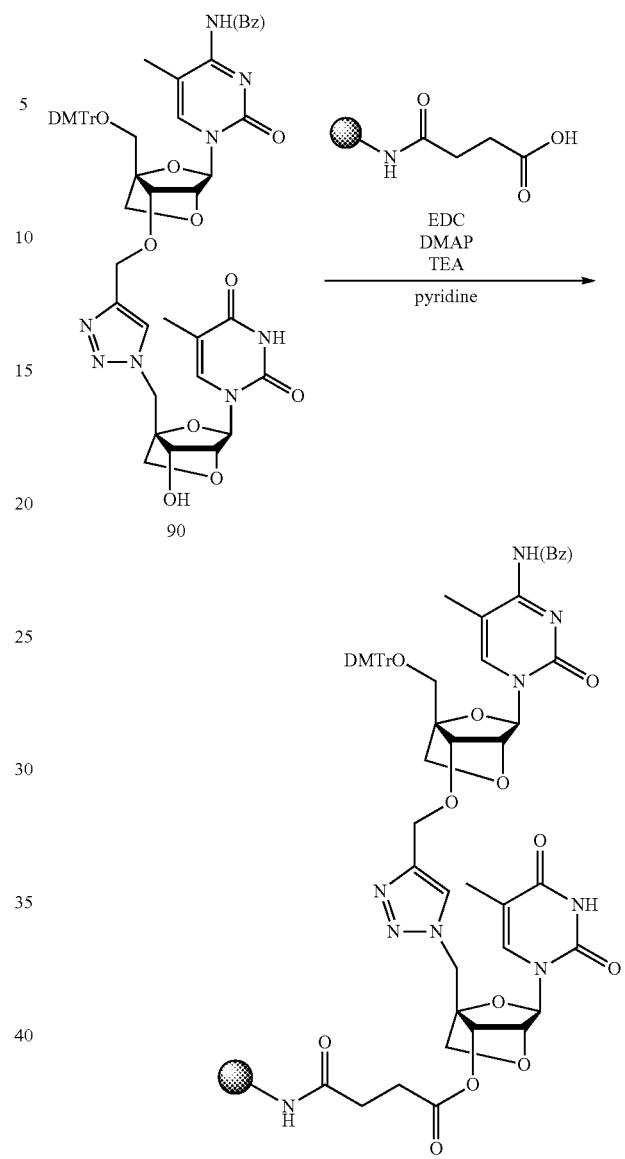

90

300 mg of the activated resin was taken forward and soaked in 1 mL of anhydrous pyridine for 10 min Ethyldimethylaminopropylcarbodiimide hydrochloride (EDC) (0.132 g, 0.850 mmol), DMAP (6 mg, 49 µmol), triethylamine (34 µL, 0.24 mmol), and compound 80 (40 mg, 41 µmol) were added to the resin. The reaction vessel was rotated for 20 h at room temperature, after which pentachlorophenol (20 mg, 75 µmol) was added and the vessel was rotated for an additional 3 h. The solvents were removed by filtration, and the support was washed with pyridine, $CH_2Cl_2$, and diethyl ether. Piperidine (10% in DMF, 2 mL) was added and the vessel was rotated for 5 min at room temperature. The solvent was removed by filtration and the support was washed with $CH_2Cl_2$ and diethyl ether. Capping reagent (oligonucleotide synthesis grade, acetic anhydride/pyridine/THF:N-methylimidazole in THF, 1:1, 2 mL) was added and the vessel was rotated at room temperature for 1 h. The solvent was removed by filtration, and the resin was washed with pyridine, $CH_2Cl_2$, and diethyl ether and dried under high vacuum overnight.

250 mg of the activated resin was taken forward and soaked in 1 mL of anhydrous pyridine for 10 min Ethyldimethylaminopropylcarbodiimide hydrochloride (EDC) (0.106 g, 0.683 mmol), DMAP (5 mg, 41 µmol), triethylamine (28 µL, 0.20 mmol), and compound 90 (33 mg, 33 µmol) were added to the resin. The reaction vessel was rotated for 20 h at room temperature, after which pentachlorophenol (16 mg, 60 µmol) was added and the vessel was rotated for an additional 3 h. The solvents were removed by filtration, and the support was washed with pyridine, $CH_2Cl_2$, and diethyl ether. Piperidine (10% in DMF, 2 mL) was added and the vessel was rotated for 5 min at room temperature. The solvent was removed by filtration and the support was washed with $CH_2Cl_2$ and diethyl ether. Capping reagent (oligonucleotide synthesis grade, acetic anhydride/pyridine/THF:N-methylimidazole in THF, 1:1, 2 mL) was added and the vessel was rotated at room temperature for 1 h. The solvent was removed by filtration, and the resin was washed with pyridine, $CH_2Cl_2$, and diethyl ether and dried under high vacuum overnight.

Synthesis of DNA Oligonucleotides

Automated solid phase synthesis of oligonucleotides (trityl off) was performed on an Applied Biosystems 394 synthesiser. Synthesis was performed on 1.0 µmole scale involving cycles of acid-catalyzed detritylation, coupling, capping, and iodine oxidation according to known synthetic methodology (e.g. Beaucage & Iyer "Advances in the Synthesis of Oligonucleotides by the Phosphoramidite Approach", *Tetrahedron* (1992), 48 (12) 2223-2311). Standard DNA phosphoramidites were coupled for 60 s while extended coupling time of 10 min was used for the modified phosphoramidites. Modified phosphoramidites 10, 11, 12 and 13 were used to obtain modified monomers W, X, Y and Z respectively:

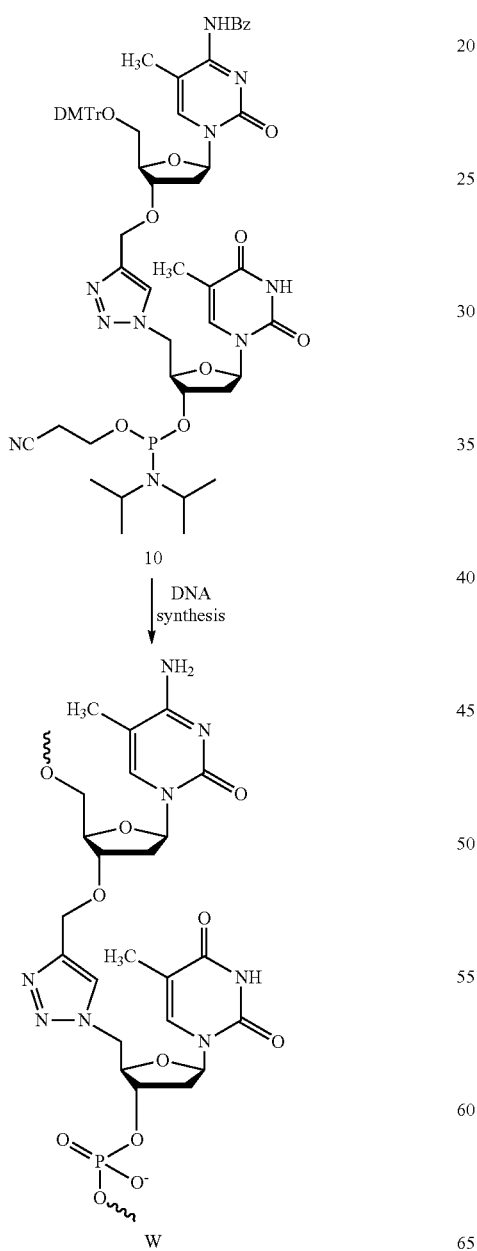

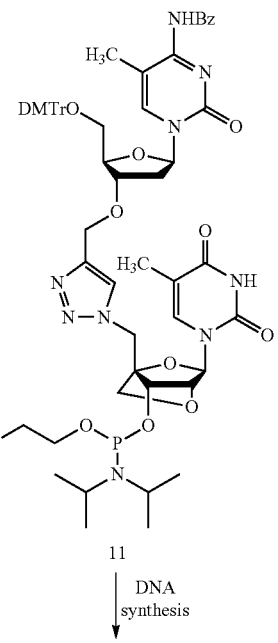

-continued

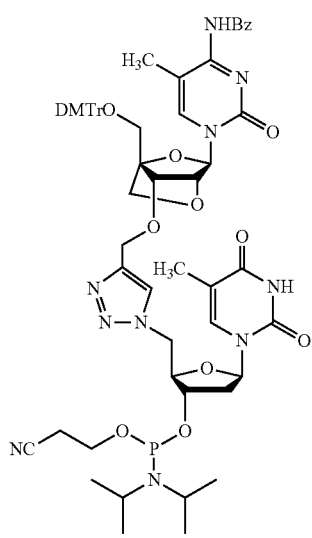

12

| DNA synthesis

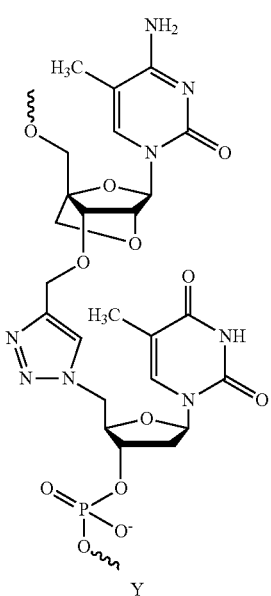

Y

-continued

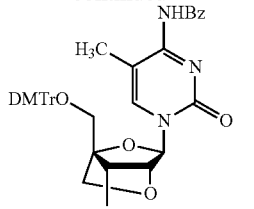

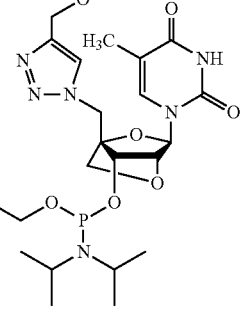

13

| DNA synthesis

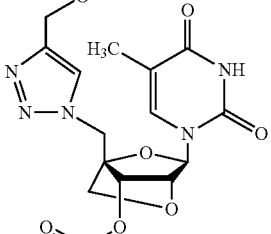

Z

Coupling efficiencies and overall synthesis yields were determined by the inbuilt automated trityl cation conductivity monitoring facility and were >98.0% in all cases. The oligonucleotides were then cleaved from the solid support and protecting groups from the nucleobase and backbone were removed by exposure to concentrated aqueous ammonium hydroxide for 60 min at room temperature followed by heating in a sealed tube for 5 h at 55° C.

Purification of Oligonucleotides

The fully deprotected oligonucleotides were then purified by reverse-phase high performance liquid chromatography (HPLC) on a Gilson system using a Luna 10 μm C8(2) 100 Å pore Phenomenex column (250×10 mm) with a gradient of acetonitrile in triethylammonium bicarbonate (TEAB) over 20 min at a flow rate of 4 mL per minute. Buffer A: 0.1 M TEAB, pH 7.5; buffer B: 0.1 M TEAB, pH 7.5, with 50% acetonitrile were used. Elution was monitored by UV absorption between 260-295 nm.

Ultraviolet Melting Studies

UV DNA melting curves were recorded in a Cary 4000 Scan UV-Visible Spectrophotometer using 3 μM of each oligonucleotide in a 10 mM phosphate buffer containing 200 mM NaCl at pH 7.0. Samples were annealed by heating to 85° C. (10° C./min) and then slowly cooling to 20° C. (1° C./min). As these six successive cycles (heating and cooling) were performed at a gradient of 1° C./min, the change in UV absorbance at 260 nm was recorded. The melting temperature was calculated from the 1$^{st}$ derivative of the melting curve using in built software.

TABLE 1

Thermal melting ($T_m$) data against RNA target

| ON Code | ON Sequence (5'-3') | B = | $T_m^a$ ($\Delta T_m^b$) | | | |
|---|---|---|---|---|---|---|
| | | | W | X | Y | Z |
| 100 | 5'-CTC ACT ATC TGB (SEQ ID NO: 19) | | 53.6 (−1.2) | 54.6 (−0.2) | 54.7 (−0.1) | 55.0 (+0.2) |
| 200 | 5'-BCA CTA TCT GCT (SEQ ID NO: 20) | | 51.3 (−3.5) | 55.7 (+0.9) | 50.6 (−4.2) | 54.8 (0.0) |
| 300 | 5'-CTC ABA TCT GCT (SEQ ID NO: 21) | | — | 57.1 (+2.3) | 49.9 (−4.2) | 58.2 (+3.4) |
| 400 | 5'-CTC ACT ATB GCT (SEQ ID NO: 22) | | 49.1 (−5.7) | 55.0 (+0.2) | 49.2 (−5.6) | 56.9 (+2.1) |
| 500 | 5'-CTC ABA TBG CT (SEQ ID NO: 23) | | — | 57.0 (+2.2) | 44.0 (−10.8) | 58.9 (+4.1) |
| 600 | 5'-BCA BAT BGB (SEQ ID NO: —) | | 38.8 (−16.0) | 57.8 (+3.0) | 38.0 (−16.8) | 62.3 (+7.5) |

$^a$Melting temperatures ($T_m$) were obtained from the maxima of the first derivatives of the melting curves ($A_{260}$ vs. temperature) recorded in a buffer containing 10 mM phosphate and 200 mM NaCl at pH 7.0 using 3.0 μM concentrations of each strand.
$^b\Delta T_m$ = change in $T_m$ for a modified duplex relative to the unmodified duplex 5'-CTC ACT ATC TG$^{Me}$CT (SEQ ID NO: 16) ($T_m$ = 54.8). RNA target: 5'-AGC AGA UAG UGA G (SEQ ID NO: 24).

ON's containing DNA/LNA triazole monomer (monomer X) and LNA/LNA triazole monomer (monomer Z) binds to their RNA target with improved binding affinity compared to unmodified ON's. ON's incorporating multiple additions of LNA/LNA triazole monomer (monomer Z) in particular, binds strongly with RNA target.

TABLE 2

Thermal melting ($T_m$) data against DNA target

| ON Code | ON Sequence (5'-3') | B = | $T_m^a$ ($\Delta T_m^b$) | | | |
|---|---|---|---|---|---|---|
| | | | W | X | Y | Z |
| 100 | 5'-CTC ACT ATC TGB (SEQ ID NO: 19) | | 53.8 (−0.9) | 54.6 (−0.1) | 54.1 (−0.6) | 54.8 (+0.1) |
| 200 | 5'- BCA CTA TCT GCT (SEQ ID NO: 20) | | 50.8 (−3.9) | 50.5 (−4.2) | 49.1 (−5.6) | 49.7 (−5.0) |
| 300 | 5'-CTC ABA TCT GCT (SEQ ID NO: 21) | | — | 53.1 (−1.6) | 44.3 (−10.4) | 55.0 (+0.3) |
| 400 | 5'-CTC ACT ATB GCT (SEQ ID NO: 22) | | 49.6 (−5.1) | 51.0 (−3.7) | 45.1 (−9.6) | 52.1 (−2.6) |

TABLE 2-continued

Thermal melting (T$_m$) data against DNA target

| ON Code | ON Sequence (5'-3') | B = | T$_m$$^a$ (ΔT$_m$$^b$) | | | |
|---|---|---|---|---|---|---|
| | | | W | X | Y | Z |
| 500 | 5'-CTC ABA TBG CT (SEQ ID NO: 23) | | — | 48.7 (-6.0) | 35.0 (-19.7) | 51.5 (-3.2) |
| 600 | 5'-BCA BAT BGB | | 37.5 (-17.2) | 45.9 (-8.8) | — | 48.2 (-6.5) |

$^a$Melting temperatures (T$_m$) were obtained from the maxima of the first derivatives of the melting curves (A$_{260}$ vs. temperature) recorded in a buffer containing 10 mM phosphate and 200 mM NaCl at pH 7.0 using 3.0 μM concentrations of each strand.
$^b$ΔT$_m$ = change in T$_m$ for a modified duplex relative to the unmodified duplex 5'-CTC ACT ATC TG$^{Me}$CT (SEQ ID NO: 16) (T$_m$ = 54.7). DNA target: 5'-AGC AGA TAG TGA G (SEQ ID NO: 25).

TABLE 3

Mismatch discrimination

| | RNA Target 3'-rGAG UGM UAG ACG A | |
|---|---|---|
| ON Code | ON SEQUENCE | T$_M$$^a$ M = A | ΔT$_M$ U |
| ON100 | 5'-CTC ACT ATC TG$^{Me}$CT (SEQ ID NO: 16) | 54.8 | -11.3 |
| ON200 | 5'-XCA XAT XGX | 57.8 | -12.5 |
| ON300 | 5'-ZCA ZAT ZGZ | 62.3 | -8.9 |

$^a$See table 1.
ΔT$_m$ = change in T$_m$ relative to the fully matched duplex (M = A).
$^{Me}$C is 5-methylcytosine. Mismatch discrimination is maintained even by highly modified ON's It will be evident from the results above that ON's incorporating multiple additions of monomer X and monomer Z efficiently discriminate between match and mismatch targets.

Snake Venom Phosphodiesterase Stability 5 nm of oligonucleotide was dissolved in 50 μL buffer (100 mM Tris-HCl, 20 mM MgCl$_2$, pH=9.0). 10 μL of this solution was removed as a control (zero min) and was diluted with H$_2$O (10 μL). To the remaining solution was added 30 μL H$_2$O followed by 10 μL aqueous solution of Phosphodiesterase 1 from *Crotalus adamanteus* venom (from Sigma Aldrich, catalogue number P3243, 0.45 units, dissolved in 700 μL H$_2$O). The reaction was incubated at 37° C. and aliquots (20 μL) were taken at different time intervals, mixed with formamide (20 μL) and stored at −20° C. The samples were then analysed by denaturing 20% polyacrylamide gel electrophoresis.

Figure 27:
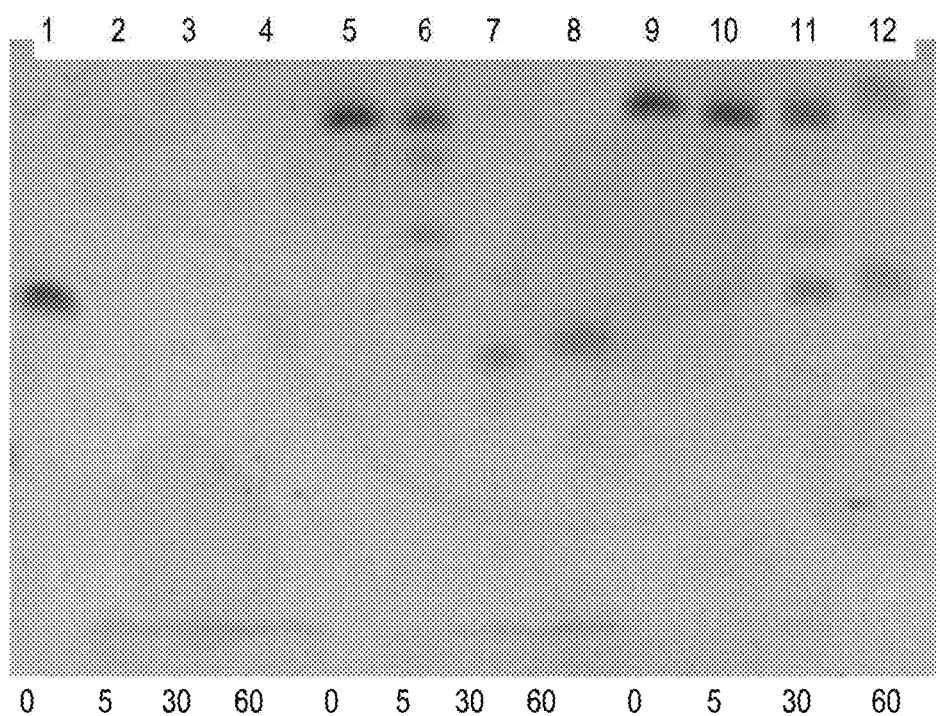
FIG. 27 shows that LNA triazole stabilises ON's to 3'-exonuclease digestion. The unmodified ON: 5'-CTC ACT ATC TG$^{Me}$CT (SEQ ID NO: 16) (lanes 1-4), modified ON: 5'-XCA XAT XGX (lanes 5-8), X=DNA/LNA triazole monomer; ON: 5'-ZCA ZAT ZGZ (lane 9-12) Z=LNA/LNA triazole monomer.
Figure 28:
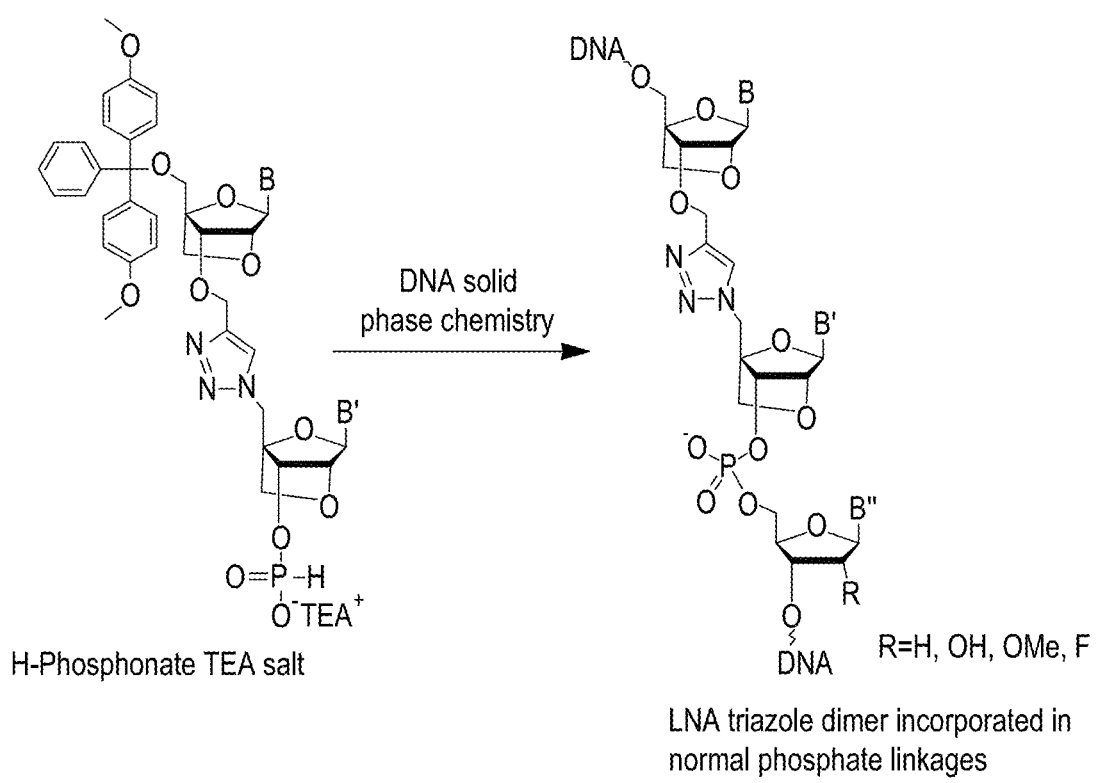
FIG. 28 shows an illustrative non-limiting example of the incorporation of a dinucleotide of formula (I), having a H-phosphonate TAE salt group at the 3' end, into a DNA strand using standard DNA solid phase chemistry techniques. The 3' end of the di-nucleotide is linked to the DNA strand by a normal phosphate inter-nucleoside linkage.
Figure 29:
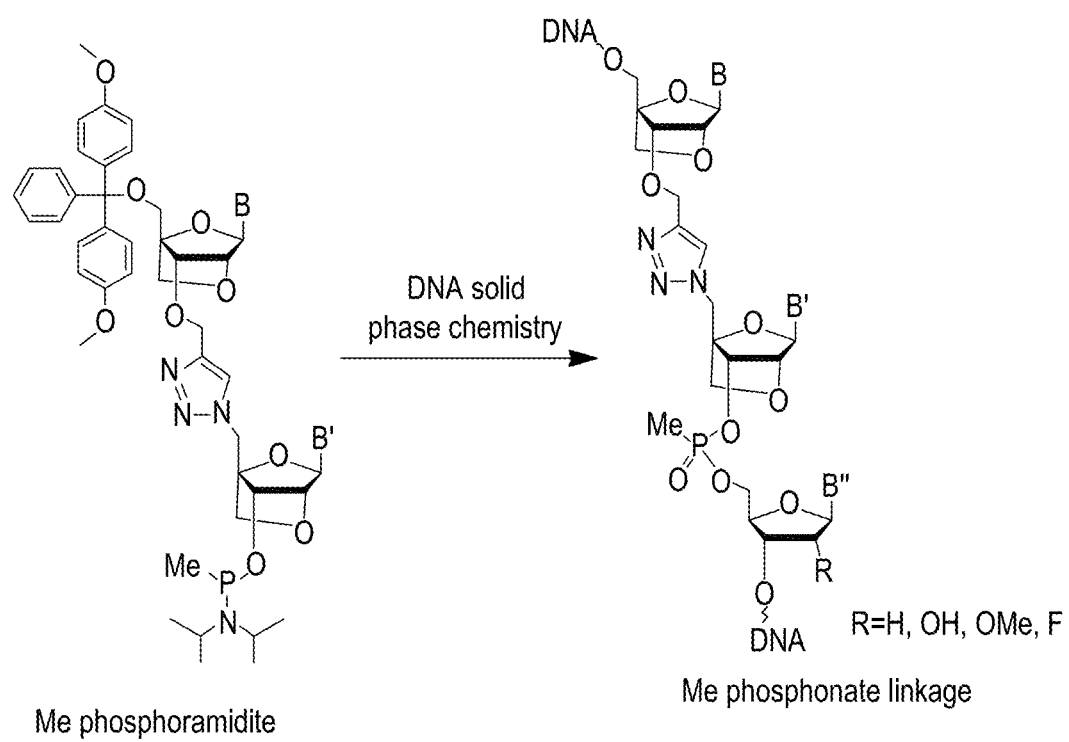
FIG. 29 shows an illustrative non-limiting example of the incorporation of a dinucleotide of formula (I), having a methyl phosphonamidite group at the 3'end, into a DNA strand using standard DNA solid phase chemistry techniques. The 3' end of the di-nucleotide is linked to the DNA strand by a methyl phosphonate inter-nucleoside linkage.
Figure 30:
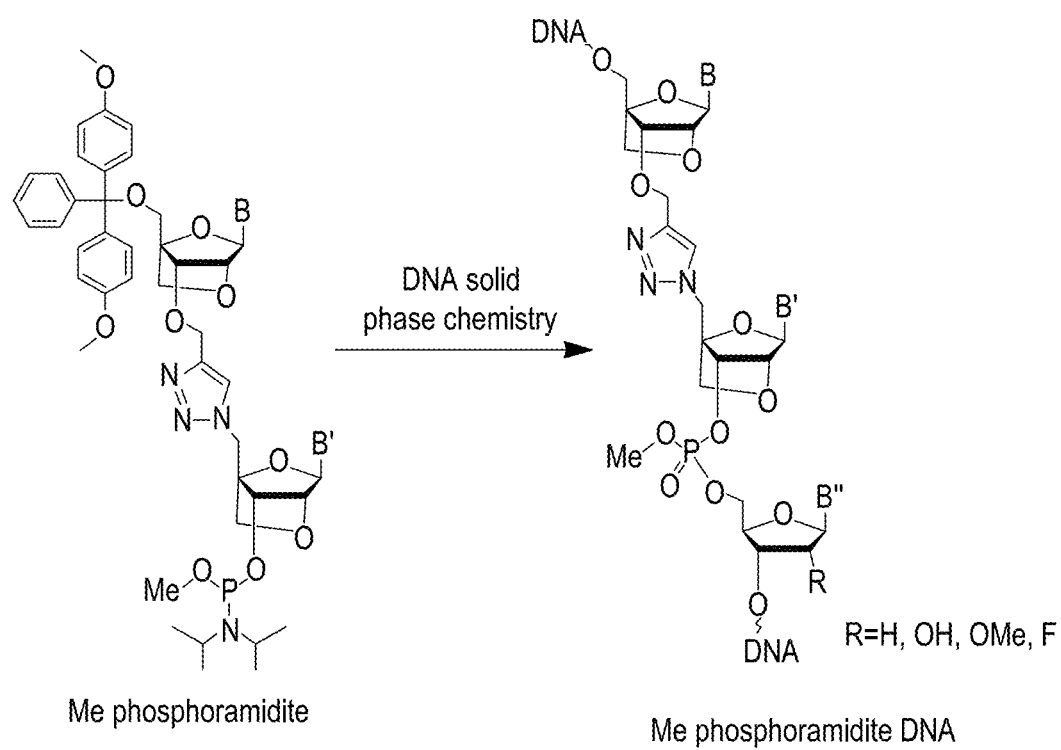
FIG. 30 shows an illustrative non-limiting example of the incorporation of a dinucleotide of formula (I), having a methyl phosphoramidite group at the 3' end, into a DNA strand using standard DNA solid phase chemistry techniques. The 3' end of the di-nucleotide is linked to the DNA strand by a methyl phosphorate inter-nucleoside linkage (also referred to as methyl phsphoramidate DNA).
Figure 31:
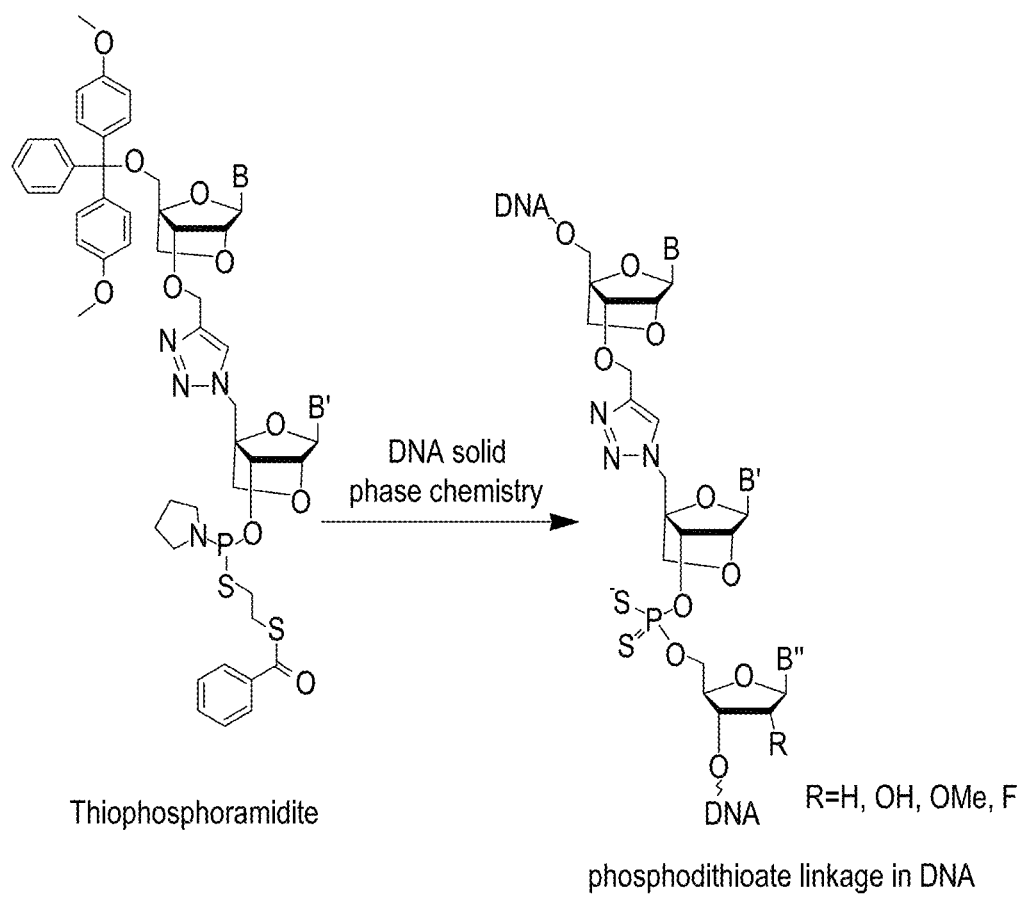
FIG. 31 shows an illustrative non-limiting example of the incorporation of a dinucleotide of formula (I), having a thiophosphoramidate group at the 3' end, into a DNA strand using standard DNA solid phase chemistry techniques. The 3' end of the di-nucleotide is linked to the DNA strand by a phosphodithioate inter-nucleoside linkage.
Figure 32:
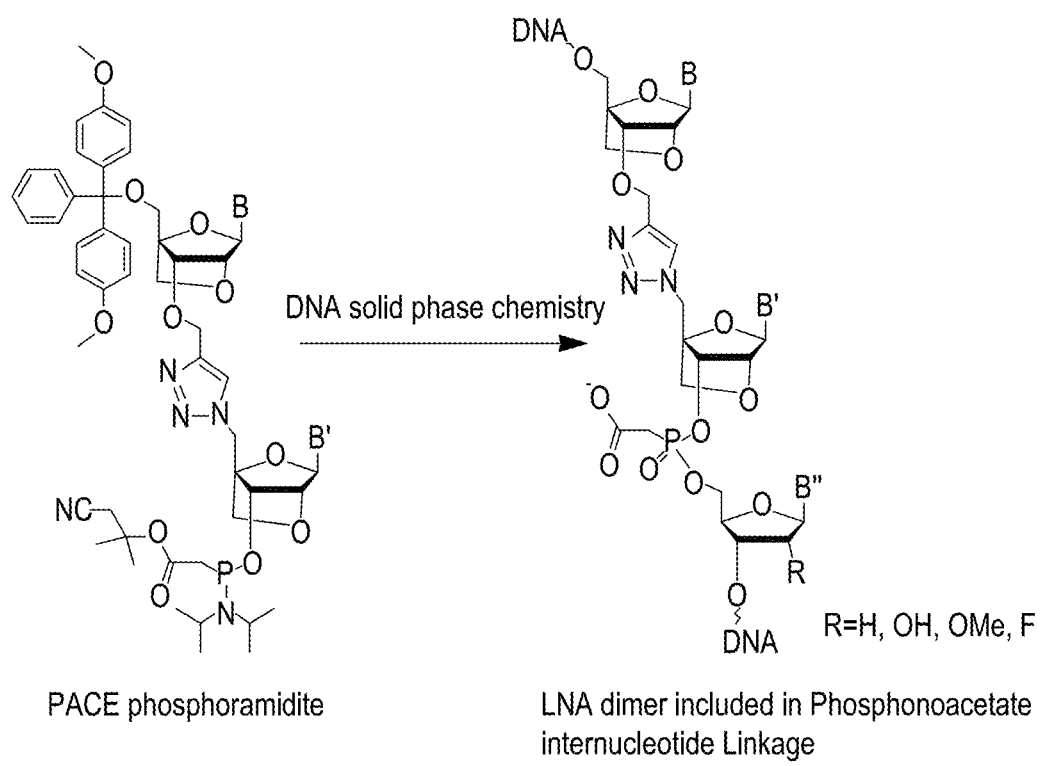
FIG. 32 shows an illustrative non-limiting example of the incorporation of a dinucleotide of formula (I), having a PACE phosphoramidate group at the 3'end, into a DNA strand using standard DNA solid phase chemistry techniques. The 3' end of the di-nucleotide is linked to the DNA strand by a phosphonoacetate inter-nucleoside linkage.

Results from the application of the above described method are depicted in FIG. 27 [FIG. 27 shows that LNA triazole stabilises ON's to 3'-exonuclease digestion. The unmodified ON: 5'-CTC ACT ATC TG$^{Me}$CT (SEQ ID NO: 16) (lanes 1-4), modified ON: 5'-XCA XAT XGX (lanes 5-8), X=DNA/LNA triazole monomer; ON: 5'-ZCA ZAT ZGZ (lanes 9-12) Z=LNA/LNA triazole monomer.]

ON's containing LNA/LNA triazole monomer (monomer Z) binds to their RNA target with improved binding affinity. ON: 5'-ZCA ZAT ZGZ visible even after 60 min Further Validation of the Target Oligonucleotide This section provides some further validation of the target oligonucleotides.

Reference is made to the accompanying drawings, in which:

FIG. 1 shows representative melting curves for duplexes containing a single triazole linkage (MeC-T step, left against DNA target and right against RNA target). For sequences see Table 8.

Figure 2:
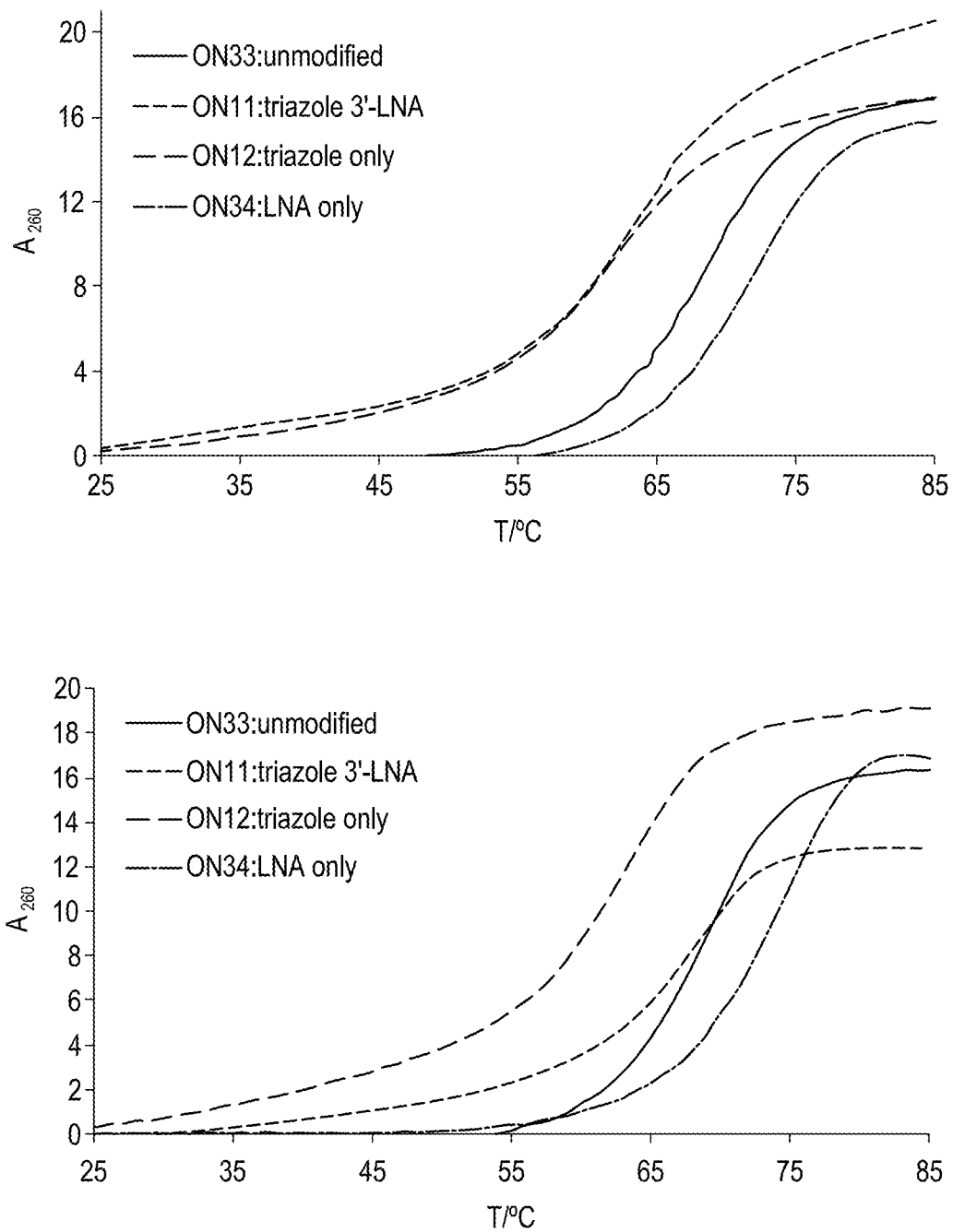
FIG. 2 shows representative melting curves for duplexes containing a single triazole linkage (MeC-MeC step, left against DNA target and right against RNA target). For sequences see Table 4.

FIG. 2 shows representative melting curves for duplexes containing a single triazole linkage (MeC-MeC step, left against DNA target and right against RNA target). For sequences see Table 4.

Figure 3:
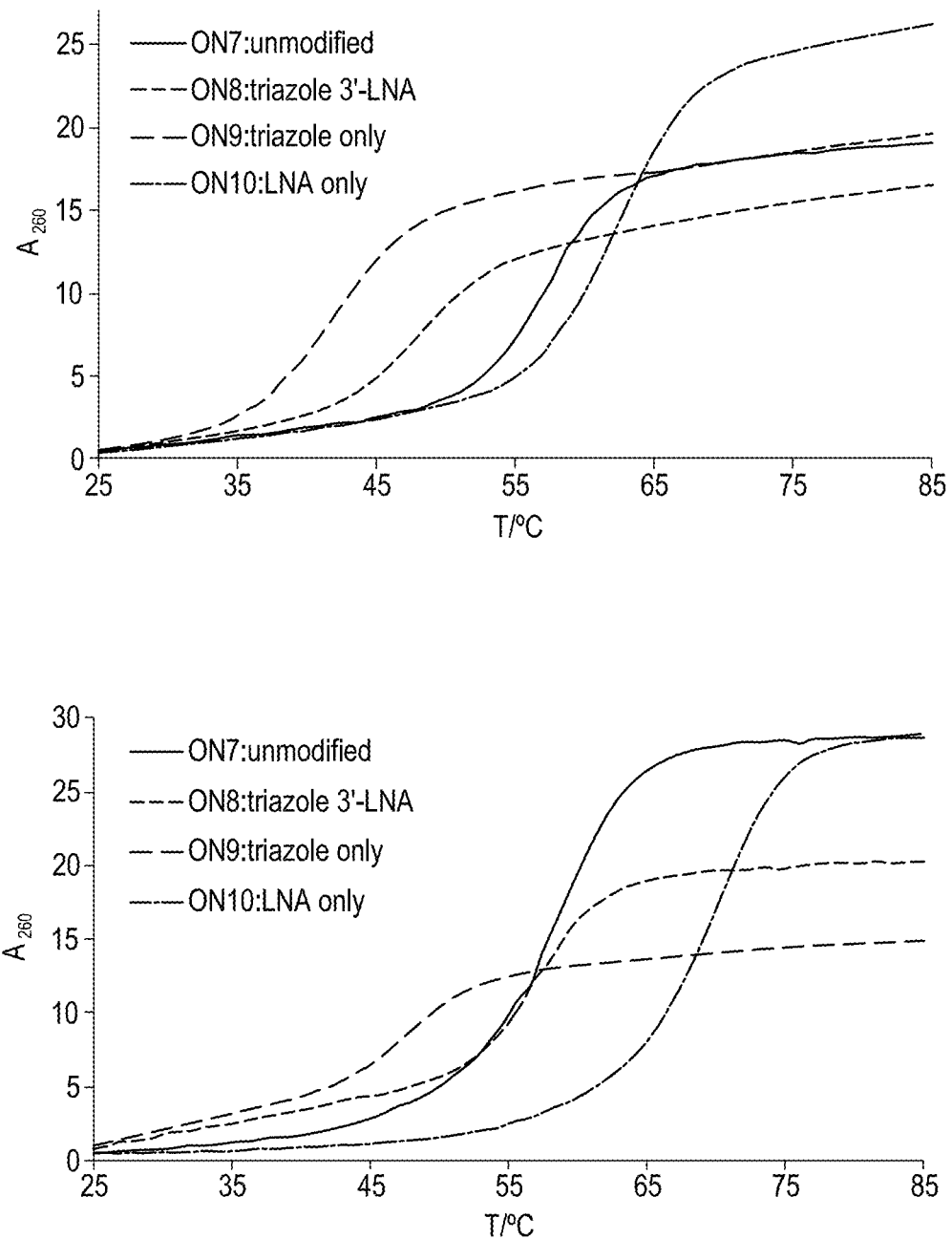
FIG. 3 shows representative melting curves for duplexes incorporating two triazole linkages (MeC-T steps, left against DNA target and right against RNA target). For sequences see Table 9.

FIG. 3 shows representative melting curves for duplexes incorporating two triazole linkages (MeC-T steps, left against DNA target and right against RNA target). For sequences see Table 9.

Figure 4:
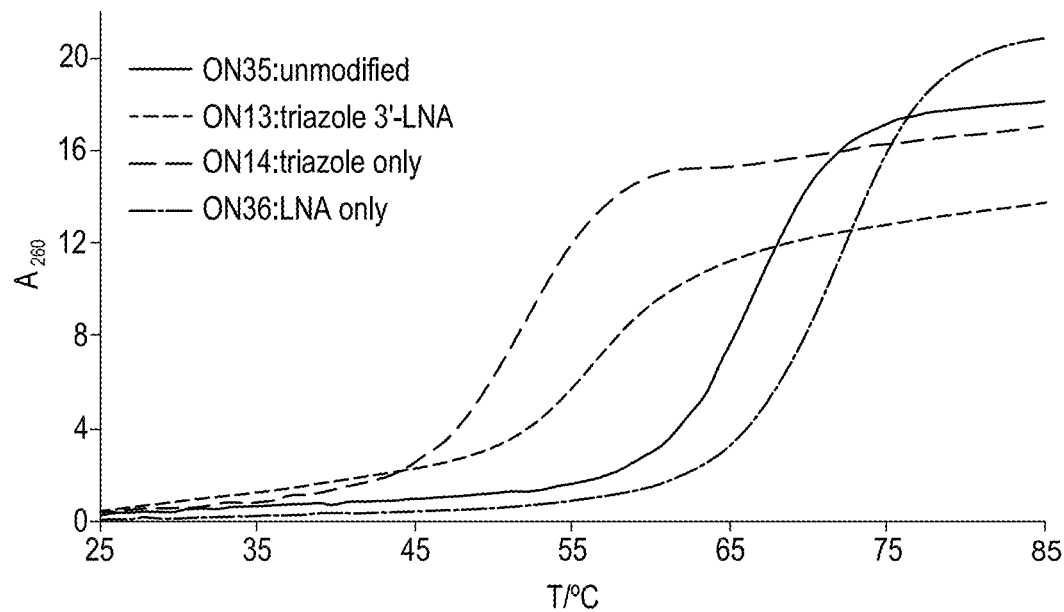
FIG. 4 shows representative melting curves for duplexes incorporating two triazole linkages (MeC-MeC steps, left against DNA target and right against RNA target). For sequences see Table 7.
Figure 4:
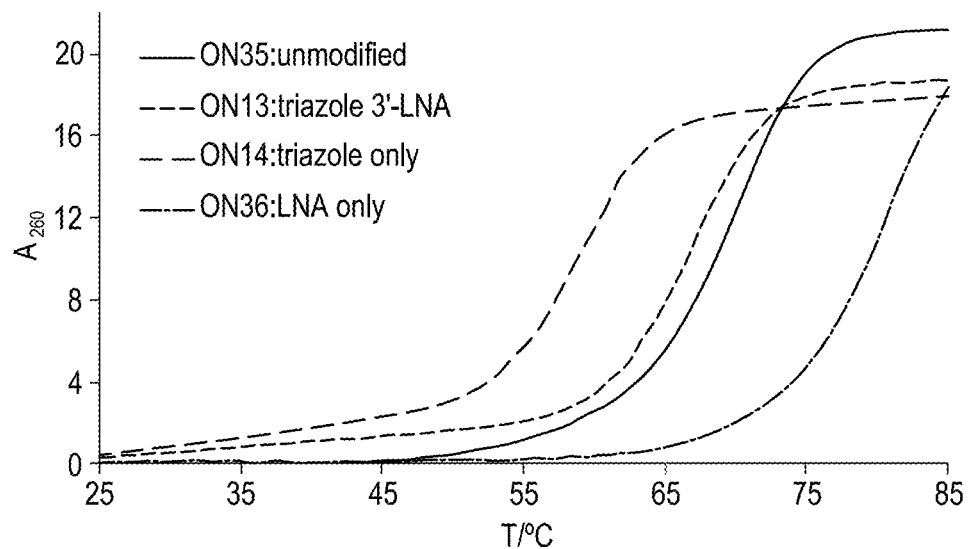

FIG. 4 shows representative melting curves for duplexes incorporating two triazole linkages (MeC-MeC steps, left against DNA target and right against RNA target). For sequences see Table 7.

Figure 5:
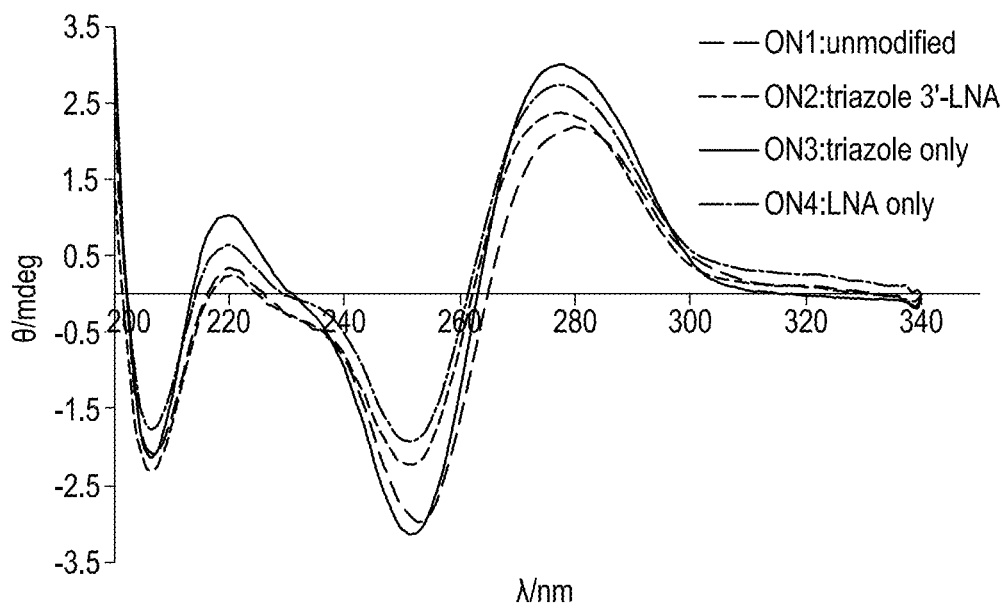
FIG. 5 shows representative CD curves for duplexes containing a single triazole linkage (MeC-T step, left against DNA target; right against RNA target). For sequences see Table 8.
Figure 5:
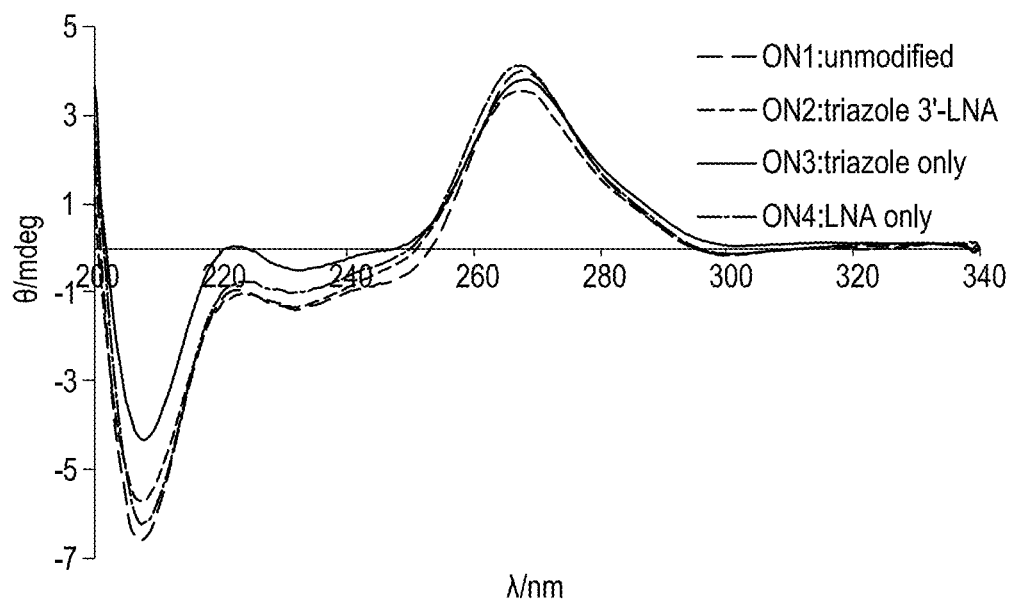

FIG. 5 shows representative CD curves for duplexes containing a single triazole linkage (MeC-T step, left against DNA target; right against RNA target). For sequences see Table 8.

Figure 6:
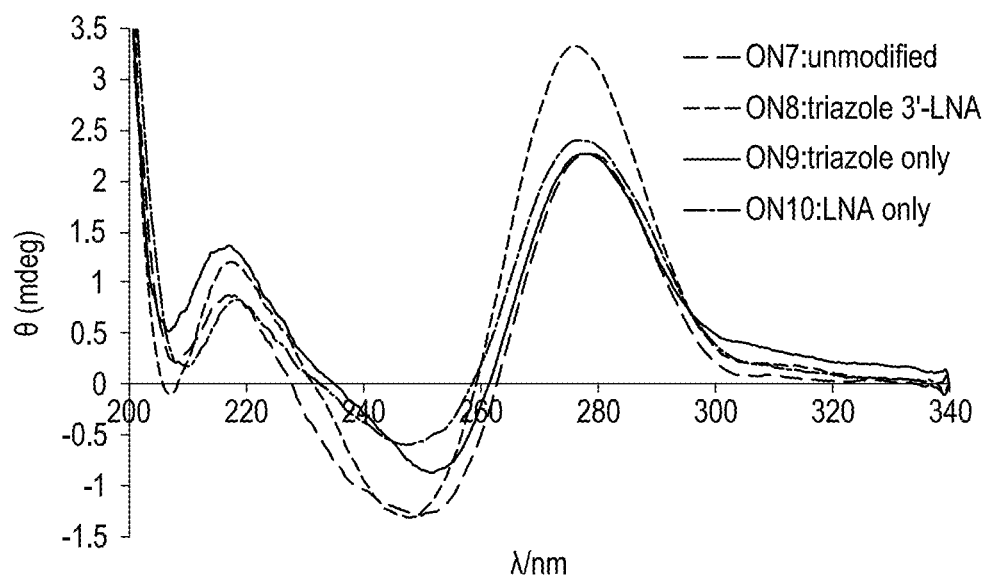
FIG. 6 shows representative CD curves for duplexes incorporating two triazole linkages (MeC-T step, left against DNA target; right against RNA target). For sequences see Table 9.
Figure 6:
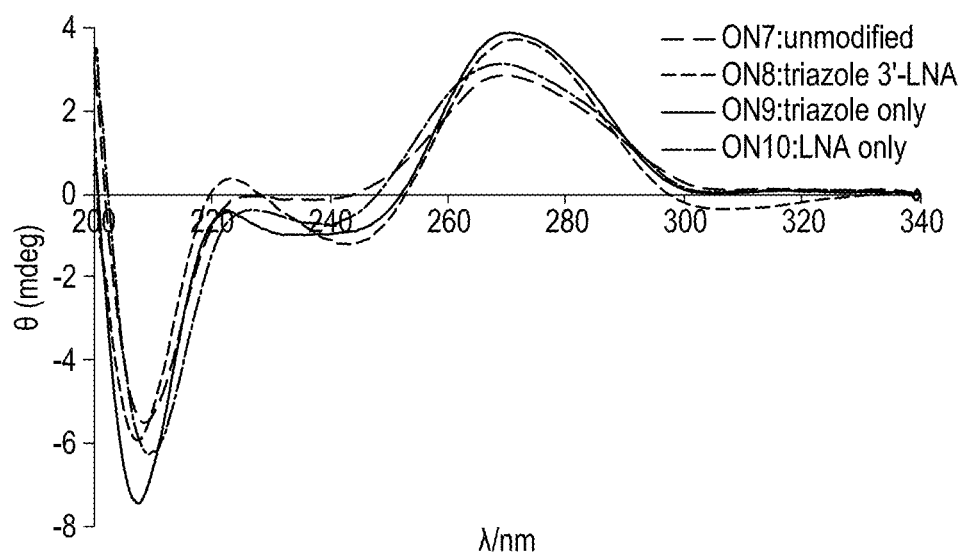

FIG. 6 shows representative CD curves for duplexes incorporating two triazole linkages (MeC-T step, left against DNA target; right against RNA target). For sequences see Table 9.

Figure 7:
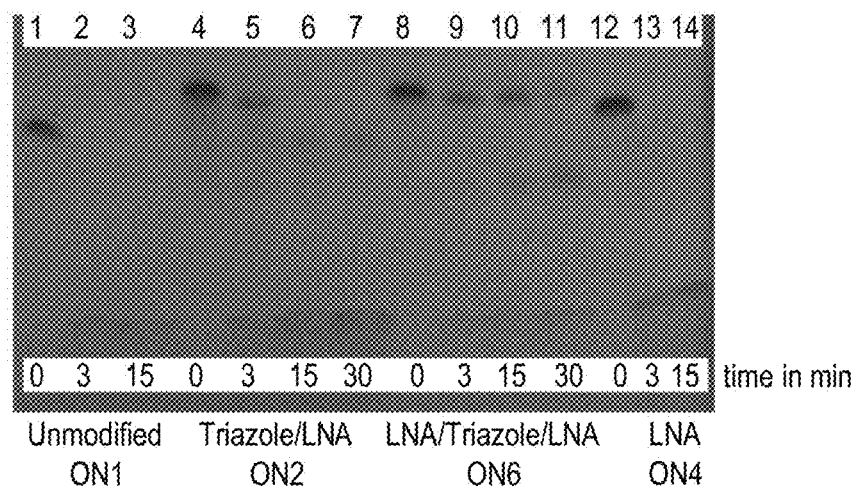
FIG. 7 shows LNA triazole stabilises oligonucleotides to 3'-exonuclease digestion. The ON1:unmodified (lanes 1-3) and ON2:triazole 3'-LNA (lanes 4-7), ON6:triazole 3',5'-LNA (lanes 8-11), ON4:LNA only (lane 12-14).

FIG. 7 shows LNA triazole stabilises oligonucleotides to 3'-exonuclease digestion. The ON1:unmodified (lanes 1-3) and ON2:triazole 3'-LNA (lanes 4-7), ON6:triazole (lanes 8-11), ON4:LNA only (lane 12-14).

Figure 8:
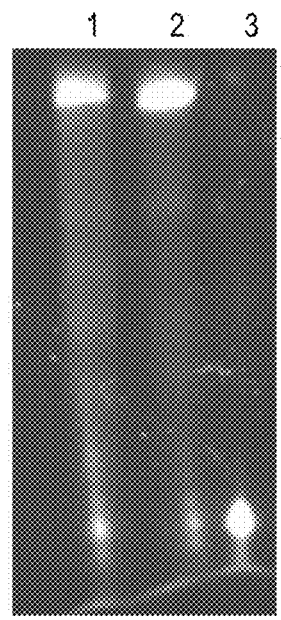
FIG. 8 shows the 10% denaturing polyacrylamide gel from linear copying reaction. Lane 1; Linear copying reaction using modified template (ON15) 5'-dGCA TTC GAG CAA CGT AAG ATC G$^{Me}$CtT$^L$ AGC ACA CAA TCT CAC ACT CTG GAA TTC ACA CTG ACA ATA CTG CCG ACA CAC ATA ACC (SEQ ID NO: 1) where t represent triazole linkage and T$^L$ is LNA thymidine. Lane 2; Linear copying reaction using unmodified template 5'-dACGT-TAGCACGAAGAGGCATCTTAGCACACAATCT-CACACTCTGGAATT-CACACTGACAATACTCGCGAACACACCCAAT (SEQ ID NO: 2). Lane 3; negative control: linear copying reaction using modified template without enzyme. For modified template: Full length product mass; found 26025, calc. 26025. A relatively small peak at 26337 (full length+A) was also observed. For unmodified template: Full length product mass; found 25695, calc. 25695. No M+A product was observed for control. Primer used: 5'-dFTGGT-TATGTGTGTCGGCAG (SEQ ID NO: 3) (for modified template), 5'-dFTATTGGGTGTGTTCGCGAG (SEQ ID NO: 4) (for unmodified template), F is amidohexylfuorescein.

FIG. 8 shows the 10% denaturing polyacrylamide gel from linear copying reaction. Lane 1; Linear copying reaction using modified template (ON15) 5'-dGCA TTC GAG CAA CGT AAG ATC G$^{Me}$CtT$^L$ AGC ACA CAA TCT CAC ACT CTG GAA TTC ACA CTG ACA ATA CTG CCG ACA CAC ATA ACC (SEQ ID NO: 1) where t represent triazole linkage and T$^L$ is LNA thymidine. Lane 2; Linear copying reaction using unmodified template 5'-dACGT-TAGCACGAAGAGGCATCTTAGCACACAATCT-CACACTCTGGAATT-CACACTGACAATACTCGCGAACACACCCAAT (SEQ ID NO: 2). Lane 3; negative control: linear copying reaction using modified template without enzyme. For modified template: Full length product mass; found 26025, calc. 26025. A relatively small peak at 26337 (full length+A) was also observed. For unmodified template: Full length product mass; found 25695, calc. 25695. No M+A product was observed for control. Primer used: 5'-dFTGGT-TATGTGTGTCGGCAG (SEQ ID NO: 3) (for modified template), 5'-dFTATTGGGTGTGTTCGCGAG (SEQ ID NO: 4) (for unmodified template), F is amidohexyfuorescein.

Figure 9:
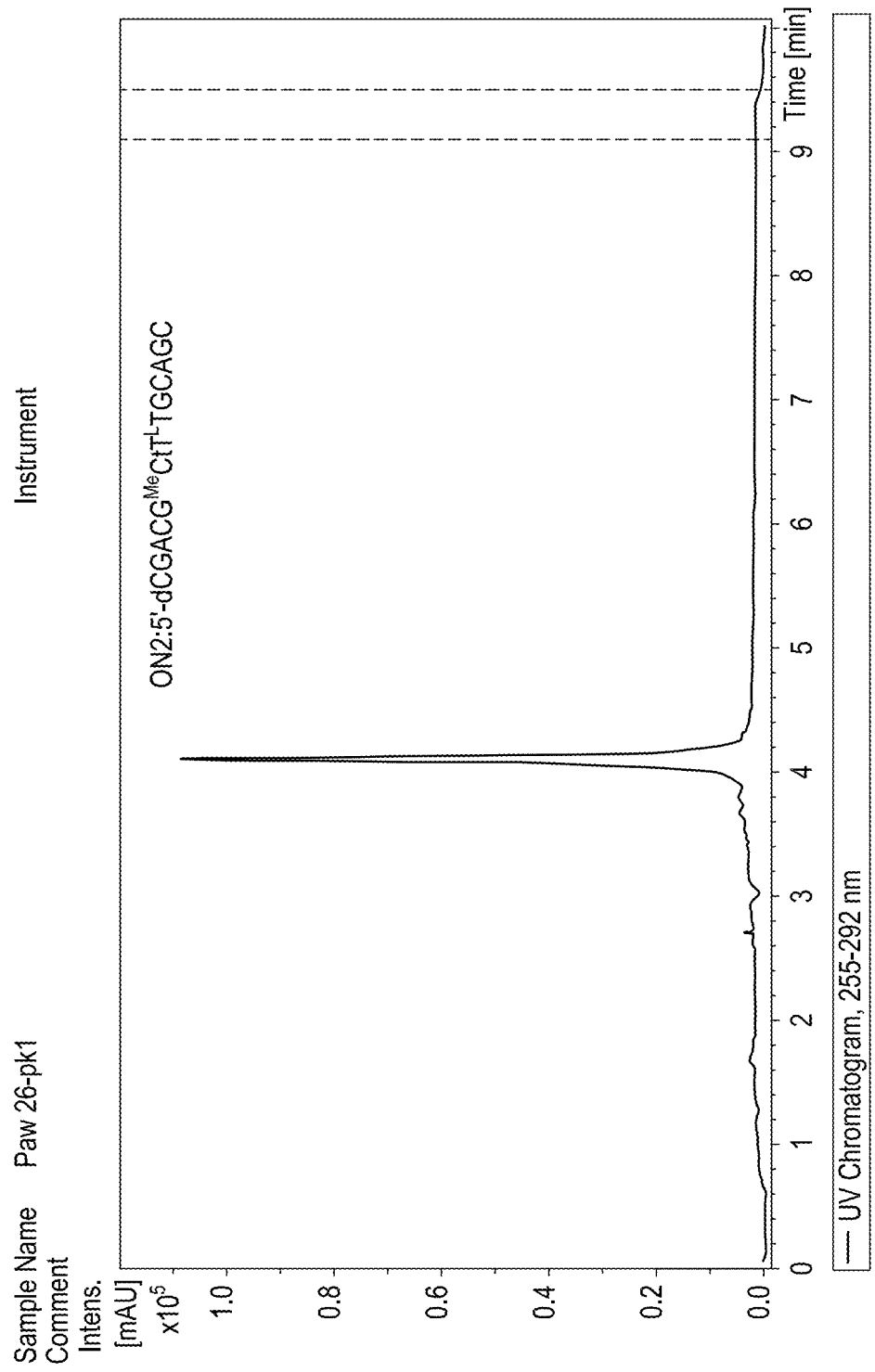
FIG. 9 shows the UV trace from HPLC of HPLC/mass spec for modified oligonucleotide ON2 (SEQ ID NO: 5): 5'-dCGACG $^{Me}$CtT$^L$TGCAGC.

FIG. 9 shows the UV trace from HPLC of HPLC/mass spec for modified oligonucleotide ON2 (SEQ ID NO: 5): 5'-dCGACG MeCtTLTGCAGC.

Figure 10:
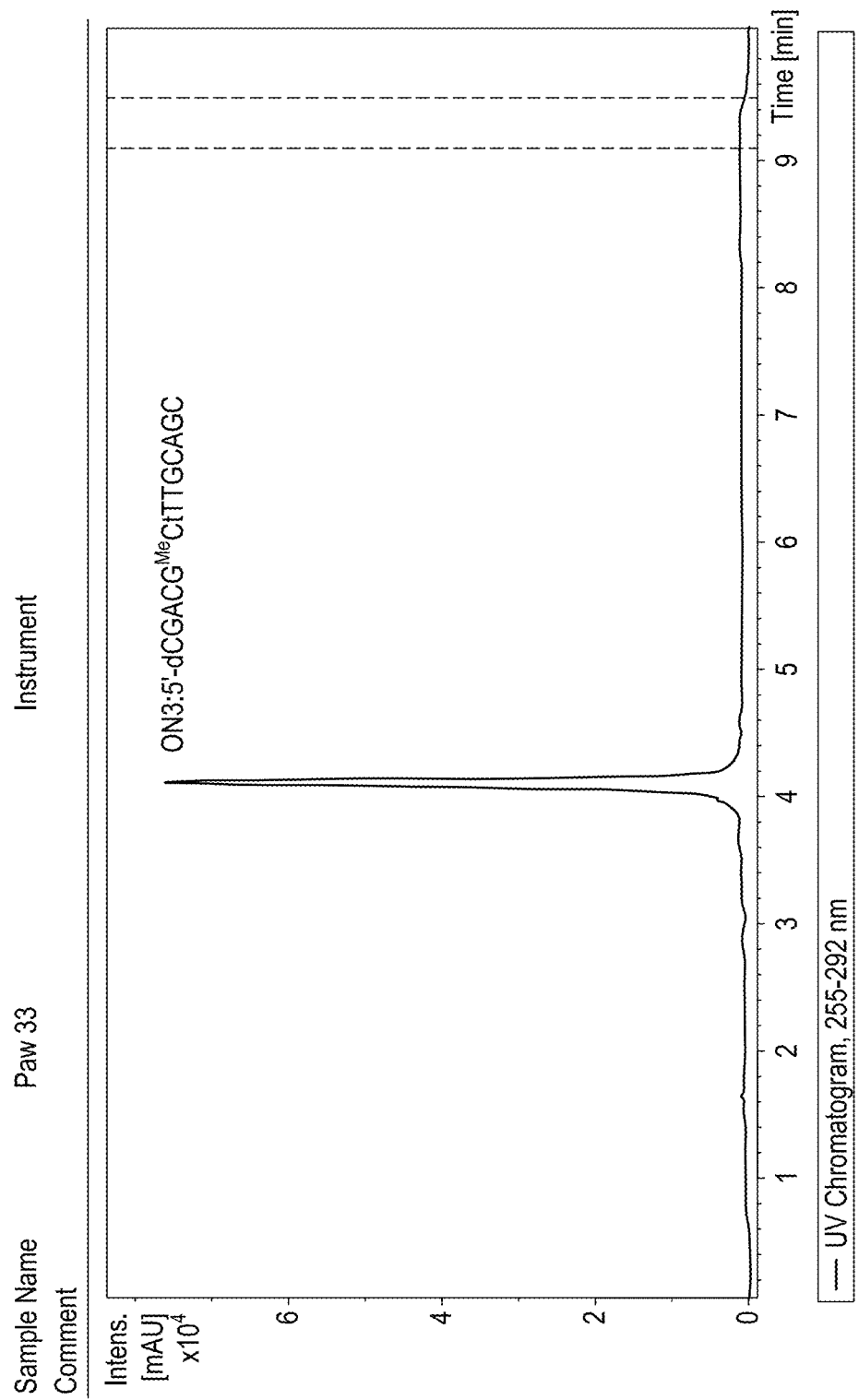
FIG. 10 shows the UV trace from HPLC of HPLC/mass spec for modified oligonucleotide ON3 (SEQ ID NO: 6): 5'-dCGACG $^{Me}$CtTTGCAGC.

FIG. 10 shows the UV trace from HPLC of HPLC/mass spec for modified oligonucleotide ON3 (SEQ ID NO: 6): 5'-dCGACG MeCtTTGCAGC.

Figure 11:
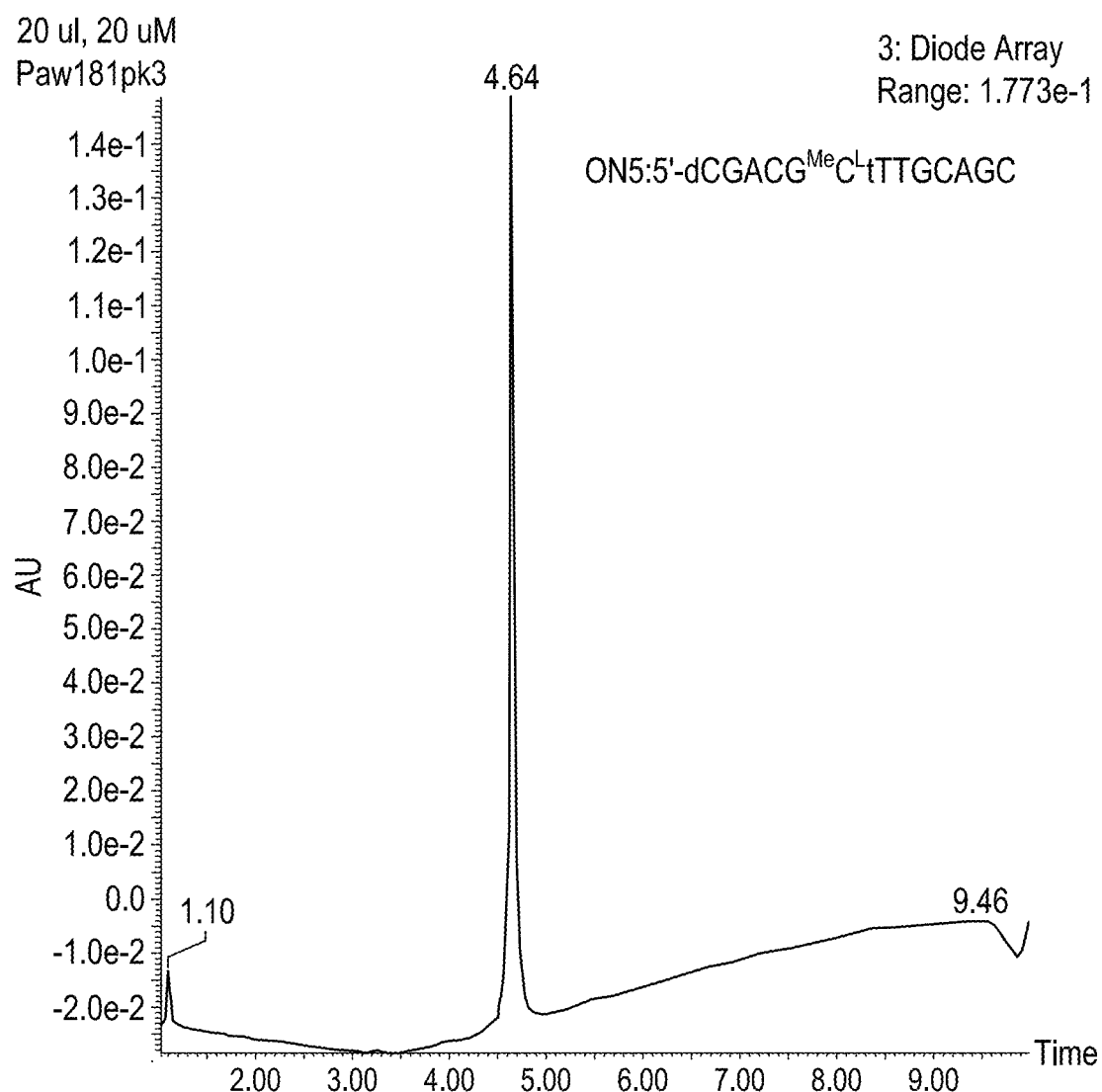
FIG. 11 shows the UV trace from HPLC of HPLC/mass spec for modified oligonucleotide ON5 (SEQ ID NO: 7): 5'-dCGACG $^{Me}$C$^L$tTTGCAGC.

FIG. 11 shows the UV trace from HPLC of HPLC/mass spec for modified oligonucleotide ON5 (SEQ ID NO: 7): 5'-dCGACG MeCLtTTGCAGC.

Figure 12:
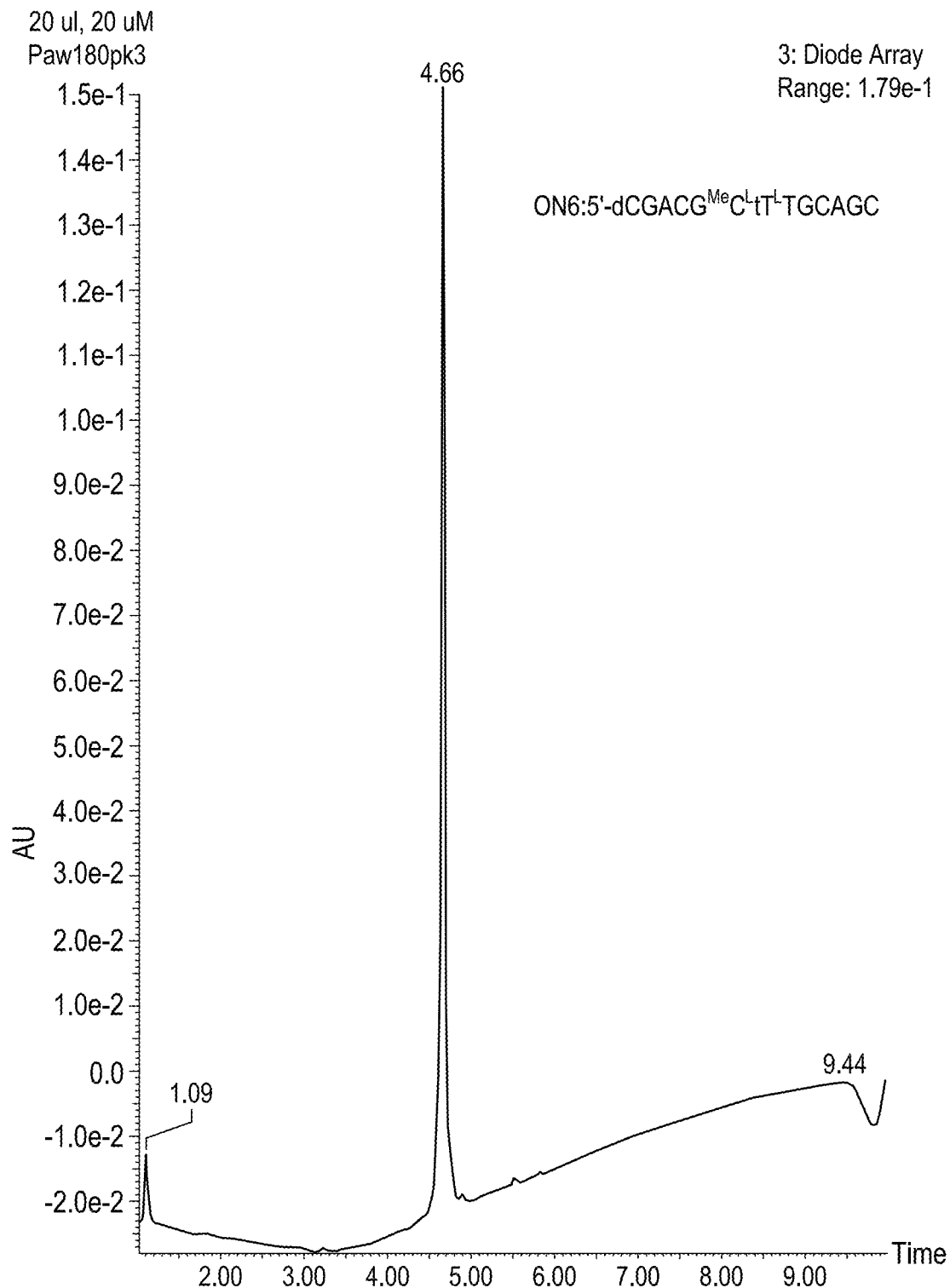
FIG. 12 shows the UV trace from HPLC of HPLC/mass spec for modified oligonucleotide ON6 (SEQ ID NO: 8): 5'-dCGACG $^{Me}$C$^L$tT$^L$TGCAGC.

FIG. 12 shows the UV trace from HPLC of HPLC/mass spec for modified oligonucleotide ON6 (SEQ ID NO: 8): 5'-dCGACG MeCLtTLTGCAGC.

Figure 13:
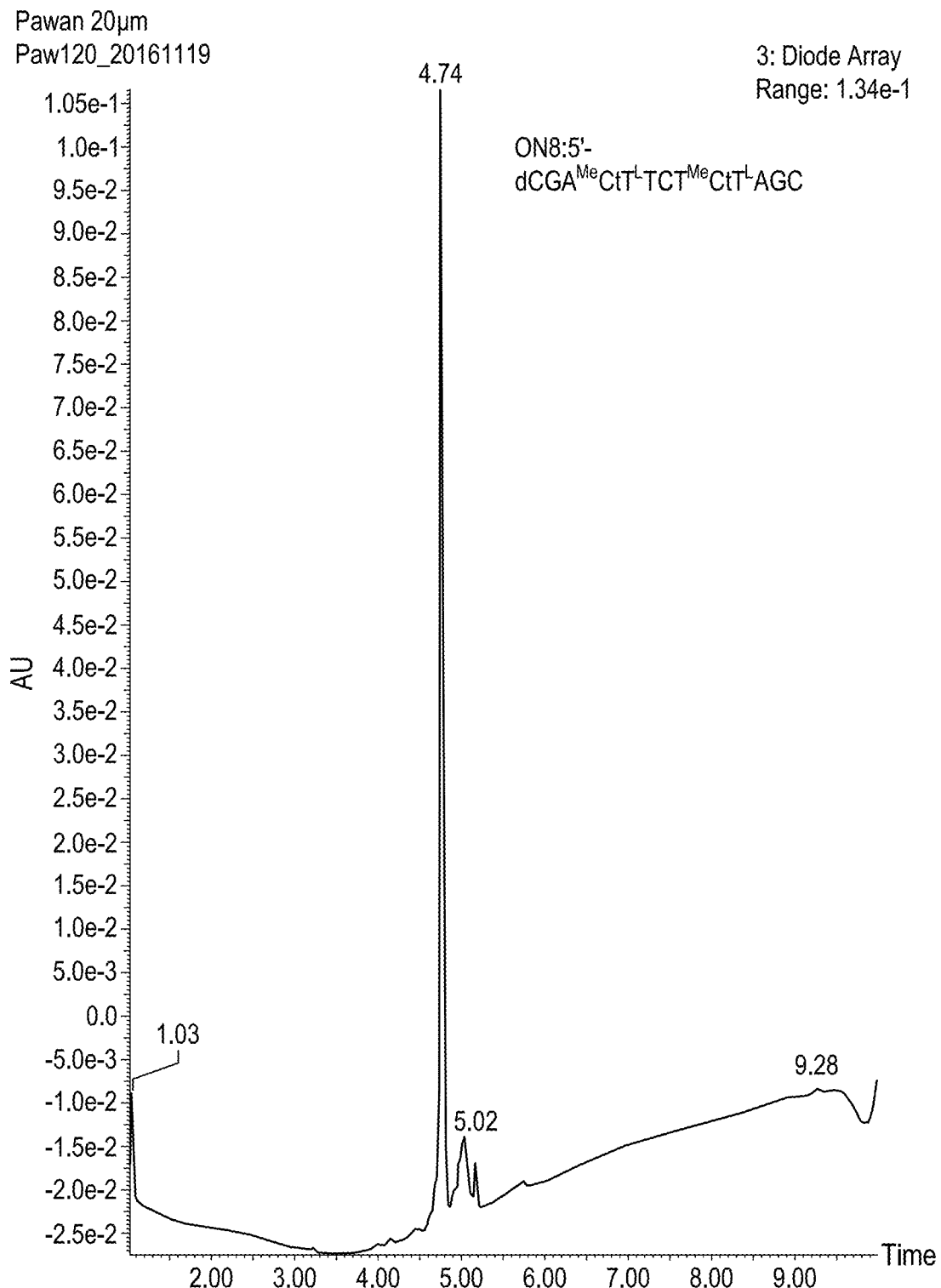
FIG. 13 shows the UV trace from HPLC of HPLC/mass spec for modified oligonucleotide ON8 (SEQ ID NO: 9): 5'-dCGA$^{Me}$CtT$^L$TCT$^{Me}$CtT$^L$AGC.

FIG. 13 shows the UV trace from HPLC of HPLC/mass spec for modified oligonucleotide ON8 (SEQ ID NO: 9): 5'-dCGAMeCtTLTCTMeCtTLAGC.

Figure 14:
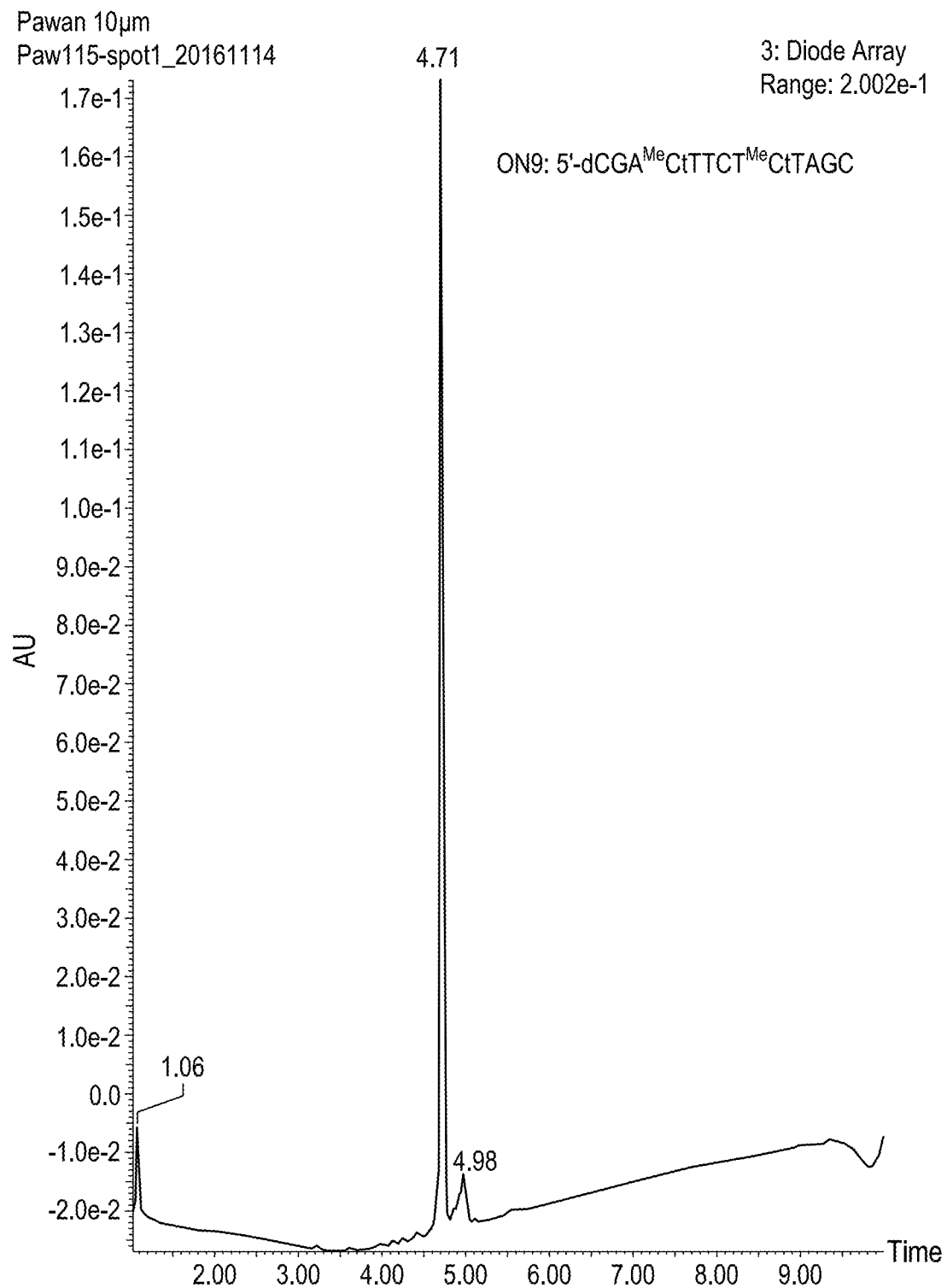
FIG. 14 shows the UV trace from HPLC of HPLC/mass spec for modified oligonucleotide ON9 (SEQ ID NO: 10): 5'-dCGA$^{Me}$CtTTCT$^{Me}$CtTAGC.

FIG. 14 shows the UV trace from HPLC of HPLC/mass spec for modified oligonucleotide ON9 (SEQ ID NO: 10): 5'-dCGAMeCtTTCTMeCtTAGC.

Figure 15:
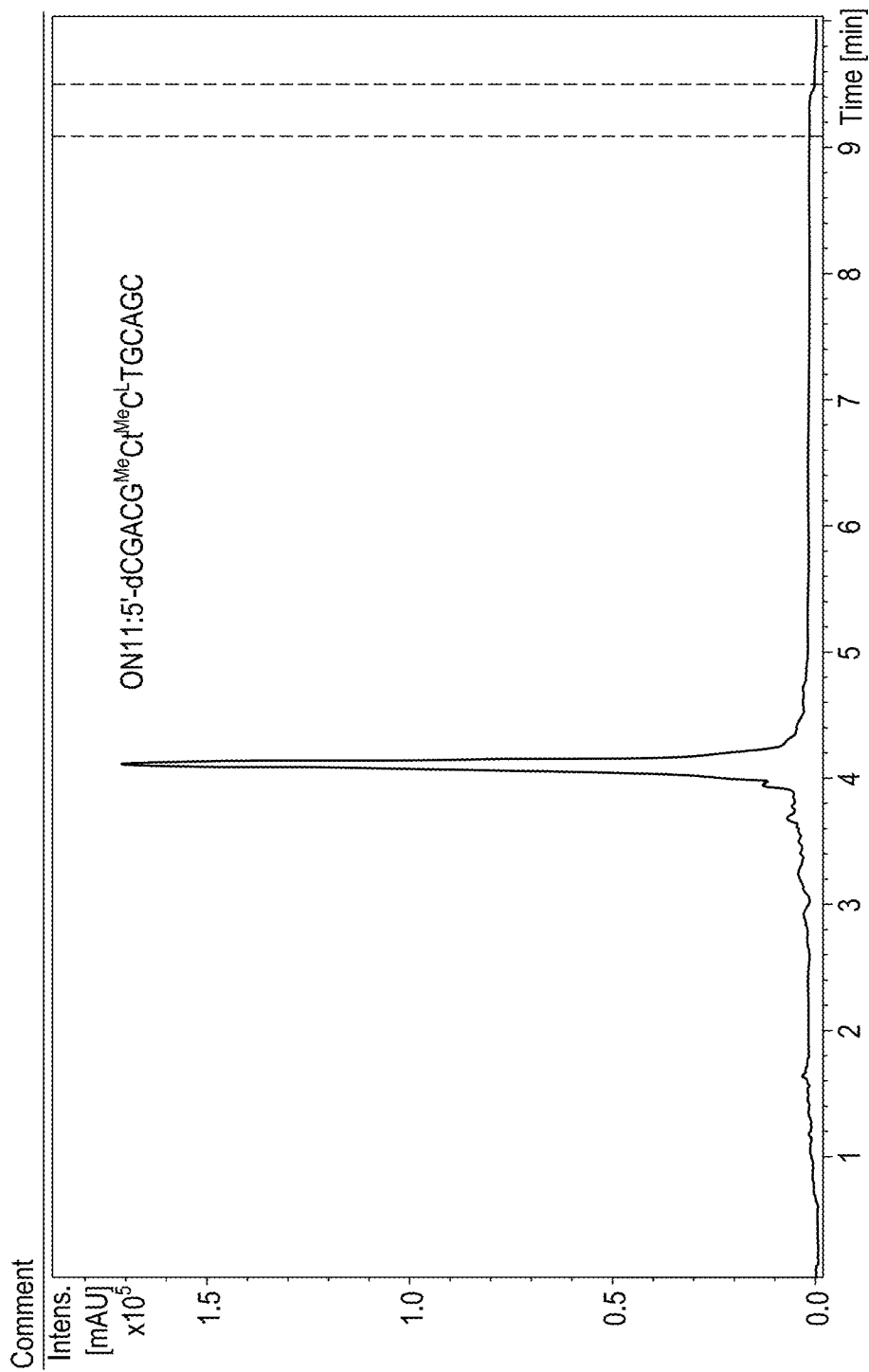
FIG. 15 shows the UV trace from HPLC of HPLC/mass spec for modified oligonucleotide ON11 (SEQ ID NO: 11): 5'-dCGACG $^{Me}$Ct$^{Me}$C$^L$TGCAGC.

FIG. 15 shows the UV trace from HPLC of HPLC/mass spec for modified oligonucleotide ON11 (SEQ ID NO: 11): 5'-dCGACG MeCtMeCLTGCAGC.

Figure 16:
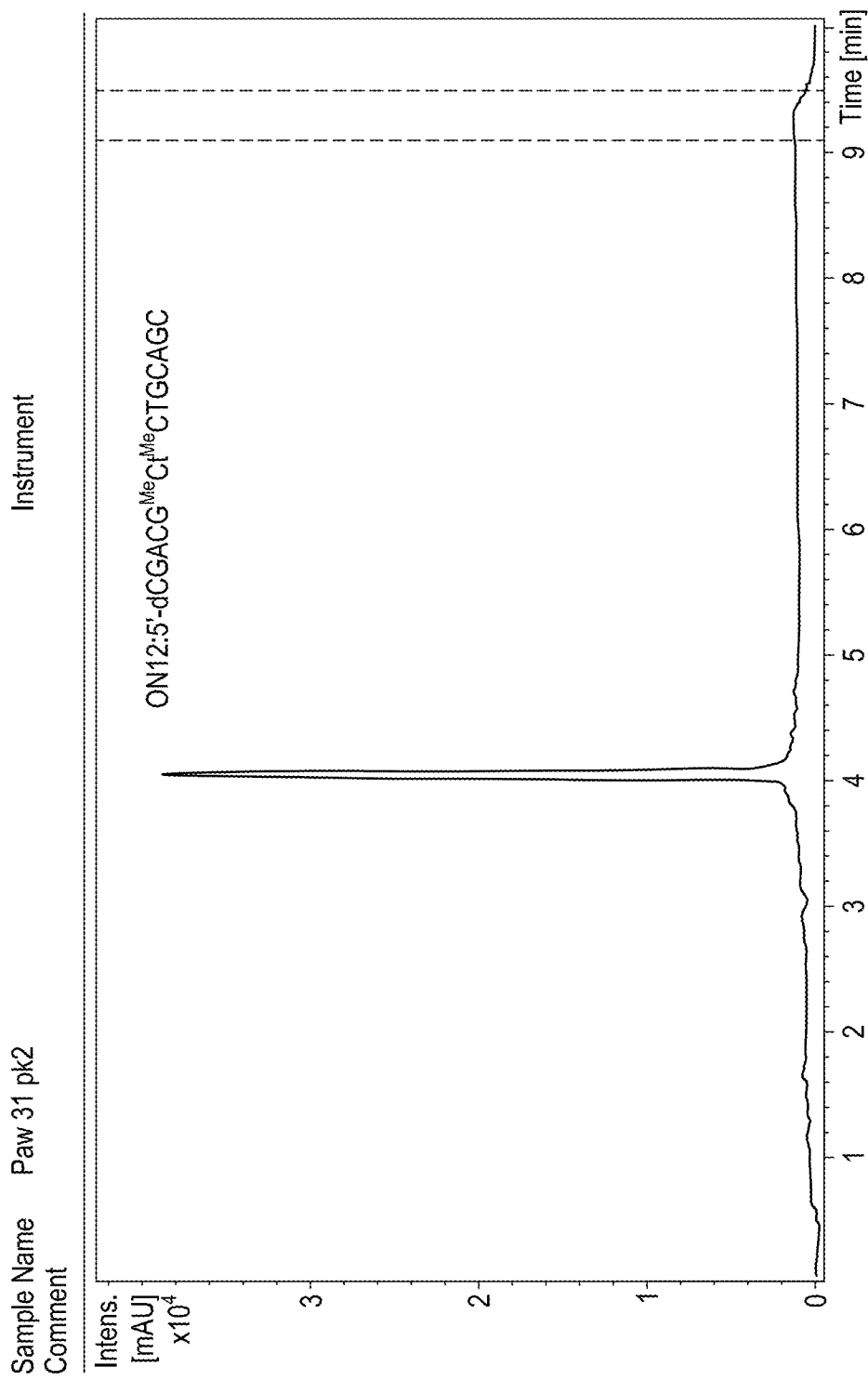
FIG. 16 shows the UV trace from HPLC of HPLC/mass spec for modified oligonucleotide ON12 (SEQ ID NO: 12): 5'-dCGACG $^{Me}$Ct$^{Me}$CTGCAGC.

FIG. 16 shows the UV trace from HPLC of HPLC/mass spec for modified oligonucleotide ON12 (SEQ ID NO: 12): 5'-dCGACG MeCtMeCTGCAGC.

Figure 17:
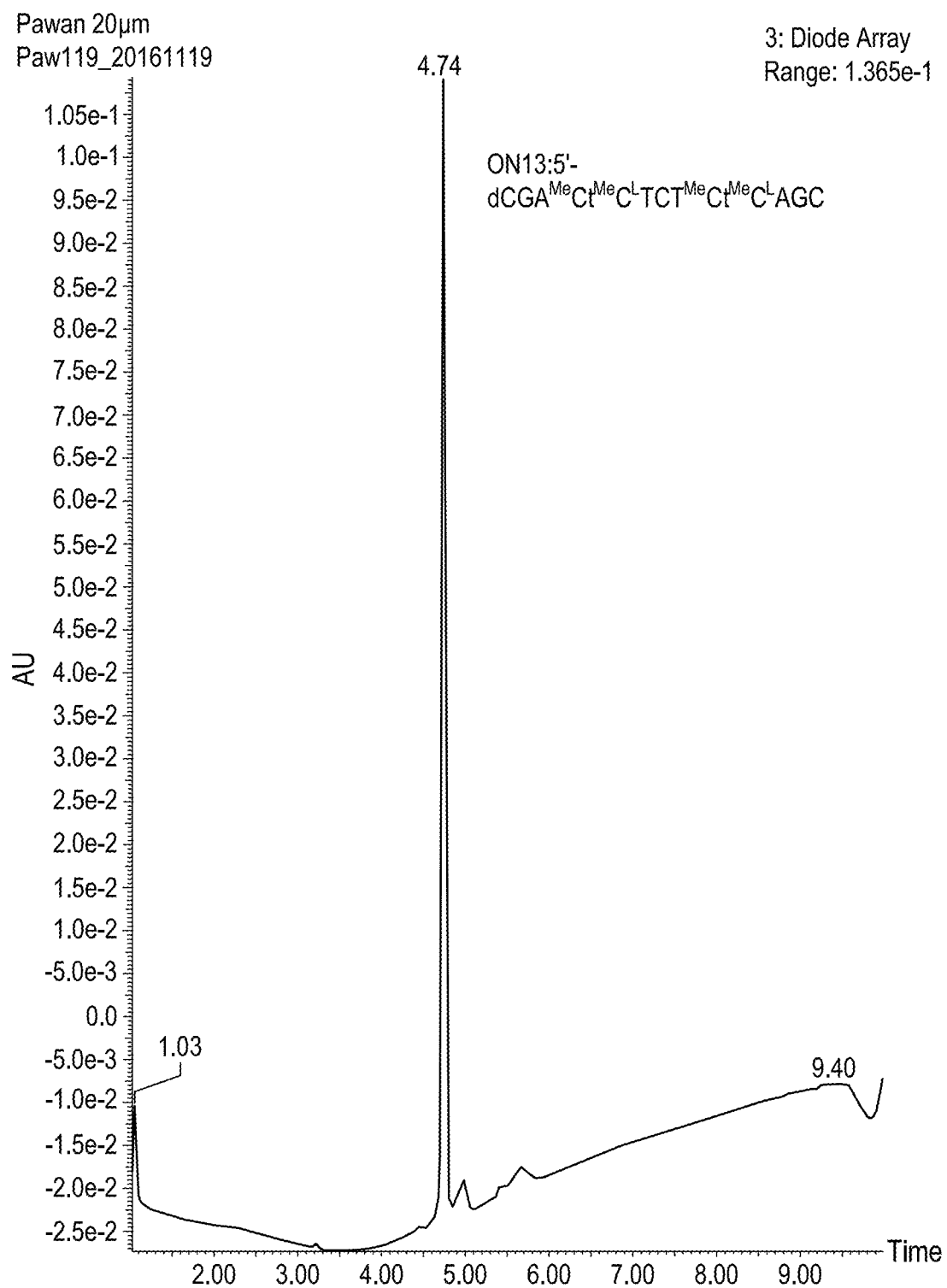
FIG. 17 shows the UV trace from HPLC of HPLC/mass spec for modified oligonucleotide ON13 (SEQ ID NO: 13): 5'-dCGA$^{Me}$Ct$^{Me}$C$^L$TCT$^{Me}$Ct$^{Me}$C$^L$AGC.

FIG. 17 shows the UV trace from HPLC of HPLC/mass spec for modified oligonucleotide ON13 (SEQ ID NO: 13): 5'-dCGAMeCtMeCLTCTMeCtMeCLAGC.

Figure 18:
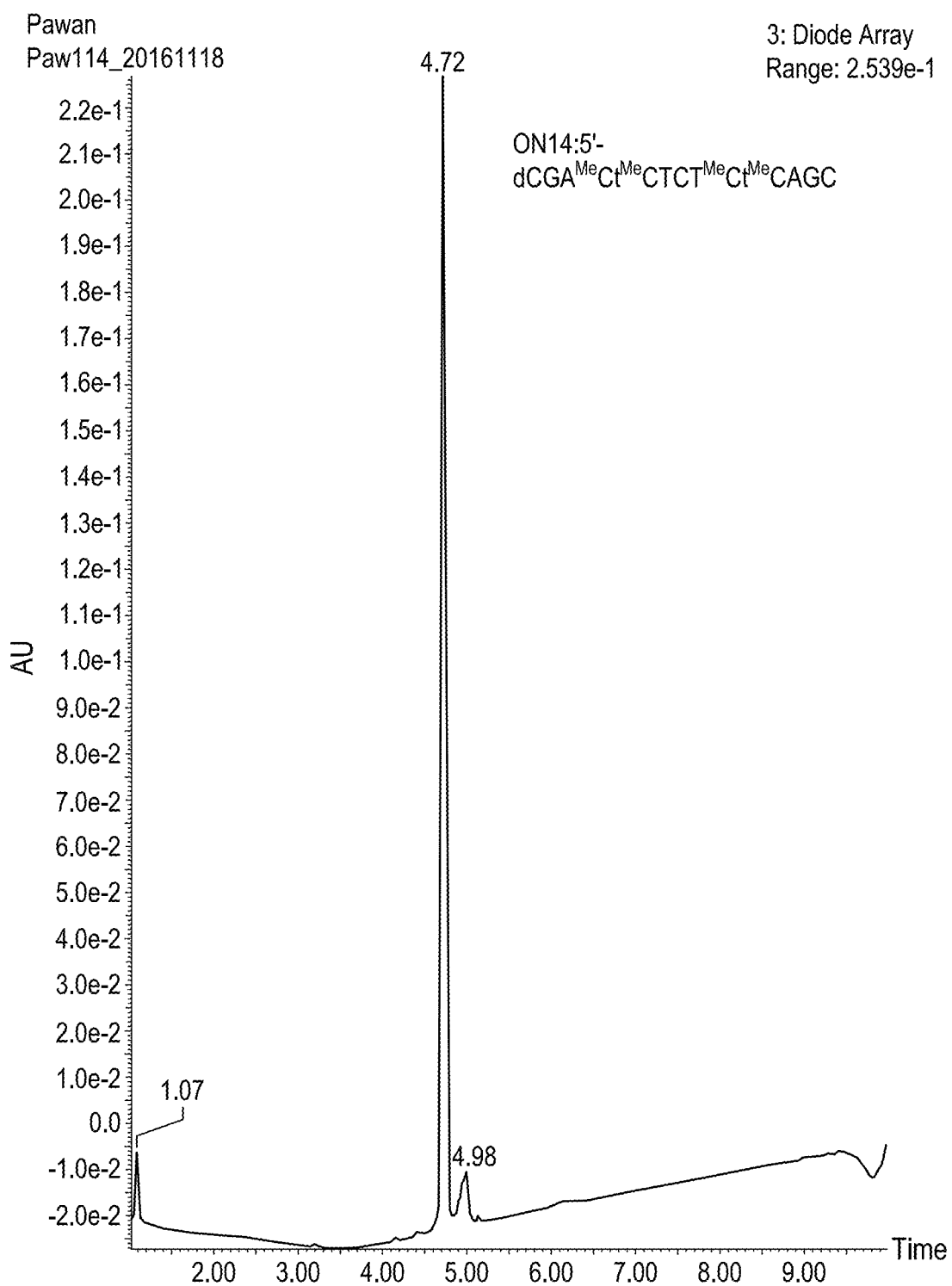
FIG. 18 shows the UV trace from HPLC of HPLC/mass spec for modified oligonucleotide ON14 (SEQ ID NO: 14): 5'-dCGA$^{Me}$Ct$^{Me}$CTCT$^{Me}$Ct$^{Me}$CAGC.

FIG. 18 shows the UV trace from HPLC of HPLC/mass spec for modified oligonucleotide ON14 (SEQ ID NO: 14): 5'-dCGAMeCtMeCTCTMeCtMeCAGC.

Figure 19:
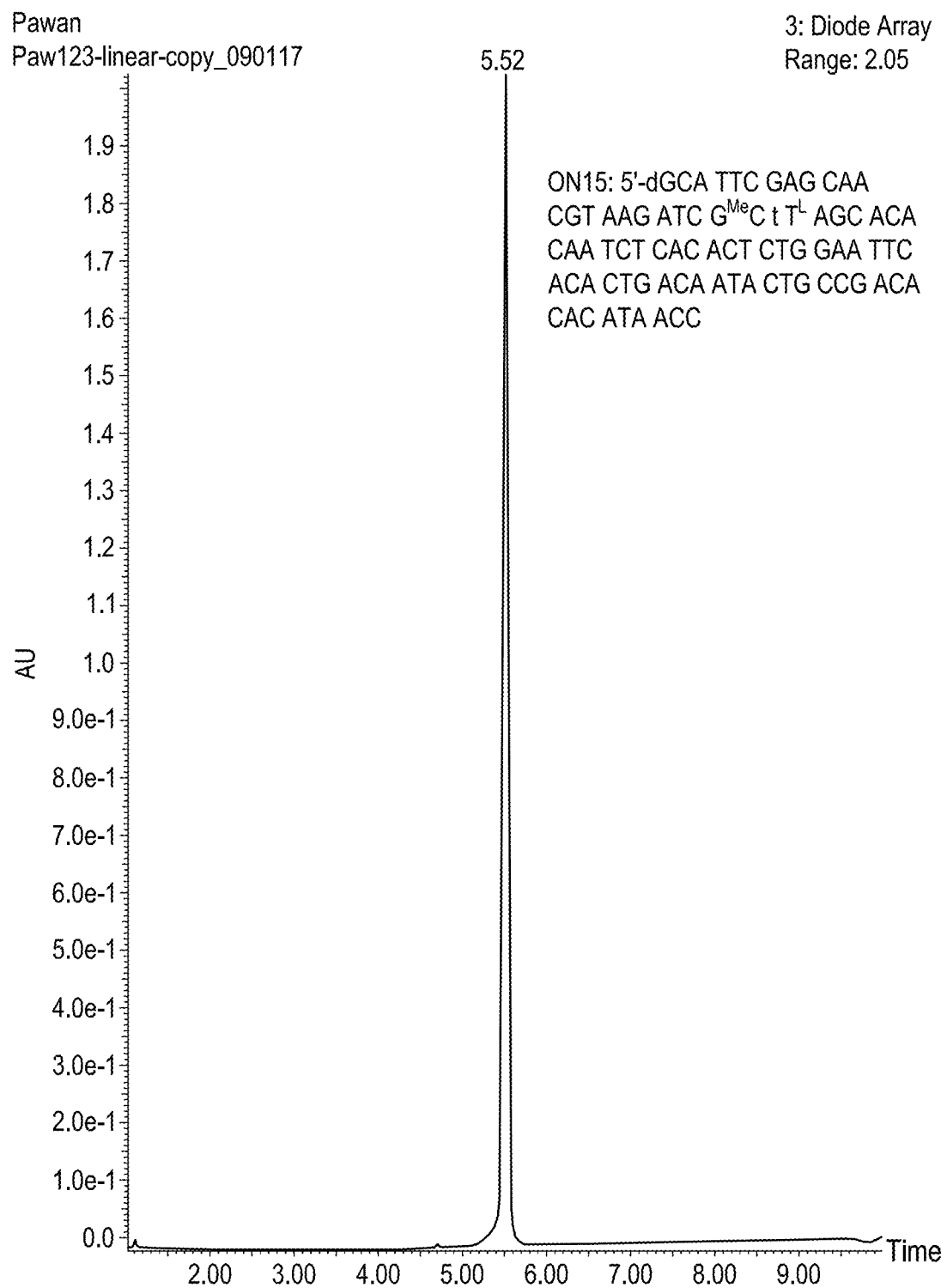
FIG. 19 shows the UV trace from HPLC of HPLC/mass spec for modified oligonucleotide ON15 (SEQ ID NO: 15): 5'-dGCA TTC GAG CAA CGT AAG ATC G $^{Me}$C t T$^L$ AGC ACA CAA TCT CAC ACT CTG GAA TTC ACA CTG ACA ATA CTG CCG ACA CAC ATA ACC.

FIG. 19 shows the UV trace from HPLC of HPLC/mass spec for modified oligonucleotide ON15 (SEQ ID NO: 15): 5'-dGCA TTC GAG CAA CGT AAG ATC G MeC t TL AGC ACA CAA TCT CAC ACT CTG GAA TTC ACA CTG ACA ATA CTG CCG ACA CAC ATA ACC.

Figure 20:
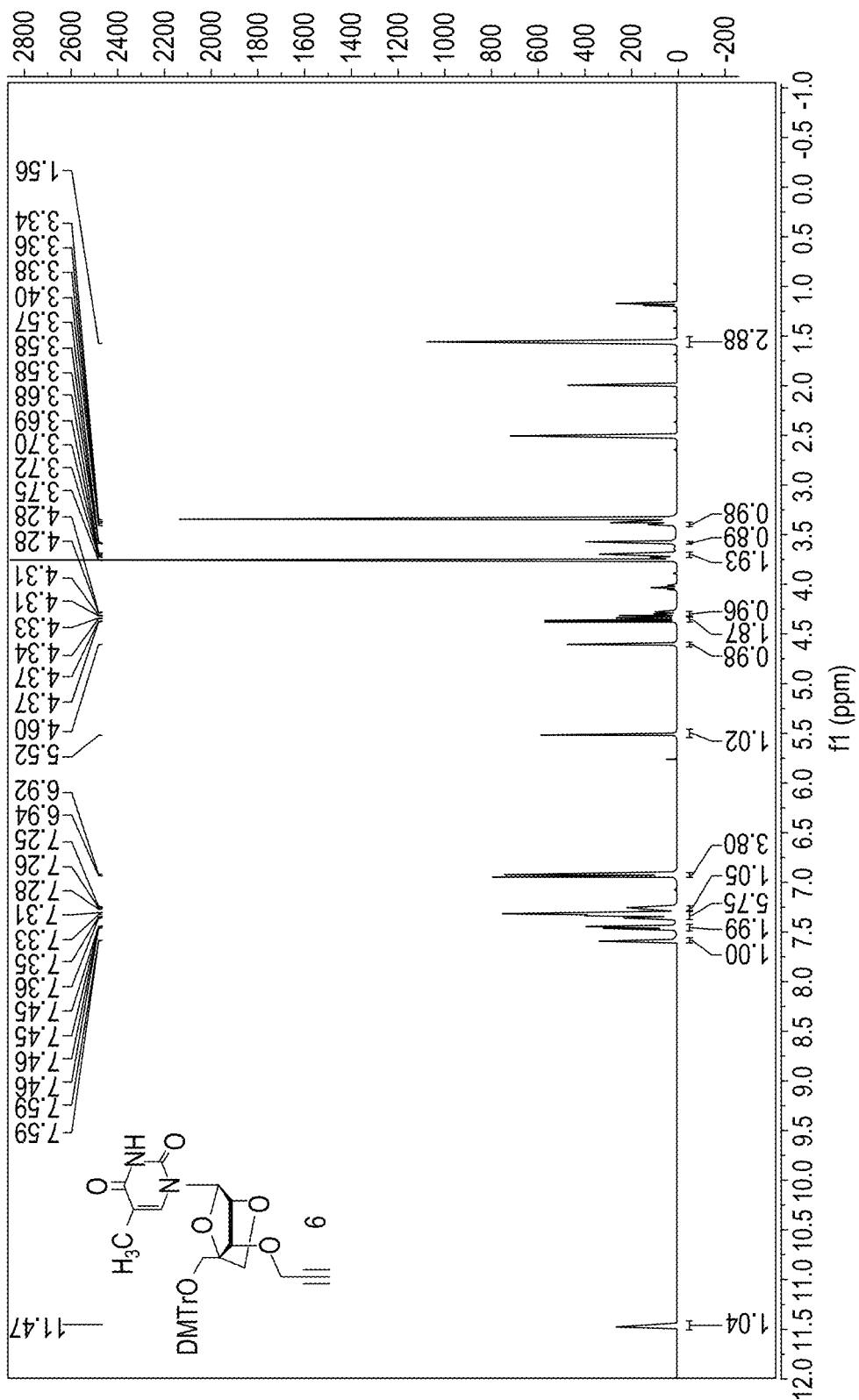
FIG. 20 shows the $^1$H NMR spectrum of 5'-O-(4,4'-dimethoxytrityl)-3'-O-propargyl-LNA thymidine (6).

FIG. 20 shows the $^1$H NMR spectrum of 5'-O-(4,4'-dimethoxytrityl)-3'-O-propargyl-LNA thymidine (6).

Figure 21:
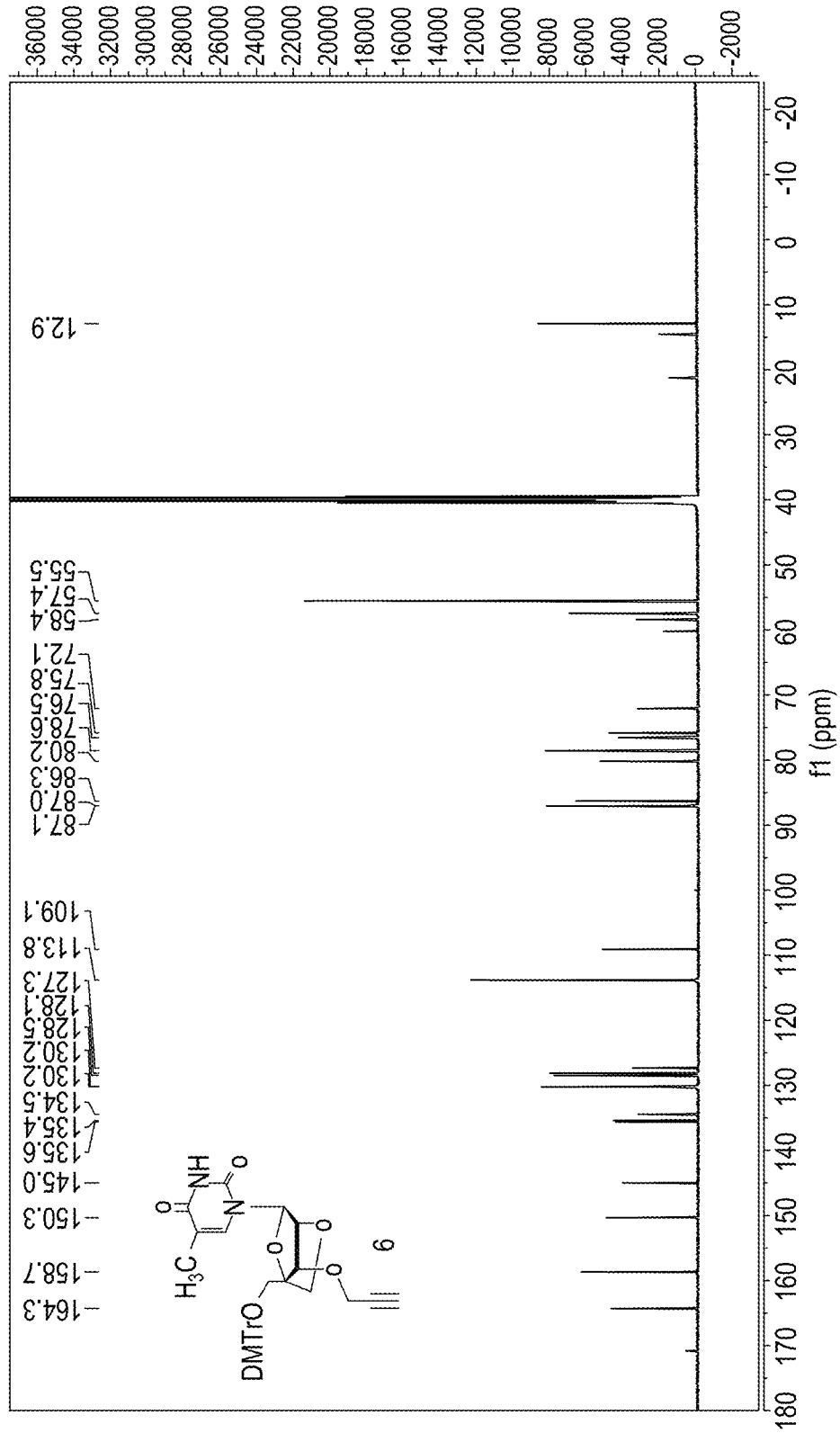
FIG. 21 shows the $^{13}$C NMR spectrum of 5'-O-(4,4'-dimethoxytrityl)-3'-O-propargyl-LNA thymidine (6).

FIG. 21 shows the $^{13}$C NMR spectrum of 5'-O-(4,4'-dimethoxytrityl)-3'-O-propargyl-LNA thymidine (6).

Figure 22:
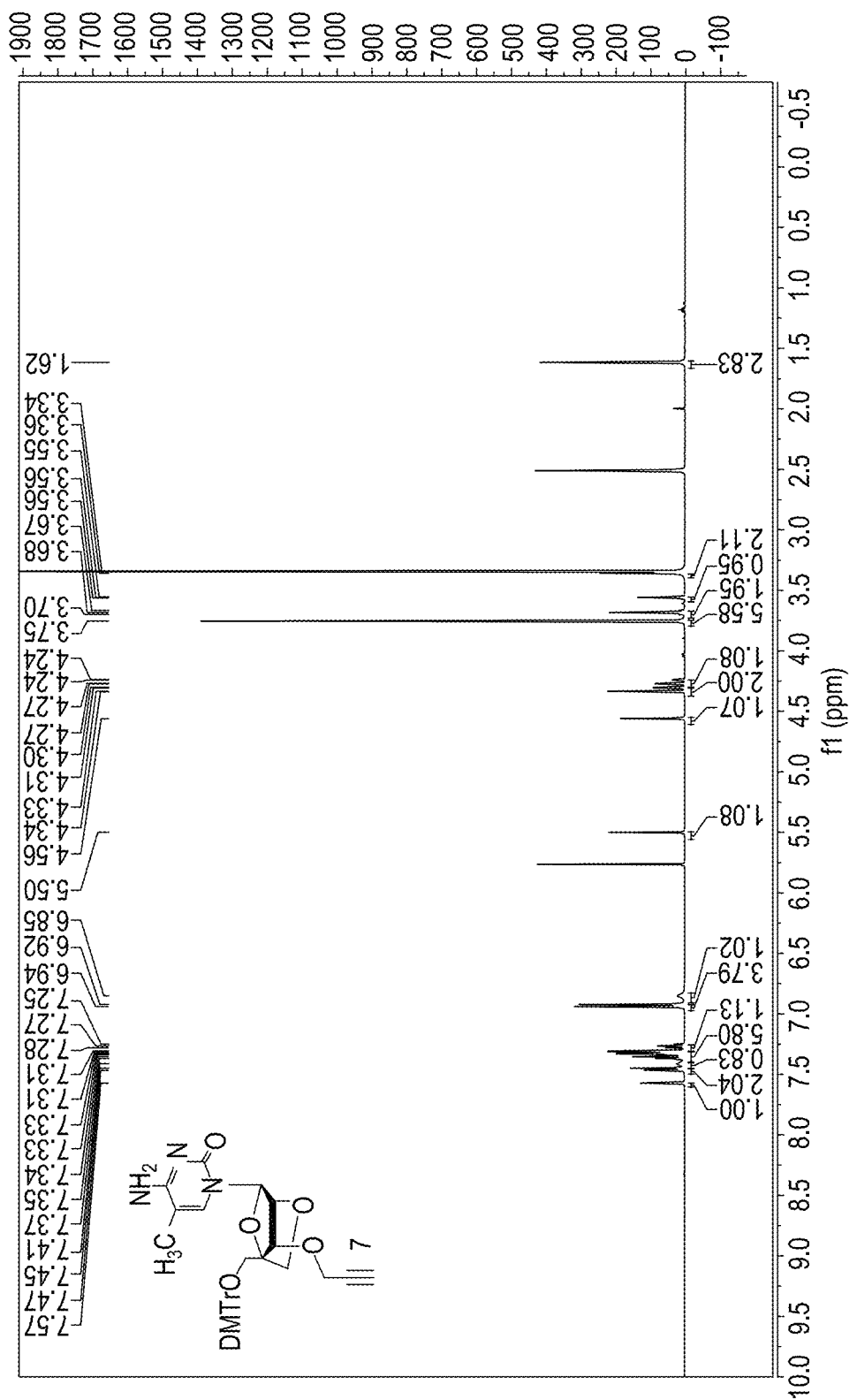
FIG. 22 shows the $^1$H NMR spectrum of 5'-O-(4,4'-dimethoxytrityl)-3'-O-propargyl-5-methyl LNA cytidine (7).

FIG. 22 shows the $^1$H NMR spectrum of 5'-O-(4,4'-dimethoxytrityl)-3'-O-propargyl-5-methyl LNA cytidine (7).

Figure 23:
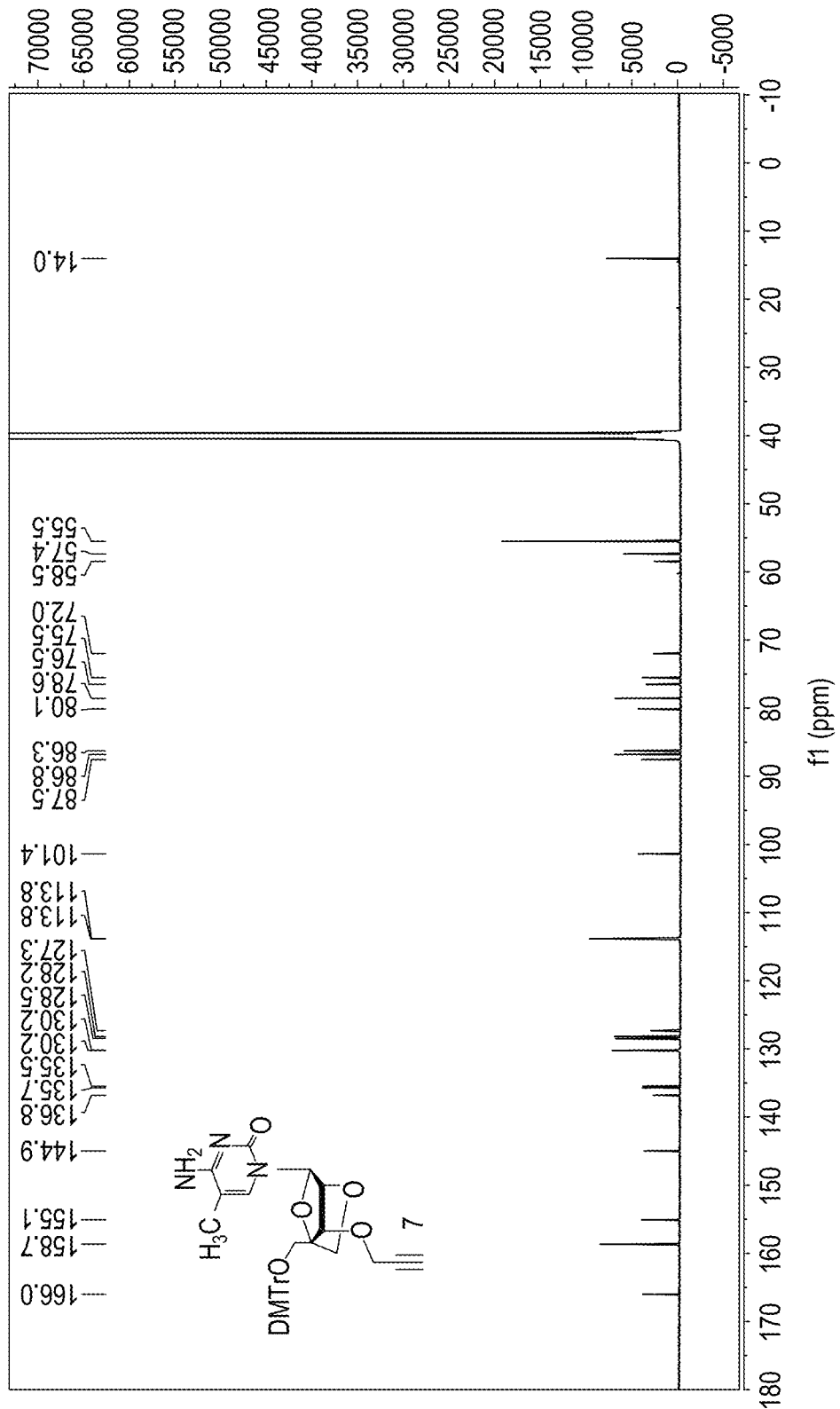
FIG. 23 shows the $^{13}$C NMR spectrum of 5'-O-(4,4'-dimethoxytrityl)-3'-O-propargyl-5-methyl LNA cytidine (7).

FIG. 23 shows the $^{13}$C NMR spectrum of 5'-O-(4,4'-dimethoxytrityl)-3'-O-propargyl-5-methyl LNA cytidine (7).

Figure 24:
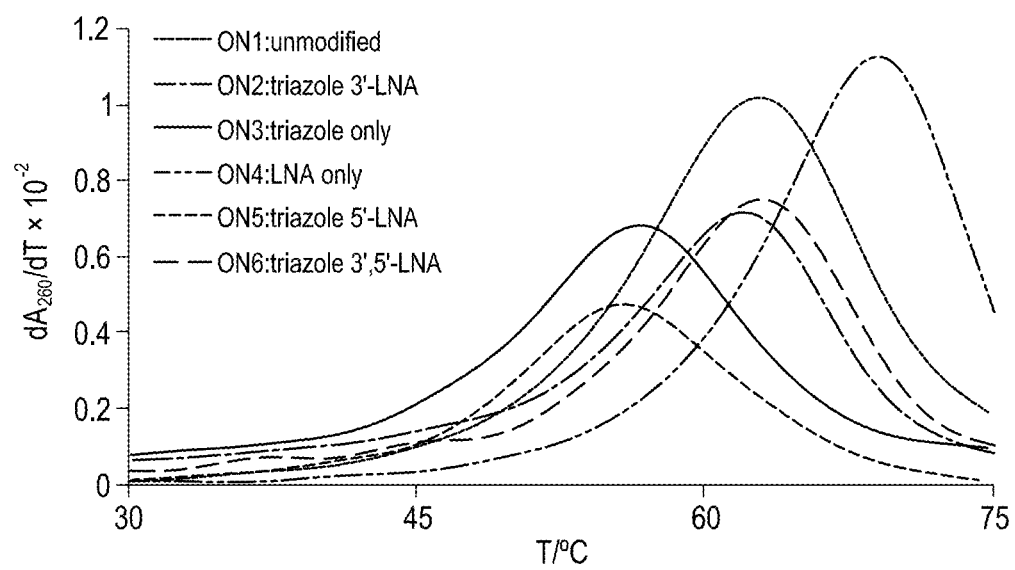
FIG. 24 shows the UV melting studies (derivatives of melting curves). DNA:RNA hybrid duplex containing a triazole linkage are stabilized by the introduction of LNA next to the triazole linkage (compare ON2 and ON3) For sequences see Table 8.

FIG. 24 shows the UV melting studies (derivatives of melting curves). DNA:RNA hybrid duplex containing a triazole linkage are stabilized by the introduction of LNA next to the triazole linkage (compare ON2 and ON3) For sequences see Table 8.

Figure 25:
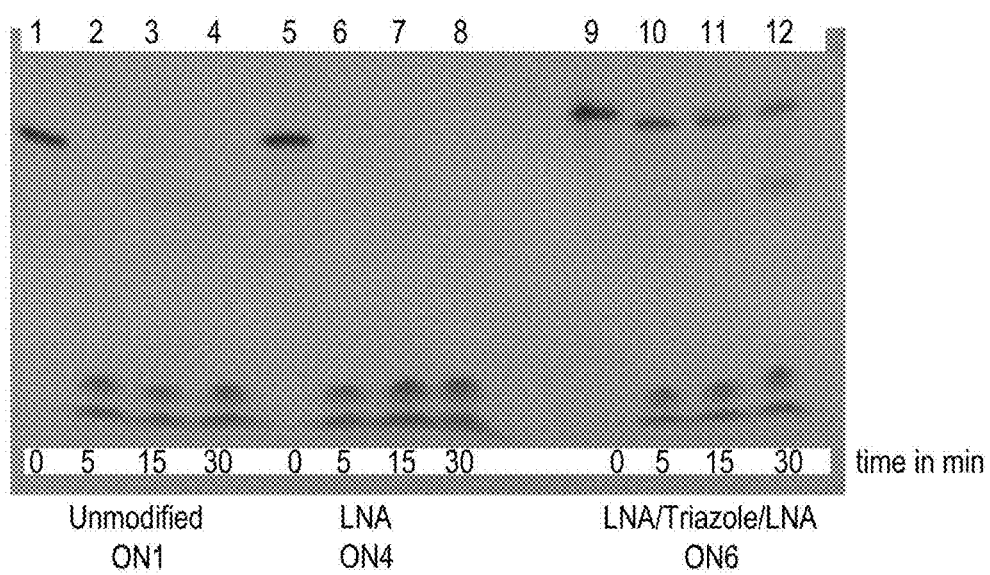
FIG. 25 shows LNA triazole stabilisation of oligonucleotides to 3'-exonuclease digestion. The unmodified ON (lanes 2-4) and LNA ON (lanes 6-8) were fully digested within 5 min whereas the LNA-triazole-LNA ON was still visible after 30 min (lane 12).

FIG. 25 shows LNA triazole stabilisation of oligonucleotides to 3'-exonuclease digestion. The unmodified ON (lanes 2-4) and LNA ON (lanes 6-8) were fully digested within 5 min whereas the LNA-triazole-LNA ON was still visible after 30 min (lane 12).

Figure 26:
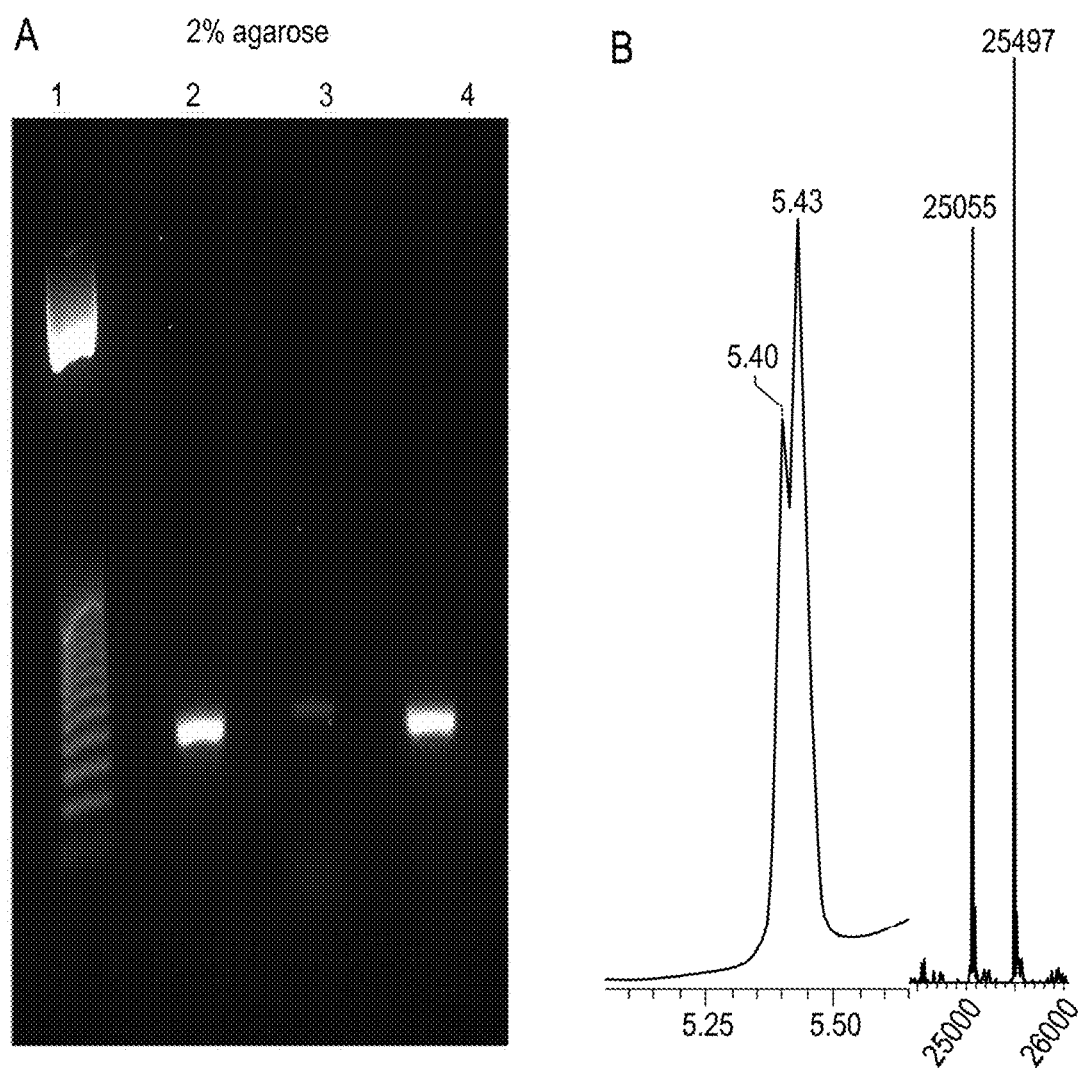
FIG. 26 shows LNA triazole DNA template is correctly amplified by PCR. A) 2% agarose gel using template GCA TTC GAG CAA CGT AAG ATC G$^{Me}$CtT$^L$ AGC ACA CAA TCT CAC ACT CTG GAA TTC ACA CTG ACA ATA CTG CCG ACA CAC ATA ACC (SEQ ID NO: 1) where t represent triazole linkage and T$^L$ is LNA thymidine. Lane 1; 25 bp ladder. Lane 2; PCR reaction using modified template. Lane 3; negative control, PCR reaction with primers but no template. Lane 4; positive control, PCR reaction with unmodified template. B) UV trace from HPLC of HPLC/mass spec and ESI mass spectrum of the PCR product (both strands). [M+A] strand 1: calc. 25053, found 25055. Strand 2: calc. 25496, found 25497.

FIG. 26 shows LNA triazole DNA template is correctly amplified by PCR. A) 2% agarose gel using template GCA TTC GAG CAA CGT AAG ATC GMeCtTL AGC ACA CAA TCT CAC ACT CTG GAA TTC ACA CTG ACA ATA CTG CCG ACA CAC ATA ACC (SEQ ID NO: 1) where t represent triazole linkage and TL is LNA thymidine. Lane 1; 25 bp ladder. Lane 2; PCR reaction using modified template. Lane 3; negative control, PCR reaction with primers but no template. Lane 4; positive control, PCR reaction with unmodified template. B) UV trace from HPLC of HPLC/mass spec and ESI mass spectrum of the PCR product (both strands). [M+A] strand 1: calc. 25053, found 25055. Strand 2: calc. 25496, found 25497.

Reference Synthetic Procedures

All reagents were purchased from Sigma-Aldrich, Alfa Aesar, Fisher Scientific, or Link Technologies and used without further purification. Pyridine (from KOH) and POCl$_3$ were freshly distilled before use, and THF was obtained using the MBraun SPS Bench Top solvent purification system (SPS). All air/moisture sensitive reactions were carried out under inert atmosphere (argon) in oven-dried glassware. Reactions were monitored by thin layer chromatography (TLC) using Merck Kieselgel 60 F24 silica gel plates (0.22 mm thickness, aluminium backed). The compounds were visualized by UV irradiation at 254/265 nm and by staining in p-anisaldehyde solution. Column chromatography was carried out under pressure (Flash Master Personal) using Biotage Isolute SPE columns. Columns were primed with CH$_2$Cl$_2$ containing 1% pyridine prior to use. $^1$H and $^{13}$C spectra were measured on a Bruker AVII 500 spectrometer at 500 MHz and 126 MHz, respectively. Chemical shifts are given in ppm and were internally referenced to the appropriate residual solvent signal, all coupling constants (J) are quoted in Hertz (Hz). Assignment of compounds was aided by COSY, HSQC, HMBC, and DEPT-135 experiments. High-resolution mass spectra were measured on a Bruker 9.4 FT-ICR-MS mass spectrometer, and samples were run in MeOH.

Synthesis of 5'-O-(4,4'-dimethoxytrityl)-3'-O-propargyl-LNA Thymidine (6)

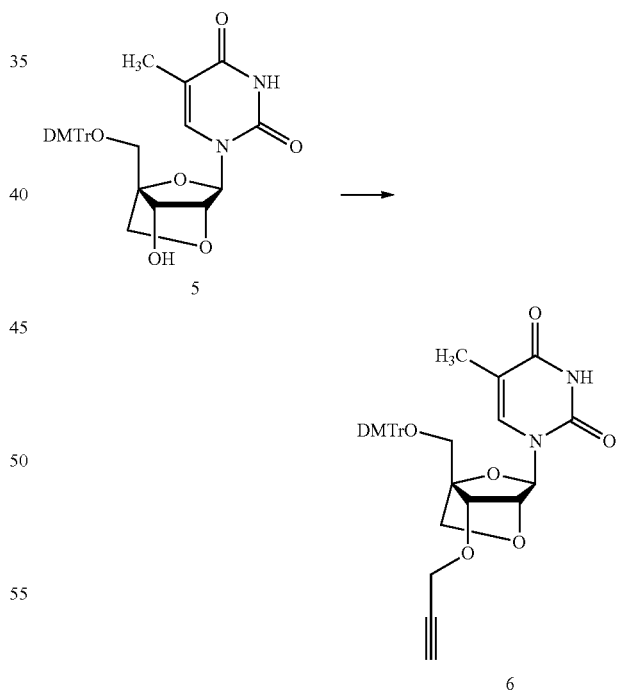

Nucleoside 5$^{S1}$ (2.00 g, 3.50 mmol) was co-evaporated with anhydrous THF (3×15 mL) and re-dissolved in anhydrous THF (24 mL). The solution was cooled to 0° C. and NaH (60% suspension in mineral oil, 0.348 g, 14.5 mmol) was added in portions over 5 min. The reaction mixture was stirred on ice for 30 min and at room temperature for 1 h. Propargyl bromide (0.374 mL, 4.20 mmol) was added at 0°

C. and the reaction was stirred on ice for 30 min and at room temperature for 16 h. Solvent was removed at reduced pressure and the residue was dissolved in EtOAc (100 mL) and washed with brine (2×50 mL). The organic phase was dried (Na$_2$SO$_4$) and concentrated and the resulting crude was purified using column chromatography (EtOAc in hexane, 10% to 80%, v/v) to obtain compound 6 (1.68 g, 2.75 mmol, 79%) as a white foam. R$_f$=0.4 (70% EtOAc in hexane, v/v). ESI HRMS m/z 633.2208 ([M+Na]$^+$, C$_{35}$H$_{34}$O$_8$N$_2$Na$^+$ calc. 633.2207. $^1$H NMR (500 MHz, DMSO-d$_6$) δ 11.47 (s, 1H, NH), 7.59 (d, J=1.1 Hz, 1H, H-6), 7.46-7.45 (m, 2H, DMTr), 7.36-7.31 (m, 6H, DMTr), 7.28-7.25 (m, 1H, DMTr), 6.93 (d, J=8.8 Hz, 4H, DMTr), 5.52 (s, 1H, H-1'), 4.60 (s, 1H, H-2'), 4.37-4.32 (m, 2H, H-3', CH$_2$—C≡CH), 4.29 (dd, J=15.9, 2.4 Hz, 1H, CH$_2$—C≡CH), 3.75 (s, 6H, OCH$_3$), 3.72-3.70 (d, J=8.0 Hz, 1H, H-5''), 3.69-3.68 (d, J=8.0 Hz, 1H, H-5''), 3.58 (t, J=2.4 Hz, 1H, C≡CH), 3.39 (d, J=11.8 Hz, 1H, H-5'), 3.36-3.34 (m, 1H, H-5', merged with H$_2$O signal from DMSO-d$_6$), 1.56 (d, J=1.1 Hz, 3H, CH$_3$). $^{13}$C NMR (126 MHz, DMSO) δ 164.3 (C4), 158.7 (DMTr), 150.3 (C2), 145.0, 135.6, 135.4 (DMTr), 134.5 (C6), 130.25, 130.18, 128.5, 128.1, 127.3, 113.8 (DMTr), 109.1 (C5), 87.1 (C4'), 87.0 (C1'), 86.3 (DMTr), 80.2 (C≡CH), 78.6 (C≡CH), 76.5 (C2'), 75.8 (C3'), 72.1 (C5''), 58.4 (C5'), 57.4 (CH$_2$—C≡CH), 55.5 (OCH$_3$), 12.9 (CH$_3$).

Synthesis of 5'-O-(4,4'-dimethoxytrityl)-3'-O-propargyl-5-methyl LNA Cytidine (7)

Nucleoside 6 (0.408 g, 0.668 mmol) was co-evaporated with anhydrous pyridine (3×10 mL) and re-dissolved in anhydrous pyridine (5 mL). The solution was cooled to 0° C. and N-methylimidazole (0.7 mL, 8.8 mmol) was added. The reaction mixture was stirred at 0° C. for 15 min, whereupon a freshly distilled POCl$_3$ (0.25 mL, 2.7 mmol) was added dropwise. The reaction was stirred at 0° C. for 30 min and then at room temperature for an additional 30 min Concentrated aqueous ammonia (5 mL) was added and the reaction was stirred at room temperature for 16 h. The solvents were removed under reduced pressure. The residue was dissolved in CH$_2$Cl$_2$ (50 mL) and washed with brine (2×30 mL). The aqueous phase was back extracted with CH$_2$Cl$_2$ (2×30 mL). The combined organic phase was dried (Na$_2$SO$_4$), and concentrated under reduced pressure. The crude was then purified using column chromatography (0% to 7% MeOH/CH$_2$Cl$_2$) to obtain nucleoside 7 (0.233 g, 0.382 mmol, 57%) as a white foam. R$_f$=0.5 (8% MeOH in CH$_2$Cl$_2$, v/v). ESI HRMS m/z 608.2406 ([M−H]$^−$, C$_{35}$H$_{34}$O$_7$N$_3$$^−$ calc. 608.2402. $^1$H NMR (500 MHz, DMSO-d$_6$) δ 7.57 (s, 1H, H-6), 7.47-7.45 (m, 2H, DMTr), 7.41 (broad s, 1H, N—H), 7.37-7.31 (m, 6H, DMTr), 7.28-7.25 (m, 1H, DMTr), 6.93 (d, J=8.8 Hz, 4H, DMTr), 6.85 (broad s, 1H, NH), 5.50 (s, 1H, H-1'), 4.56 (s, 1H, H-2'), 4.34-4.30 (m, 2H, H-3', CH$_2$—C≡CH), 4.25 (dd, J=16.0 Hz, 2.4 Hz, 1H, CH$_2$—C≡CH), 3.75 (s, 6H, OCH$_3$), 3.68 (s, 2H, H-5''), 3.56 (t, J=2.4 Hz, 1H, C≡CH), 3.36 (s, 2H, H-5', merged with H$_2$O signal from DMSO-d$_6$), 1.62 (s, 3H, CH$_3$). $^{13}$C NMR (126 MHz, DMSO) δ 166.0 (C4), 158.7 (DMTr), 155.1 (C2), 144.9 (DMTr), 136.8 (C6), 135.7, 135.5, 130.25, 130.18, 128.5, 128.2, 127.3, 113.83, 113.81 (DMTr), 101.4 (C5), 87.5 (C1'), 86.8 (C4'), 86.3 (DMTr), 80.1 (C≡CH), 78.6 (C≡CH), 76.5 (C2'), 75.5 (C3'), 72.0 (C5''), 58.5 (C5'), 57.4 (CH$_2$—C≡CH), 55.5 (OCH$_3$), 14.0 (CH$_3$).

Preparation of solid support carrying 5'-O-(4,4'-dimethoxytrityl)-3'-O-propargyl-5-methyl LNA Cytidine (8)

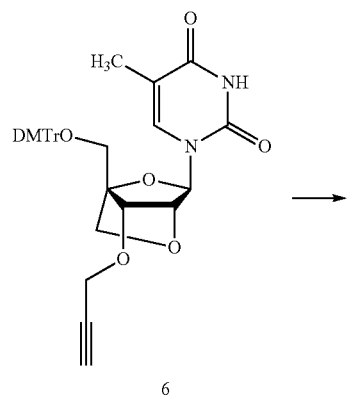

6

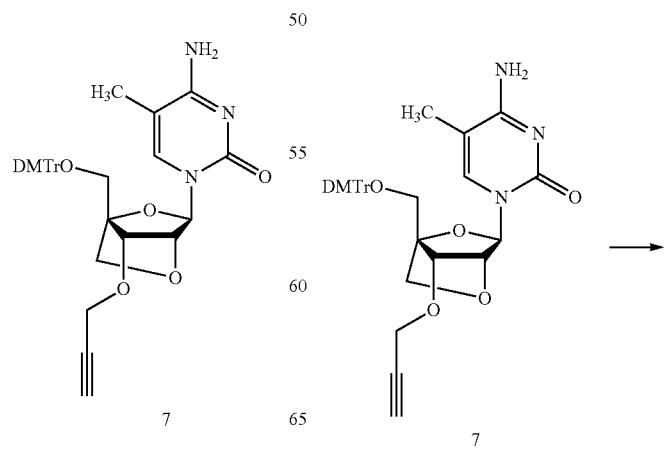

7

-continued

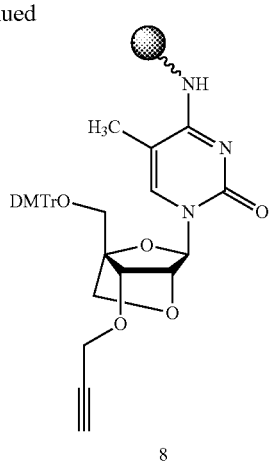

8

Amino-SynBase resin 500/100 (Link Technologies, Glasgow, UK) (500 Å pore size, loading 69 µmol/g, 4.06 g, 0.28 mmol of amine) was activated using 3% solution of trichloroacetic acid in $CH_2Cl_2$ for 3 h in a stoppered glass vessel fitted with a sinter and tap. The solvents were removed by filtration and the support was washed with triethylamine:diisopropylethylamine (9:1), $CH_2Cl_2$, and diethyl ether. The support was dried under vacuum for 1 h and re-suspended in anhydrous pyridine (10 mL). A solution of succinic anhydride (0.813 g, 8.13 mmol) and DMAP (160 mg, 1.3 mmol) in anhydrous pyridine (5 mL) was added and the vessel was rotated at room temperature for 20 h. The solvents were removed by filtration, and the support was washed with pyridine, $CH_2Cl_2$, and diethyl ether and dried under high vacuum for 1 h. 500 mg of the activated resin was taken forward and soaked in 1 mL of anhydrous pyridine for 10 min. Diisopropyl carbodiimide (DIC) (93 µL, 0.60 mmol), 1-hydroxybenzotriazole (HOBT) (93 µL, 0.69 mmol), and compound 7 (86 mg, 0.14 mmol) were added to the reaction vessel, and the vessel was rotated for 20 h at room temperature. Pentachlorophenol (45 mg, 0.17 mmol) was added, and the vessel was rotated for an additional 3 h. The solvents were removed by filtration, and the support was washed with pyridine, $CH_2Cl_2$, and diethyl ether. Piperidine (10% in DMF, 2 mL) was added and the vessel was rotated for 5 min at room temperature. The solvent was removed by filtration and the support was washed with $CH_2Cl_2$ and diethyl ether. Capping reagent (oligonucleotide synthesis grade, acetic anhydride/pyridine/THF:N-methylimidazole in THF, 1:1, 2 mL) was added and the vessel was rotated at room temperature for 1 h. The solvent was removed by filtration, and the resin was washed with pyridine, $CH_2Cl_2$, and diethyl ether and dried under high vacuum overnight. Loading of nucleoside 7 on the support determined by cleaving the DMT group and was found to be 26 µmol/g.

Synthesis and Purification of Oligonucleotides

Synthesis of DNA Oligonucleotides

Standard DNA phosphoramidites, solid supports and reagents were purchased from Link Technologies and Applied Biosystems. LNA phosphoramidites were obtained from Exiqon. Automated solid phase synthesis of oligonucleotides (trityl off) was performed on an Applied Biosystems 394 synthesiser. Synthesis was performed on 1.0 µmole scale involving cycles of acid-catalyzed detritylation, coupling, capping, and iodine oxidation. Standard DNA phosphoramidites were coupled for 60 s while extended coupling time of 10 min was used for LNA phosphoramidites. Coupling efficiencies and overall synthesis yields were determined by the inbuilt automated trityl cation conductivity monitoring facility and were >98.0% in all cases. The oligonucleotides were then cleaved from the solid support and protecting groups from the nucleobase and backbone were removed by exposure to concentrated aqueous ammonium hydroxide for 60 min at room temperature followed by heating in a sealed tube for 5 h at 55° C.

Synthesis of RNA Oligonucleotides

2'-TBS protected RNA phosphoramidite monomers with t-butylphenoxyacetyl protection of the A, G and C nucleobases were used to assemble RNA oligonucleotides. Benzylthiotetrazole (BTT) was used as the coupling agent, t-butylphenoxyacetic anhydride as the capping agent and 0.1 M iodine as the oxidizing agent (Sigma-Aldrich). Coupling time of 10 min was used and coupling efficiencies of >97% were obtained. Cleavage of oligonucleotides from the solid support and protecting groups from the nucleobase and backbone were removed by exposure to concentrated aqueous ammonia/ethanol (3/1 v/v) for 2 h at room temperature followed by heating in a sealed tube for 2 h at 55° C.
Removal of 2'-TBS Protection of RNA Oligonucleotides After cleavage from the solid support and removal of the protecting groups from the nucleobases and phosphodiesters in ammonia/ethanol as described above, oligonucleotides were concentrated to a small volume in vacuo, transferred to 15 mL plastic tubes and freeze dried (lyophilised). The residue was dissolved in DMSO (300 µL) and triethylamine trihydrofluoride (300 µL) was added after which the reaction mixtures were kept at 65° C. for 2.5 h. Sodium acetate (3 M, 50 µL) and butanol (3 mL) were added with vortexing and the samples were kept at −80° C. for 30 min then centrifuged at 13,000 rpm at 4° C. for 10 min. The supernatant was decanted and the precipitate was washed twice with ethanol (0.75 mL) then dried under vacuum.
Purification of Oligonucleotides (DNA or RNA)

The fully deprotected oligonucleotides were then purified by reverse-phase high performance liquid chromatography (HPLC) on a Gilson system using a Luna 10 µm C8(2) 100 Å pore Phenomenex column (250×10 mm) with a gradient of acetonitrile in triethylammonium bicarbonate (TEAB) over 20 min at a flow rate of 4 mL per minute. Buffer A: 0.1 M TEAB, pH 7.5; buffer B: 0.1 M TEAB, pH 7.5, with 50% acetonitrile were used. Elution was monitored by UV absorption between 260-295 nm.

Synthesis of 3'-alkyne-5-methyl dC Oligonucleotides and 3'-alkyne-5-methyl LNA-C Oligonucleotides 3'-Alkyne-5-methyl dC oligonucleotides were synthesized on 1.0 µmole scale using 5'-O-(4,4'-dimethoxytrityl)-3'-O-propargyl-5-methyldeoxycytidine solid support (33 µmole/g loading on AM polystyrene, Applied Biosystems).[52] The resin was packed into a twist column and the desired oligonucleotides were assembled and purified by standard phosphoramidite oligonucleotide synthesis (described above). 3'-Alkyne-5-methyl LNA-C oligonucleotides were synthesized by a similar procedure using the solid support 8. Purified oligonucleotides were characterised by electrospray mass spectrometry. Mass spectra of oligonucleotides were recorded either using a Bruker micrO- TOF™ II focus ESI-TOF MS instrument in ES⁻ mode or a XEVO G2-QTOF MS instrument in ES⁻ mode (Table 4).

Synthesis of 5'-azide Modified Oligonucleotides

Trityl off oligonucleotides were assembled at 1.0 μmole scale and were treated with a 0.5 M solution of methyltriphenoxyphosphonium iodide in DMF (1.0 mL) while attached to the solid support in a synthesis column.[S3] The solution was periodically passed through the column using two 1 mL syringes for 20 min at room temperature. The resin was then washed several times with DMF. In a separate vessel 50 mg of sodium azide was taken up in 1 mL DMF and heated to 70° C. for 10 min. The mixture was allowed to cool to room temperature and the supernatant was passed back and forth through the synthesis column using two 1 mL syringes.[S4] The synthesis column was left at 55° C. for 5 h and during this time the solution was occasionally passed back and forth. The column was then washed with DMF followed by acetonitrile and dried by the passage of a stream of argon. The resultant 5'-azide oligonucleotide was cleaved from solid support and deprotected by exposure to concentrated aqueous ammonium hydroxide for 60 min at room temperature followed by heating in a sealed tube for 5 h at 55° C. and purified as described above. Purified oligonucleotides were then characterised by mass spectrometry (Table 4).

Synthesis of 13-Mer Oligonucleotides Incorporating a Single Triazole Linkage

Representative Procedure

A mixture of 5'-azide oligonucleotide (130 nm) and 3'-alkyne oligonucleotide (100 nm) was freeze dried and re-dissolved in milli-Q water (250 μL). The solution was flushed with a stream of argon and to this was added an aqueous solution of CuSO₄ (20 μL, 100 mM), an aqueous solution of sodium ascorbate (40 μL, 500 mM), and tris-hydroxypropyltriazole ligand[S5] (5 mg). The resulting mixture was degassed with a stream of argon and left at room temperature for 2 h with occasional shaking. Reagents were then removed by NAP-10 gel-filtration and the ligated triazole oligonucleotide was purified by HPLC (as described above) and characterized by mass spectrometry (Table 4).

Synthesis of 13-Mer Oligonucleotides Incorporating Two Triazole Linkages

Representative Procedure

A 5'-azide oligonucleotide, a 3'-alkyne oligonucleotide, a 5'-azide-3'-alkyne oligonucleotide and a splint (40 nm each) were mixed with NaCl (200 μL, 3 M). Milli-Q water was added to raise the total volume to 1940 μL. The mixture was annealed by heating to 80° C. and then cooling slowly to room temperature. The content was then kept at 4° C. for 1 h. CuSO₄ (aqueous, 20 μL, 100 mM), sodium ascorbate (aqueous, 40 μL, 500 mM), and tris-hydroxypropyltriazole ligand[5] (4 mg) were added. Thus a final concentration of 20 μM of each oligo in 300 mM NaCl and a final volume of 2 mL was obtained. The reaction mixture was left at 4° C. for 3 h and then at room temperature for 1 h. Reagents were then removed by NAP-10 gel-filtration and the ligated triazole oligonucleotide was purified by denaturing 20% polyacrylamide gel electrophoresis and characterized by mass spectrometry (Table 4). Splint used: 5'-dTTTTTT GCTAGAGAAGTCG TTTTTT (SEQ ID NO: 26) (For ON8 and ON9), 5'-dTTTTTTGCTGGAGAGGTCGTTTTTT (SEQ ID NO: 27) (for ON13 and ON14).

Synthesis of an 81-Mer Template Incorporating a Single LNA-Triazole Linkage

ON32 and ON18 (Table 4, 70 nm of each) and a splint (70 nm) were mixed with NaCl (200 μL, 3 M) and total volume was brought to 1940 μL by the addition of milli-Q water. The mixture was annealed by heating to 80° C. and then cooling slowly to room temperature. CuSO₄ (aqueous, 20 μL, 100 mM), sodium ascorbate (aqueous, 40 μL, 500 mM), and tris-hydroxypropyltriazole ligand (4 mg) were added. The reaction mixture was left at room temperature for 3 h. Reagents were then removed by NAP-10 gel-filtration and the ligated triazole oligonucleotide was purified by denaturing 12% polyacrylamide gel electrophoresis, and characterized by mass spectrometry (ON15, Table 4). Splint used: 5'-dTGTGTGCTAGCGATCTTA (SEQ ID NO: 17).

TABLE 4

Mass spec analysis of modified oligonucleotides

| ON code | Sequence | Calc mass | Found mass |
|---|---|---|---|
| ON2 | 5'-dCGACG$^{Me}$CtT$^L$TGCAGC (SEQ ID NO: 5) | 3978 | 3978 |
| ON3 | 5'-dCGACG$^{Me}$CtTTGCAGC (SEQ ID NO: 6) | 3950 | 3950 |
| ON5 | 5'-dCGACG$^{Me}$C$^L$tTTGCAGC (SEQ ID NO: 7) | 3978 | 3978 |
| ON6 | 5'-dCGACG$^{Me}$C$^L$tT$^L$TGCAGC (SEQ ID NO: 8) | 4006 | 4006 |
| ON8 | 5'-dCGA$^{Me}$CtT$^L$TCT$^{Me}$CtT$^L$AGC (SEQ ID NO: 9) | 3971 | 3972 |
| ON9 | 5'-dCGA$^{Me}$CtTTCT$^{Me}$CtTAGC (SEQ ID NO: 10) | 3915 | 3915 |

TABLE 4-continued

Mass spec analysis of modified oligonucleotides

| ON code | Sequence | Calc mass | Found mass |
|---|---|---|---|
| ON11 | 5'-dCGACG$^{Me}$Ct$^{Me}$C$^L$TGCAGC (SEQ ID NO: 11) | 3977 | 3977 |
| ON12 | 5'-dCGACG$^{Me}$Ct$^{Me}$CTGCAGC (SEQ ID NO: 12) | 3949 | 3949 |
| ON13 | 5'-dCGA$^{Me}$Ct$^{Me}$C$^L$TCT$^{Me}$Ct$^{Me}$C$^L$AGC (SEQ ID NO: 13) | 3969 | 3970 |
| ON14 | 5'-dCGA$^{Me}$Ct$^{Me}$CTCT$^{Me}$Ct$^{Me}$CAGC (SEQ ID NO: 14) | 3913 | 3914 |
| ON15 | 5'-dGCA TTC GAG CAA CGT AAG ATC G$^{Me}$CtT$^L$ AGC ACA CAA TCT CAC ACT CTG GAA TTC ACA CTG ACA ATA CTG CCG ACA CAC ATA ACC (SEQ ID NO: 28) | 24783 | 24781 |
| ON16 | 5'-dCGACG$^{Me}$C-(alkyne) | 1829 | 1829 |
| ON17 | 5'-dCGA$^{Me}$C(3'-alkyne) | 1210 | 1210 |
| ON18 | 5'-dGCATTCGAGCAACGTAAGATCG $^{Me}$C(3'-alkyne) (SEQ ID NO: 29) | 7110 | 7110 |
| ON19 | 5'-dCGACG$^{Me}$C$^L$-(3'-LNA alkyne) | 1857 | 1857 |
| ON20 | 5'-dN$_3$-$^{Me}$C$^L$TGCAGC | 2148 | 2148 |
| ON21 | 5'-dN$_3$-T$^L$TGCAGC | 2149 | 2149 |
| ON22 | 5'-dN$_3$-$^{Me}$CTGCAGC | 2120 | 2120 |
| ON23 | 5'-dN$_3$-TTGCAGC | 2121 | 2121 |
| ON24 | 5'-dN$_3$-$^{Me}$CAGC | 1197 | 1197 |
| ON25 | 5'-dN$_3$-TAGC | 1198 | 1198 |
| ON26 | 5'-dN$_3$-$^{Me}$C$^L$AGC | 1225 | 1225 |
| ON27 | 5'-dN$_3$-T$^L$AGC | 1226 | 1226 |
| ON28 | 5'-dN$_3$-TTCT$^{Me}$C(3'-alkyne) | 1506 | 1506 |
| ON29 | 5'-dN$_3$-$^{Me}$CTCT$^{Me}$C(3'-alkyne) | 1505 | 1505 |
| ON30 | 5'-dN$_3$-T$^L$TCT$^{Me}$C(3'-alkyne) | 1534 | 1534 |
| ON31 | 5'-dN$_3$-$^{Me}$C$^L$TCT$^{Me}$C(3'-alkyne) | 1533 | 1533 |
| ON32 | 5'-dN$_3$-T$^L$AG CAC ACA ATC TCA CAC TCT GGA ATT CAC ACT GAC AAT ACT GCC GAC ACA CAT AAC C (SEQ ID NO: 30) | 17673 | 17673 | t denotes triazole linkage

Ultraviolet Melting Studies

UV DNA melting curves were recorded in a Cary 4000 Scan UV-Visible Spectrophotometer using 3 μM of each oligonucleotide in a 10 mM phosphate buffer containing 200 mM NaCl at pH 7.0. Samples were annealed by heating to 85° C. (10° C./min) and then slowly cooling to 20° C. (1° C./min). As these six successive cycles (heating and cooling) were performed at a gradient of 1° C./min, the change in UV absorbance at 260 nm was recorded. The melting temperature was calculated from the 1$^{st}$ derivative of the melting curve using in built software.

Results from the application of the above described method are depicted in FIGS. 1 to 4.

Additional $T_m$ Data

TABLE 5

Thermal melting ($T_m$) data for duplexes incorporating a single triazole linkage ($^{Me}C$-$^{Me}C$ step).

| ON Code | ON Sequence | DNA target $T_m{}^a$ | $\Delta T_m{}^b$ | RNA target $T_m{}^a$ | $\Delta T_m{}^b$ |
|---|---|---|---|---|---|
| ON33 | 5'-d CGACG$^{Me}$Cp$^{Me}$CTGCAGC (SEQ ID NO: 31) | 68.7 | | 69.1 | |
| ON11 | 5'-dCGACG$^{Me}$Ct$^{MeL}$TGCAGC (SEQ ID NO: 11) | 63.5 | -5.1 | 68.6 | -0.5 |
| ON12 | 5'-d CGACG$^{Me}$Ct$^{Me}$CTGCAGC (SEQ ID NO: 12) | 62.0 | -6.4 | 63.4 | -5.8 |
| ON34 | 5'-d CGACG$^{Me}$Cp$^{MeL}$TGCAGC (SEQ ID NO: 32) | 72.0 | +3.3 | 74.7 | +5.6 |

$^a$Melting temperatures ($T_m$) were obtained from the maxima of the first derivatives of the melting curves ($A_{260}$ vs. temperature) recorded in a buffer containing 10 mM phosphate and 200 mM NaCl at pH 7.0 using 3.0 μM concentrations of each strand.
$^b\Delta T_m$ = change in $T_m$ for a modified duplex relative to the unmodified duplex (ON33), $^{Me}$C is 5-methylcytosine, $^{MeL}$C is 5-methylcytosine LNA, t denotes a triazole linkage and p denotes a normal phosphodiester linkage. DNA target 5'-dGCT GCA GGC GTC G (SEQ ID NO: 35), RNA target 5'-rGCU GCA GGC GUC G (SEQ ID NO: 36).

TABLE 6

Mismatch discrimination of oligonucleotides incorporating a single triazole linkage ($^{Me}$C-T step) against RNA targets containing a mismatch nucleotide opposite the thymine nucleobase on 3'-side of the triazole linkage.

| | | RNA Target 3'-rGCUGCGMACGUCG | | | |
|---|---|---|---|---|---|
| | | $T_M{}^a$ | $\Delta T_M$ | | |
| ON Code | ON SEQUENCE | M = A | G | C | U |
| ON1 | 5'-dCGACG$^{Me}$CpTTGCAGC (SEQ ID NO: 33) | 62.8 | -3.9 | -16.3 | -13.7 |
| ON2 | 5'-dCGACG$^{Me}$CtT$^L$TGCAGC (SEQ ID NO: 5) | 62.0 | -3.3 | -15.6 | -13.4 |
| ON3 | 5'-dCGACG$^{Me}$CtTTGCAGC (SEQ ID NO: 46) | 56.6 | -2.2 | -16.1 | -12.9 |
| ON4 | 5'-dCGACG$^{Me}$CpT$^L$TGCAGC (SEQ ID NO: 34) | 68.9 | -4.8 | -15.2 | -13.7 |

$^a$See Table 5. $\Delta T_m$ = change in $T_m$ relative to the fully matched duplex (M = A). $^{Me}$C is 5-methylcytosine, $^{MeL}$C is 5-methylcytosine LNA, t denotes a triazole linkage and p denotes a normal phosphodiester linkage.

TABLE 7

Thermal melting ($T_m$) data for duplexes incorporating two triazole linkages ($^{Me}C$-$^{Me}C$ steps).

| ON Code | Sequence | DNA target $T_m{}^a$ | $\Delta T_m$/mod$^b$ | RNA target $T_m{}^a$ | $\Delta T_m$/mod$^b$ |
|---|---|---|---|---|---|
| ON35 | 5'-dCGA$^{Me}$Cp$^{Me}$CTCT$^{Me}$Cp$^{Me}$CAGC (SEQ ID NO: 37) | 66.6 | | 70.1 | |
| ON13 | 5'-dCGA$^{Me}$Ct$^{MeL}$CTCT$^{Me}$Ct$^{MeL}$CAGC (SEQ ID NO: 13) | 56.4 | -5.1 | 67.1 | -1.5 |

TABLE 7-continued

Thermal melting ($T_m$) data for duplexes incorporating two triazole linkages ($^{Me}$C-$^{Me}$C steps).

| ON Code | Sequence | DNA target $T_m{}^a$ | $\Delta T_m/\text{mod}^b$ | RNA target $T_m{}^a$ | $\Delta T_m/\text{mod}^b$ |
|---|---|---|---|---|---|
| ON14 | 5'-dCGA$^{Me}$Ct$^{Me}$CTCT$^{Me}$Ct$^{Me}$CAGC (SEQ ID NO: 14) | 51.9 | −7.3 | 59.1 | −5.5 |
| ON36 | 5'-dCGA$^{Me}$Cp$^{MeL}$C TCT$^{Me}$Cp$^{MeL}$C AGC (SEQ ID NO: 38) | 72.2 | +2.8 | >75 | >+2.5 |

$^{a,b}$see Table 5 footnote. DNA target: 5'-dGCT GGA GAG GTC G (SEQ ID NO: 39), RNA target: 5'-rG CUA GAG AAG UC G (SEQ ID NO: 40)

CD Spectroscopy

CD spectra (200-340 nm) were recorded on a Chirscan Plus spectropolarimeter using a Quartz optical cells with a path length of 3.0 mm Scans were performed at 20° C. using a step size of 0.5 nm, a time per point of 1.0 s and a bandwidth of 2 nm, and the average of four scans is presented. Samples from UV melting studies (3 μM of each oligonucleotide in a 10 mM phosphate buffer containing 200 mM NaCl at pH 7.0) were used directly and were annealed by heating to 85° C. and then slowly cooled to 20° C. prior to recording CD spectrum. The average trace was smoothed (20 points) using in built software. A CD spectrum of only buffer was also recorded and was subtracted from the collected data. Finally, spectra were baseline-corrected using the offset at 340 nm.

Results from the application of the above described method are depicted in FIGS. 5 and 6.

Snake Venom Phosphodiesterase Stability 5 nm of oligonucleotide was dissolved in 50 μL buffer (100 mM Tris-HCl, 20 mM MgCl$_2$, pH=9.0). 10 μL of this solution was removed as a control (zero min) and was diluted with H$_2$O (10 μL). To the remaining solution was added 30 μL H$_2$O followed by 10 μL aqueous solution of Phosphodiesterase 1 from *Crotalus adamanteus* venom (from Sigma Aldrich, catalogue number P3243, 0.45 units, dissolved in 700 μL H$_2$O). The reaction was incubated at 37° C. and aliquots (20 μL) were taken at different time intervals, mixed with formamide (20 μL) and stored at −20° C. The samples were then analysed by denaturing 20% polyacrylamide gel electrophoresis.

Results from the application of the above described method are depicted in FIG. 7.

Linear Copying of an 81-Mer Template Incorporating a Single LNA-Triazole Linkage A reaction mixture was prepared by mixing 10 μL of 10×NEB buffer 2* in a total reaction volume of 100 μL with template, primer or template+primer (110 pmol of each), 0.2 mM dNTP and 1.0 μL of DNA polymerase 1, Large Klenow fragment (5u/μL). Reaction mixture was left at 37° C. for 2.5 h. Phenol:chloroform:isoamyl alcohol (25:24:1, v/v) solution (100 μL) was added and mixture was vortexed for 30 seconds, centrifuged for 5 mM at 5000 rpm. Aqueous phase was collected and sodium acetate (10 μl, 3 M, pH 5.2) and ethanol (330 μL) were added. The mixture was left at −80° C. for 4 h and then centrifuged (13000 rpm) for 20 min at 4° C. The supernatant was removed and the resulting pellet was dissolved in 20 μL H$_2$O. 10 μL sample was used for mass and another 10 μL was analysed by denaturing 10% polyacrylamide gel electrophoresis (Figure S8). Similar gels were obtained when reaction mixture was directly (prior to precipitation) loaded on the gel. Incubation of reaction mixture for 1.5 h showed truncated product in addition to full length product presumably stalling the reaction at the triazole step. The product was analysed by mass spectrometry.

*(10×NEB buffer2 was supplied with the enzyme). 1×NEB buffer 2=50 mM NaCl, 10 mM Tris-HCl, 10 mM MgCl$_2$, 1 mM DTT (pH 7.9 at 25° C.).

Results from the application of the above described method are depicted in FIG. 8.

PCR of an 81-Mer Template Incorporating a Single LNA-Triazole Linkage

PCR amplification of the modified template (ON15) was achieved using GoTaq DNA polymerase. 10 μL of 5× buffer (Promega gree PCR buffer) was used in a total reaction volume of 50 μL with 12.5 ng of the DNA template, 0.5 μM of each primer, 0.2 min dNTP and 1.25 unit of GoTaq polymerase. PCR cyclic conditions: 95° C. (initial denaturation) for 2 min then 3 cycles of 95° C. (denaturation) for 15 s, 54° C. (annealing) for 20 s and 72° C. extension for 5 min. Next 20 cycles 95° C. (denaturation) for 15 s, 54° C. (annealing) for 20 s and 72° C. extension for 30 s. This was followed by leaving the PCR reaction mixture at 72° C. for 5 min. The PCR amplicon was analysed by loading onto 2% agarose gel, and was precipitated following the procedure described for linear copying for mass analysis. Primers used: 5'-dGCATTCGAGCAACGTAAG (SEQ ID NO: 41), 5'-dGGTTATGTGTGTCGGCAG (SEQ ID NO: 42) (for modified template). The unmodified template 5'-dACGT-TAGCACGAAGAGGCATCTTAGCACACAATCT-CACACTCTGGAATT-CACACTGACAATACTCGCGAACACACCCAAT (SEQ ID NO: 2) was used as a control. Primers used: 5'-dAT-TGGGTGTGTTCGCGAG (SEQ ID NO: 43), 5'-dACGT-TAGCACGAAGAGGC (SEQ ID NO: 44). Mass analysis for control: [M+A] strand 1: Calc. 24764, found 24765. Strand 2: Calc. 25167, found 25168.

Results and Discussion

In initial studies we introduced LNA on one or both sides of the triazole linkage (FIG. 1d-f).

13-mer oligonucleotides containing a central MeC-T step were synthesised. The ON sequence used was taken from our previous study.[13] Oligonucleotides were mixed with complementary DNA and RNA targets, and the thermal stabilities of the resulting duplexes were recorded by UV melting (Table 8). Interestingly, the thermal stability of the DNA:RNA duplex containing the triazole linkage with LNA on its 3'-side (ON2) was comparable to that of the unmodified duplex with ON1 (ΔTm=−0.8° C., FIG. 24). LNA significantly improved the stability of the modified DNA: RNA duplex relative to the duplex with only the triazole linkage (an increase of 5.4° C. in Tm, compare ON2 with ON3, RNA target in Table 8). Thus, incorporation of LNA on the 3'-side of the triazole linkage counteracts the drop in the thermal stability caused by the triazole in the context of DNA:RNA duplexes. Duplexes containing a central MeC-t-MeC step also showed similar trends (Table 5). In contrast, 3'-LNA induced only a small increase of 2.9° C. in the thermal stability of dsDNA compared to the duplex containing only the triazole linkage (compare ON2 and ON3 with DNA target) and the stability of the triazole-LNA duplex was still very low compared to the unmodified dsDNA (ON1 vs ON2, ΔTm=−6.0° C.). For duplexes carrying no triazole linkage, LNA had the expected larger effect on binding to RNA targets (ON4, RNA target, ΔTm=6.1° C.) compared to DNA targets (ON4, DNA target ΔTm=3.3° C.). Preferential binding of LNA modified oligonucleotides for RNA targets is well known, and is due to the LNA sugar preferring the 3'-endo conformation.[16,17] Surprisingly, the presence of LNA on the 5'-side of the triazole had no significant additional stabilising effect on DNA:RNA hybrids or DNA duplexes (Table 8, ON5 and ON6).

TABLE 8

Thermal melting ($T_m$) data for duplexes containing a single triazole linkage.

| ON CODE | ON SEQUENCE (5'-3') | DNA TARGET $T_M^A$ | $\Delta T_M^B$ | RNA TARGET $T_M^A$ | $\Delta T_M^B$ |
|---|---|---|---|---|---|
| ON1 | CGACG$^{Me}$CTTGCAGC (SEQ ID NO: 45) | 64.2 | | 62.8 | |
| ON2 | CGACG$^{Me}$CtT$^L$TGCAGC (SEQ ID NO: 5) | 58.2 | −6.0 | 62.0 | −0.8 |
| ON3 | CGACG$^{Me}$CtTTGCAGC (SEQ ID NO: 46) | 55.3 | −8.9 | 56.6 | −6.2 |
| ON4 | CGACG$^{Me}$CT$^L$TGCAGC (SEQ ID NO: 47) | 67.5 | +3.3 | 68.9 | +6.1 |
| ON5 | CGACG$^{Me}$C$^L$tTTGCAGC (SEQ ID NO: 7) | 52.7 | −11.5 | 55.5 | −7.2 |
| ON6 | CGACG$^{Me}$C$^L$tT$^L$TGCAGC (SEQ ID NO: 8) | 58.4 | −5.8 | 62.9 | +0.1 |

$^A$Melting temperatures ($T_m$) were obtained from the maxima of the first derivatives of the melting curves ($A_{260}$ vs. temperature) recorded in a buffer containing, 10 mM phosphate and 200 mM NaCl at pH 7.0 using 3.0 µM concentrations of each strand.
$^B \Delta T_m$ = change in $T_m$ for a modified duplex relative to the unmodified duplex. $T^L$ is LNA thymidine, $^{Me}$C is 5-methylcytosine and t is a triazole linkage (FIG. 1a). DNA target: 5'-dGCT GCA AGC GTC G (SEQ ID NO: 48). RNA target: 5'-rGCU GCA AGC GUC G (SEQ ID NO: 49).

For therapeutic oligonucleotides improved thermal stability must also be accompanied by efficient mismatch discrimination. The ability of the studied oligonucleotides to discriminate between matched and mismatched RNA strands was assessed by mixing them with targets containing a mismatch nucleotide opposite the thymine nucleobase on 3'-side of the triazole linkage (T-X mismatch where X=C, T or G). The oligonucleotides containing triazole-linked 3'-LNA were found to maintain the fidelity of Watson-Crick base pairing, and effectively discriminated against mismatched targets with efficiency parallel to that of unmodified oligonucleotides (Table 6.).

TABLE 9

Thermal melting ($T_m$) data for duplexes incorporating two triazole linkages.

| ON CODE | ON SEQUENCE (5'-3') | DNA TARGET $T_M^A$ | $\Delta T_M/MOD^B$ | RNA TARGET $T_M^B$ | $\Delta T_M/MOD^B$ |
|---|---|---|---|---|---|
| ON7 | CGA$^{Me}$CTTCT$^{Me}$CTAGC (SEQ ID NO: 50) | 57.1 | | 58.8 | |
| ON8 | CGA$^{Me}$CtT$^L$TCT$^{Me}$CtT$^L$AGC (SEQ ID NO: 9) | 48.0 | −4.5 | 57.1 | −0.8 |

TABLE 9-continued

Thermal melting ($T_m$) data for duplexes incorporating two triazole linkages.

| | | DNA TARGET | | RNA TARGET | |
|---|---|---|---|---|---|
| ON CODE | ON SEQUENCE (5'-3') | $T_M^A$ | $\Delta T_M/MOD^B$ | $T_M^B$ | $\Delta T_M/MOD^B$ |
| ON9 | CGA$^{Me}$C$^t$TTCT$^{Me}$C$^t$TAGC (SEQ ID NO: 10) | 42.3 | -7.4 | 47.1 | -5.8 |
| ON10 | CGA$^{Me}$CT$^L$TCT$^{Me}$CT$^L$AGC (SEQ ID NO: 51) | 62.2 | +2.5 | 70.0 | +5.6 |

$^{A,B}$See Table 8 footnote. DNA target; 5'-dGCT AGA GAA GTC G (SEQ ID NO: 52). RNA target; 5'-rGCU AGA GAA GUC G (SEQ ID NO: 18).

Next, oligonucleotides incorporating two triazole internucleotide linkage steps were prepared by templated CuAAC click ligation reactions in the presence of a complementary splint. The ligated oligonucleotides were purified by denaturating 20% polyacrylamide gel electrophoresis and were evaluated for their binding affinity for complementary DNA/RNA strands (Table 9). Pleasingly, oligonucleotides containing two triazole-3'-LNA-linkages (MeC-T steps) showed a significant improvement in binding affinity for their RNA targets relative to oligonucleotides incorporating two triazole linkages without 3'-LNA (an increase of 5.0° C./modification in Tm, compare ON8 and ON9, RNA target). When compared to unmodified ON7, a drop of only 0.8° C./modification was observed (ON8, RNA target). These stability studies suggest that DNA:RNA duplexes can tolerate multiple LNA-triazole linkages, which is not feasible for triazole linkages alone due to the greater lowering of Tm. Since the improvement in binding affinity is specific for DNA:RNA hybrids, triazole-linked LNA could find use in selective probes for RNA targeting. Oligonucleotides incorporating two MeC-t-MeC steps showed similar trends (Table 7).

The global structures of the modified duplexes were also studied by CD-spectroscopy (FIGS. 5 and 6). Both modified and unmodified duplexes showed similar CD spectra suggesting that neither LNA nor triazole-linkage induced any significant change in the global geometry of the studied duplexes.

3'-Exonuclease stability studies using snake venom phosphodiesterase 1 (SVPD, from *Crotalus adamanteus* venom) showed that the combination of triazole and 3'-LNA is more resistant to degradation than unmodified oligonucleotides or those containing only LNA (FIG. 7), and the combination of 5'-LNA-triazole-3'LNA was highly stabilising (FIG. 25). Evidence for the enzyme pausing at the modified backbone linkage is clearly visible (FIG. 25 lane 12). The presence of the triazole seems to protect the unmodified nucleotides on its 3'-side possibly by reducing binding to the enzyme.

Finally, we set out to see if the triazole-linkage in combination with LNA at its 3'-side can be read through by DNA polymerases. To evaluate this, an 81-mer PCR template containing triazole LNA was prepared by a splint assisted CuAAC click ligation reaction. PCR amplification of this modified template was achieved using Gotaq DNA polymerase (FIG. 26). The PCR reaction requires a long extension time for first few cycles (5 min), in agreement with a previous report of LNA-modified templates being amplified by PCR.27 The amplicon was shown by agarose gel electrophoresis and mass spectrometry to be the fully extended product. A linear copying experiment for the same template using DNA polymerase 1, Large Klenow fragment and a reaction time of 2.5 h also gave a fully extended product. Although this extension time is longer than required for templates with only a triazole linkage8 (no LNA) it demonstrates that the combination of LNA and triazole can be reliably read through by DNA polymerases.

While specific embodiments of the invention have been described for the purpose of reference and illustration, various modifications will be apparent to a person skilled in the art without departing from the scope of the invention as defined by the appended claims.

REFERENCES

1. A. H. El-Sagheer and T. Brown, *Chem Soc Rev*, 2010, 39, 1388-1405.
2. T. Fujino, T. Suzuki, K. Okada, K. Kogashi, K. I. Yasumoto, K. Sogawa and H. Isobe, *J Org Chem*, 2016, 81, 8967-8976.
3. K. Kogashi, K. Okada, M. Mattarella, T. Suzuki, K. Yasumoto, K. Sogawa and H. Isobe, *Chem Asian J*, 10, 2683-2688.
4. H. Isobe and T. Fujino, *Chem Rec*, 2014, 14, 41-51.
5. A. M. Varizhuk, D. N. Kaluzhny, R. A. Novikov, A. O. Chizhov, I. P. Smirnov, A. N. Chuvilin, O. N. Tatarinova, G. Y. Fisunov, G. E. Pozmogova and V. L. Florentiev, *J Org Chem*, 2013, 78, 5964-5969.
6. A. M. Varizhuk, V. B. Tsvetkov, O. N. Tatarinova, D. N. Kaluzhny, V. L. Florentiev, E. N. Timofeev, A. K. Shchyolkina, O. F. Borisova, I. P. Smirnov, S. L. Grokhovsky, A. V. Aseychev and G. E. Pozmogova, *Eur J Med Chem*, 2013, 67, 90-97.
7. A. H. El-Sagheer and T. Brown, *Acc Chem Res*, 2012, 45, 1258-1267.
8. A. H. El-Sagheer, A. P. Sanzone, R. Gao, A. Tavassoli and T. Brown, *Proc Natl Acad Sci USA*, 2011, 108, 11338-11343.
9. A. H. El-Sagheer and T. Brown, *Chemical Commun*, 2011, 47, 12057-12058.
10. C. N. Birts, A. P. Sanzone, A. H. El-Sagheer, J. P. Blaydes, T. Brown and A. Tavassoli, *Angew Chem Int Ed*, 2014, 53, 2362-2365.
11. A. Dallmann, A. H. El-Sagheer, L. Dehmel, C. Mügge, C. Griesinger, N. P. Ernsting and T. Brown, *Chem Eur J*, 2011, 17, 14714-14717.
12. V. Madhuri and V. A. Kumar, *Nucleosides, Nucleotides and Nucleic Acids*, 2012, 31, 97-111.
13. A. H. El-Sagheer and T. Brown, *Chem Sci*, 2014, 5, 253-259.
14. A. Shivalingam, A. E. S. Tyburn, A. H. El-Sagheer and T. Brown, *J Am Chem Soc*, 2017, 139, 1575-1583.

15. M. J. Palframan, R. D. Alharthy, P. K. Powalowska and C. J. Hayes, *Org Biomol Chem*, 2016, 14, 3112-3119.
16. S. K. Singh and J. Wengel, *Chem Commun*, 1998, 1247-1248.
17. S. Obika, D. Nanbu, Y. Hari, J. I. Andoh, K. I. Morio, T. Doi and T. Imanishi, *Tetrahedron Lett*, 1998, 39, 5401-5404.
18. H. Kaur, B. R. Babu and S. Maiti, *Chem Rev*, 2007, 107, 4672-4697.
19. J. K. Watts, *Chem Commun*, 2013, 49, 5618-5620.

S1. S. Obika, T. Uneda, T. Sugimoto, D. Nambu, T. Minami, T. Doi, T Imanishi, Bioorg Med Chem 2001, 9, 1001-1011.
S2. A. H. El-Sagheer, A. P. Sanzone, R. Gao, A. Tavassoli and T. Brown, Proc Natl Acad Sci USA, 2011, 108, 11338-11343.
S3. G. P. Miller and E. T. Kool, Org Lett, 2002, 4, 3599-3601.
S4. G. P. Miller and E. T. Kool, J Org Chem, 2004, 69, 2404-2410.
S5. T. R. Chan, R. Hilgraf, K. B. Sharpless and V. V. Fokin, Org Lett, 2004, 6, 2853-2855.

The invention claimed is:
1. A dinucleotide of Formula (I) or Formula (II), or a salt thereof, as shown below:

Formula (I)

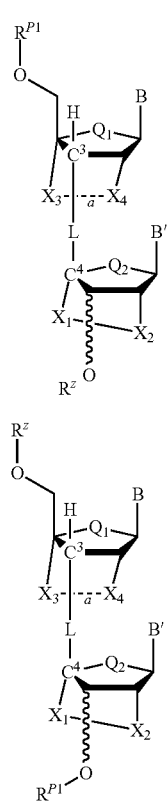

Formula (II)

wherein:
C³ and C⁴ are the carbon atoms at the 3' and 4' positions of their respective 5-membered rings;
$Q_1$ and $Q_2$ are independently selected from $CR^pR^q$, O, S or $NR^s$, wherein $R^p$ and $R^q$ are each independently selected from H, (1-4C)alkyl or halo and $R^5$ is selected from hydrogen or (1-4C)alkyl;
B and B' are each independently:
  a) a nucleobase;
$R^{P1}$ is a protecting group;
one of $X_1$ and $X_2$ is $(CR^aR^b)_x$, wherein x is selected from 1 or 2 and the other is $CR^aR^b$, O, $NR^c$ or S, wherein $R^a$ and $R^b$ are independently selected from hydrogen, (1-2C)alkyl, hydroxy, amino, halo or mercapto, and $R^c$ is selected from hydrogen or a (1-6C)alkyl;
or one of $X_1$ and $X_2$ is O and the other is $NR^c$;
bond a is either absent or a single bond;
one of $X_3$ and $X_4$ is $(CR^dR^e)_y$, wherein y is selected from 1 or 2 and the other is $CR^dR^e$, O, $NR^f$ or S, wherein $R^d$ and $R^e$ are independently selected from hydrogen, (1-2C)alkyl, hydroxy, amino, halo or mercapto, and $R^f$ is selected from hydrogen or a (1-6C)alkyl; or
one of $X_3$ and $X_4$ is O and the other is $NR^f$; or
one of $X_3$ and $X_4$ is H and the other is selected from H, OH, $NH_2$, $OCH_3$ or F;

$R^z$ is a solid support or group of formula $A_1$ or $A_2$ shown below:

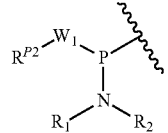

(A₁)

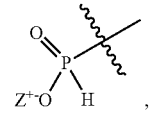

(A₂)

with the proviso that $A_1$ or $A_2$ is not present when $X_3$ is $CR^dR^e$, and $R^d$ and $R^e$ is amino, hydroxyl, or mercapto,
wherein:

denotes the point of attachment;
$W_1$ is selected from O, S or (1-4C)alkyl;
$R^{P2}$ is a protecting group;
$Z^+$ is a positively charged counter ion;
$R_1$ and $R_2$ are independently selected from hydrogen or (1-6C)alkyl, wherein said alkyl is optionally substituted with one or more substituents selected from halo, nitro, cyano or (1-2C)haloalkyl, with the proviso that the halo substituent is not present on the alpha carbon atom; or
$R_1$ and $R_2$ are linked, such that, together with the nitrogen to which they attached they form a pyrrolidin-1-yl ring which is optionally substituted by one or more substituents selected from (1-4C)alkyl, halo, (1-4C)haloalkyl, (1-4C)haloalkoxy, (1-4C)alkoxy, (1-4C)alkylamino, cyano, or nitro; and
L is a triazole phosphodiester mimic, optionally of Formula A or Formula B:

Formula A

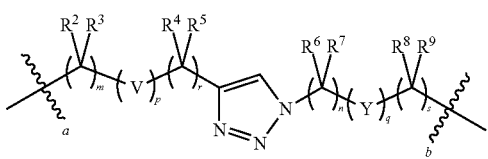

Formula B

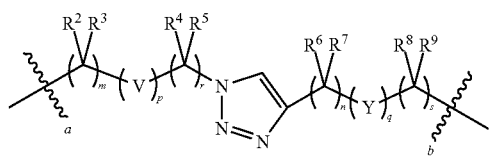

wherein:

denotes the point of attachment to $C^3$;

denotes the point of attachment to $C^4$;
$R^2$, $R^3$, $R^4$, $R^5$, $R^6$, $R^7$, $R^8$ and $R^9$ are each independently selected from hydrogen or (1-4C)alkyl, wherein each (1-4C)alkyl is optionally substituted with one or more $NH_2$, OH or SH;
V and Y are independently selected from O, S or $NR^x$, wherein $R^x$ is selected from hydrogen or (1-4C)alkyl;
m, n, r and s are integers independently selected from 0 to 2; and
p and q are integers independently selected from 0 to 1; with the proviso that:
i) the sum of integers m, n, p, q, r and s is either 0, 1, 2, 3, 4, 5 or 6; and
ii) when $W_1$ is a (1-4C)alkyl, $R^{P2}$ is absent;
iii) bond a is only absent when one of $X_3$ and $X_4$ is H and the other is selected from H, OH, $NH_2$, $OCH_3$ or F.

2. A dinucleotide according to claim 1, wherein the dinucleotide is of Formula I.

3. A dinucleotide according to claim 1, wherein the dinucleotide is of Formula II.

4. A dinucleotide according to claim 2, wherein the $R^z$ is a group of formula $A^1$:

Formula (Ib)

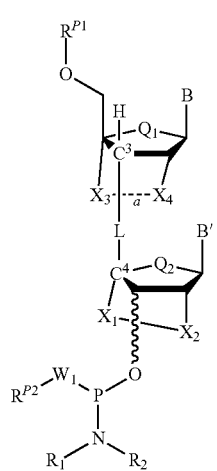

wherein bond a, $C^3$, $C^4$, $Q_1$, $Q_2$, B, B', $R^{P1}$, $R^{P2}$, $W_1$, $R_1$, $R_2$, $X_1$, $X_2$, $X_3$, $X_4$ and L are each as defined in claim 1.

5. A dinucleotide according to claim 4, wherein $W_1$ is O.

6. A dinucleotide according to claim 1, wherein $Q_1$ and $Q_2$ are independently selected from O or S.

7. A dinucleotide according to claim 1, wherein $Q_1$ and $Q_2$ are both oxygen.

8. A dinucleotide according to claim 1, wherein $R^{P1}$ and $R^{P2}$ are protecting groups independently selected from the group consisting of an alkanoyl group, an aroyl group an arylmethyl group, an ether, a silyl ether, an alkylthiol, an alkylcyano, an alkyl thiobenzoyl, trityl-based compound, or a cyclic saturated heterocyclic ring.

9. A dinucleotide according to claim 1, wherein $R^{P1}$ is a trityl-based protecting group.

10. A dinucleotide according to claim 1, wherein $R^{P2}$ is an alkylcyano protecting group.

11. A dinucleotide according to claim 1, wherein one of $X_1$ and $X_2$ is selected from O, $NR^c$ or S and the other of $X_1$ and $X_2$ is $CH_2$, wherein $R^c$ is selected from hydrogen or a (1-6C)alkyl.

12. A dinucleotide according to claim 1, wherein one of $X_1$ and $X_2$ is O, and the other of $X_1$ and $X_2$ is $CH_2$.

13. A dinucleotide according to claim 1, wherein $X_1$ is $CH_2$ and $X_2$ is O.

14. A dinucleotide according to claim 1, wherein bond a is absent and one of $X_3$ and $X_4$ is H and the other is selected from H or OH.

15. A dinucleotide according to claim 1, wherein bond a is a single bond and one of $X_3$ and $X_4$ is selected from O, $NR^f$ or S and the other of $X_1$ and $X_2$ is $CH_2$, wherein $R^f$ is selected from hydrogen or a (1-6C)alkyl.

16. A dinucleotide according to claim 1, wherein bond a is a single bond and one of $X_3$ and $X_4$ is O, and the other of $X_3$ and $X_4$ is $CH_2$.

17. A dinucleotide according to claim 1, wherein bond a is a single bond and $X_3$ is $CH_2$ and $X_4$ is O.

18. A dinucleotide according to claim 1, wherein $R_1$ and $R_2$ are independently selected from hydrogen or (1-6C) alkyl; or $R_1$ and $R_2$ are linked, such that, together with the nitrogen to which they are attached they form a pyrrolidin-1-yl ring.

19. A dinucleotide according to claim 1, wherein $R_1$ and $R_2$ are independently selected from hydrogen or (1-6C)alkyl.

20. A dinucleotide according to claim 1, wherein $R_1$ and $R_2$ are both a (1-4C)alkyl.

21. A dinucleotide according to claim 2, wherein the dinucleotide has the structural Formula (Id) shown below:

Formula (Id)

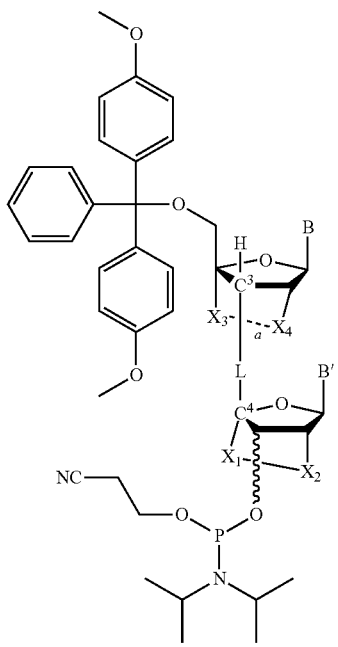

wherein:
C³ and C⁴ are as defined in claim 1;
B and B' are each independently either a nucleobase;
one of $X_1$ and $X_2$ is selected from O, $NR^c$ or S and the other of $X_1$ and $X_2$ is $CH_2$, wherein $R^c$ is selected from hydrogen or a (1-6C)alkyl;
bond a is absent or a single bond;
one of $X_3$ and $X_4$ is selected from O, $NR^f$ or S and the other of $X_1$ and $X_2$ is $CH_2$, wherein $R^f$ is selected from hydrogen or a (1-6C)alkyl; or
one of $X_3$ and $X_4$ is H and the other is selected from H or OH; and
L is a triazole phosphodiester mimic of Formula A or Formula B shown below:

Formula A

Formula B

wherein each of

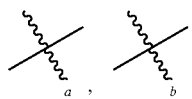

$R^2$, $R^3$, $R^4$, $R^5$, $R^6$, $R^7$, $R^8$, $R^9$, V, Y, m, n, p, q, r and s are as defined in claim 1,
with the proviso that bond a is only absent when one of $X_3$ and $X_4$ is H and the other is selected from H or OH.

22. A dinucleotide according to claim 1, wherein L is a triazole phosphodiester mimic of Formula A or Formula B shown below:

Formula A

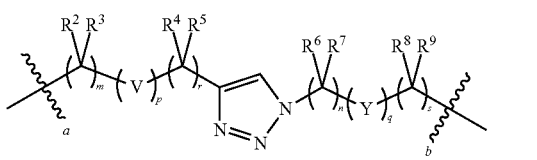

Formula B

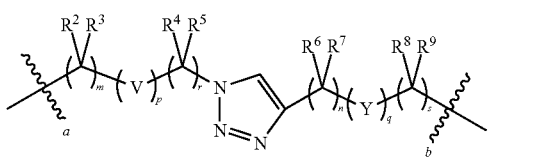

wherein:

denotes the point of attachment to C³;

denotes the point of attachment to C⁴;
$R^2$, $R^3$, $R^4$, $R^5$, $R^6$, $R^7$, $R^8$ and $R^9$ are each independently selected from hydrogen or (1-4C)alkyl;
V and Y are independently selected from O or NW', wherein IV is selected from hydrogen or (1-4C)alkyl;
m, n, r and s are integers independently selected from 0 to 2; and
p and q are integers independently selected from 0 to 1;
with the proviso that the sum of integers m, n, p, q, r and s is either 0, 1, 2, 3, 4 or 5.

23. A dinucleotide according to claim 1, wherein L is a triazole phosphodiester mimic of Formula A or Formula B shown below:

Formula A

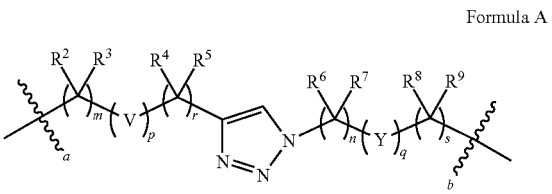

-continued

Formula B

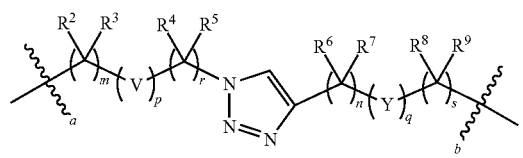

wherein:

denotes the point of attachment to $C^3$;

denotes the point of attachment to $C^4$;

$R^2$, $R^3$, $R^4$, $R^5$, $R^6$, $R^7$, $R^8$ and $R^9$ are hydrogen;

V and Y are O;

m, n, r and s are integers independently selected from 0 to 1; and p and q are integers independently selected from 0 to 1;

with the proviso that the sum of integers m, n, p, q, r and s is either 1, 2, 3, 4 or 5.

24. A dinucleotide according to claim 1, wherein L is a triazole phosphodiester mimic selected from:

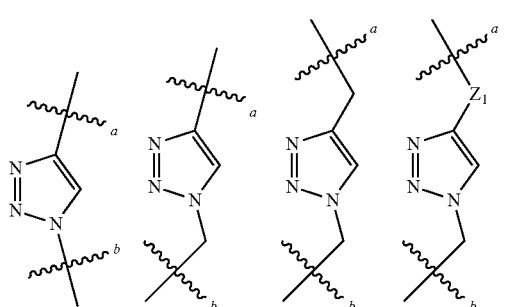

,

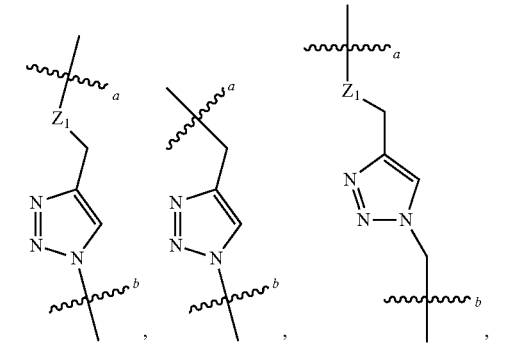

,

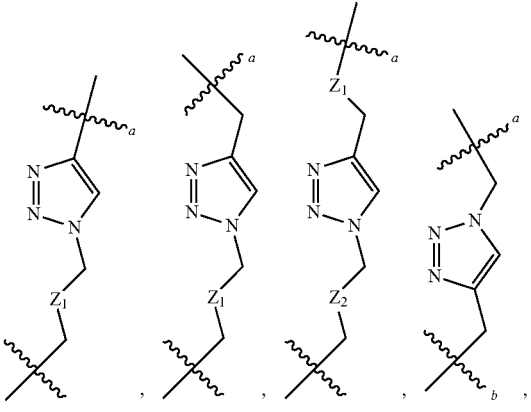

,

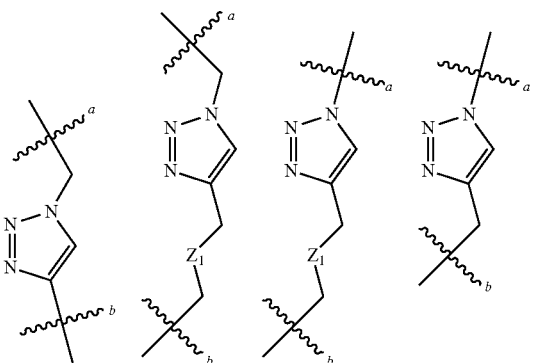

,

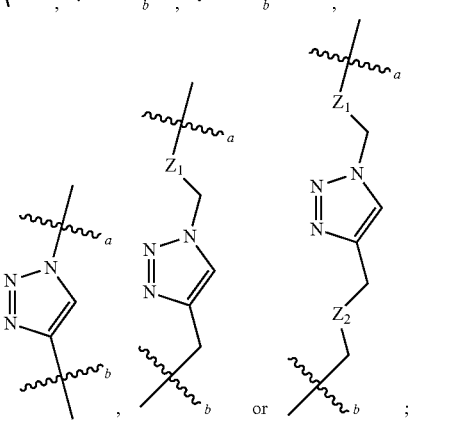

;

$Z_1$ and $Z_2$ are independently selected from O or NH;

denotes the point of attachment to $C^3$;

denotes the point of attachment to $C^4$.

25. A dinucleotide according to claim 2, wherein the dinucleotide has one of the structural formulae given below:

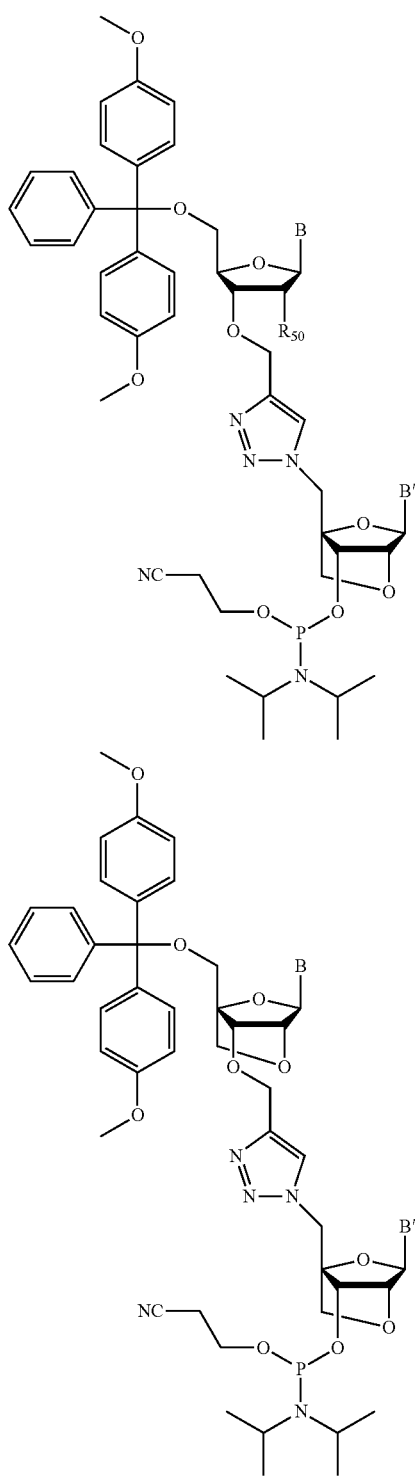

wherein B and B' are each independently a nucleobase and $R_{50}$ is H, OH, $NH_2$, $OCH_3$ or F.

26. A method of preparing a polynucleotide or oligonucleotide having a 5' and a 3' end and comprising a sequence of nucleosides linked together by inter-nucleoside linkages, wherein at least one inter-nucleoside linkage is a triazole linker moiety and the nucleoside attached to the 3' end of the triazole linker moiety is a locked nucleoside, said method involving reacting a dinucleotide according to claim 1 with one or more further nucleotides, dinucleotides and/or oligonucleotides.

27. A method according to claim 26, wherein the oligonucleotide comprises one or more dinucleotide moieties of formula (IV):

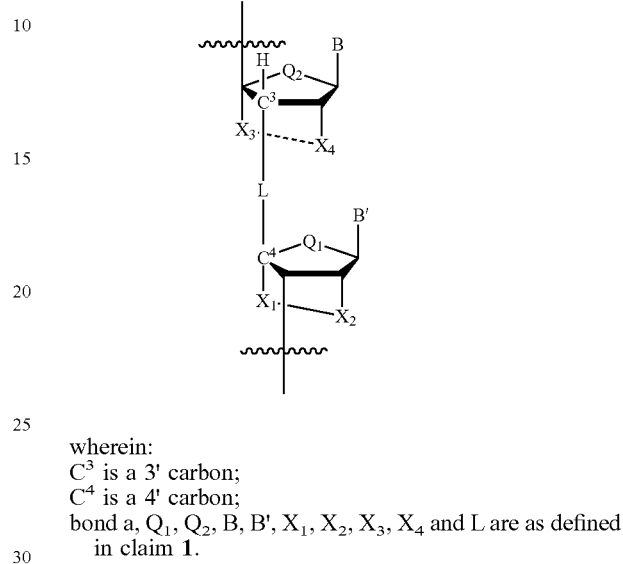

Formula (IV)

wherein:
$C^3$ is a 3' carbon;
$C^4$ is a 4' carbon;
bond a, $Q_1$, $Q_2$, B, B', $X_1$, $X_2$, $X_3$, $X_4$ and L are as defined in claim 1.

28. A dinucleotide of Formula III, or a pharmaceutically acceptable salt thereof, as shown below:

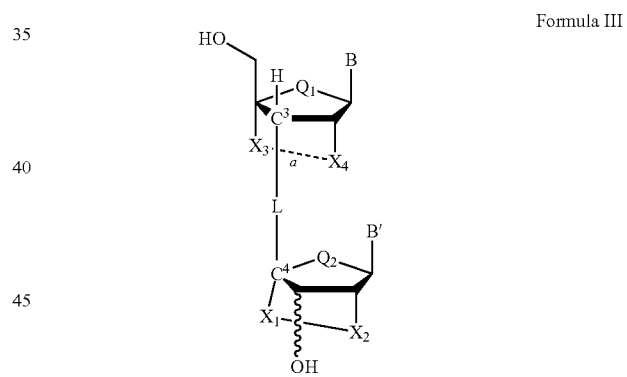

Formula III wherein bond a, $C^3$, $C^4$, $Q_1$, $Q_2$, B, B', $X_1$, $X_2$, $X_3$, $X_4$ and L are each as defined in claim 1.

29. A dinucleotide according to claim 28, wherein $Q_1$ and $Q_2$ are both oxygen.

30. A dinucleotide according to claim 28, wherein one of $X_1$ and $X_2$ is selected from O, $NR^c$ or S and the other of $X_1$ and $X_2$ is $CH_2$, wherein $R^c$ is selected from hydrogen or a (1-6C)alkyl.

31. A dinucleotide according to claim 28, wherein $X_1$ is $CH_2$ and $X_2$ is O.

32. A dinucleotide according to claim 28, wherein bond a is absent and one of $X_3$ and $X_4$ is H and the other is selected from H or OH.

33. A dinucleotide according to claim 28, wherein bond a is a single bond and one of $X_3$ and $X_4$ is O, and the other of $X_3$ and $X_4$ is $CH_2$.

34. A dinucleotide according to claim 28, wherein L is a triazole phosphodiester mimic of Formula A or Formula B shown below:

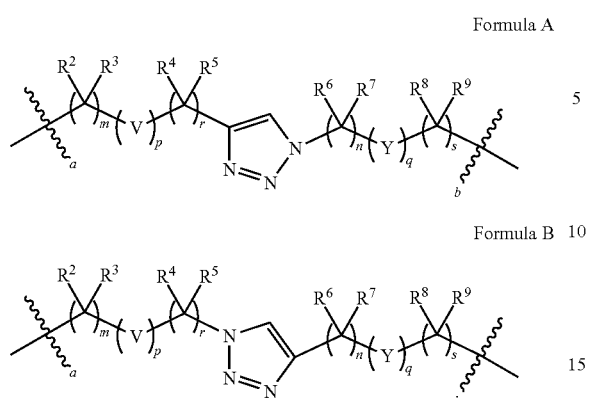

Formula A

Formula B wherein:

denotes the point or attachment to $C_3$;

denotes the point or attachment to $C^4$;
$R^2$, $R^3$, $R^4$, $R^5$, $R^6$, $R^7$, $R^8$ and $R^9$ are hydrogen;
V and Y are O;
m, n, r and s are integers independently selected from 0 to 1; and
p and q are integers independently selected from 0 to 1;
with the proviso that the sum of integers m, n, p, q, r and s is either 1, 2, 3, 4 or 5.

35. A dinucleotide according to claim 28, wherein L is a triazole phosphodiester mimic selected from:

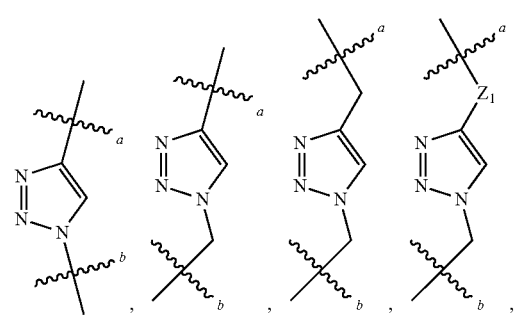

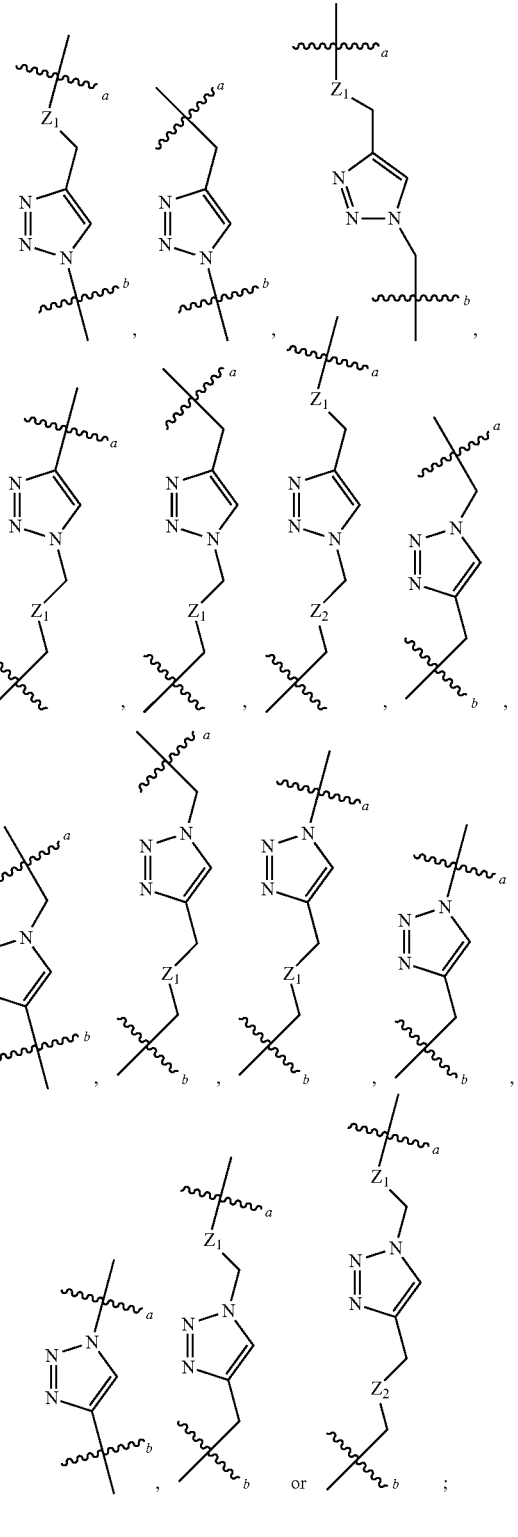

$Z_1$ and $Z_2$ are independently selected from O or NH;

denotes the point of attachment to $C^3$;

117
denoted the point of attachment to $C^4$.
36. A dinucleotide according to claim 28, wherein the dinucleotide has one of the structural formulae given below:
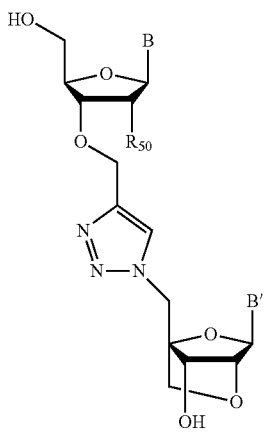
118
-continued
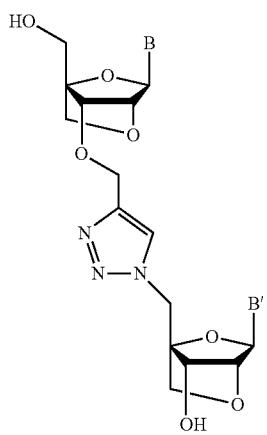
wherein B and B' are each independently a nucleobase and $R_{50}$ is selected from H, OH, $NH_2$, $OCH_3$ or F.
* * * * *